(12) United States Patent
Hashimoto

(10) Patent No.: US 6,630,607 B2
(45) Date of Patent: Oct. 7, 2003

(54) AROMATIC METHYLIDENE COMPOUNDS, AROMATIC ALDEHYDE COMPOUNDS AND METHYLSTYRYL COMPOUNDS USED TO PREPARE THE METHYLIDENE COMPOUNDS, AND METHODS FOR PREPARING THESE COMPOUNDS

(75) Inventor: Mitsuru Hashimoto, Yokohama (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 28 days.

(21) Appl. No.: 10/053,587

(22) Filed: Jan. 24, 2002

(65) Prior Publication Data

US 2002/0147347 A1 Oct. 10, 2002

(30) Foreign Application Priority Data

| Jan. 24, 2001 | (JP) | ......................... 2001-015384 |
| Jan. 24, 2001 | (JP) | ......................... 2001-015385 |
| Jan. 24, 2001 | (JP) | ......................... 2001-015386 |
| Jan. 26, 2001 | (JP) | ......................... 2001-18153 |
| Jan. 26, 2001 | (JP) | ......................... 2001-18154 |

(51) Int. Cl.[7] .................. C07C 45/00; C07C 41/00; C07C 211/00; C07C 255/00; B32B 19/00
(52) U.S. Cl. ................. 568/433; 568/632; 568/633; 568/439; 564/441; 564/315; 558/411; 558/414; 558/415; 558/419; 558/420; 428/690
(58) Field of Search ................ 568/433, 439, 568/632, 633; 564/441, 315; 558/411, 414, 415, 419, 420; 428/690

(56) References Cited

U.S. PATENT DOCUMENTS 4,769,292 A  9/1988  Tang et al. .................. 428/690

FOREIGN PATENT DOCUMENTS

JP  63-264692  11/1988

*Primary Examiner*—Johann Richter
*Assistant Examiner*—Sikarl A. Witherspoon
(74) *Attorney, Agent, or Firm*—McDermott, Will & Emery

(57) ABSTRACT

Aromatic methylidene compounds of the following general formula (1)

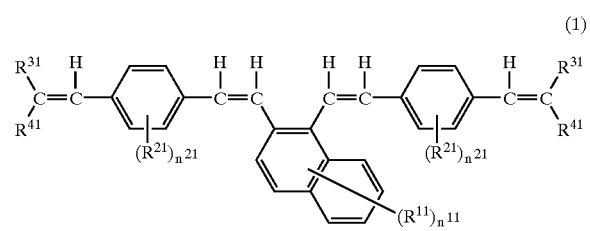

wherein $R^{11}$ and $R^{21}$ independently in each occurrence represent an unsubstituted or substituted alkyl or alkoxy group, a halogen, a cyano group or a nitro group, $n^{11}$ and $n^{21}$ are, respectively, an integer, $R^{31}$ and $R^{41}$ independently represent hydrogen, an unsubstituted or substituted alkyl group, an unsubstituted or substituted cycloalkyl group, an unsubstituted or substituted aromatic group, or an unsubstituted or substituted aromatic heterocyclic group and may join to complete a condensed ring, along with other types of aromatic methylidene compounds wherein the moieties attached to the naphthalene ring are attached to different positions of the ring. The preparation of the methylidene compounds is also described along with intermediate compounds and their preparation.

62 Claims, 7 Drawing Sheets

AROMATIC METHYLIDENE COMPOUNDS, AROMATIC ALDEHYDE COMPOUNDS AND METHYLSTYRYL COMPOUNDS USED TO PREPARE THE METHYLIDENE COMPOUNDS, AND METHODS FOR PREPARING THESE COMPOUNDS

BACKGROUND OF THE INVENTION

1. Field of the Invention

This invention relates to novel aromatic methylidene compounds which are useful as a functional material in electrophotographic photosensitive bodies or as a functional material, such as a charge transport material or a light-emitting material, in organic electroluminescent devices or as a functional material used in other various types of organic semiconductor devices. The invention also relates to intermediate aromatic aldehyde compounds and methylstyryl compounds, both useful for preparing the methylidene compounds, and methods for preparing the intermediate compounds and the methylidene compounds.

2. Description of the Prior Art

Electroluminescent devices that make use of an electroluminescent phenomenon of a substance are self-luminescent in nature, and are thus higher in visuality than liquid crystal devices, ensuring a clear display. Because of the complete solid-state device, they have prominent features of good impact resistance and the like, and are expected as being widely used in the fields of thin displays, back light of liquid crystal displays, plane light sources and the like.

Existing electroluminescent devices are those of a dispersion type which make use of inorganic materials such as zinc sulfide. However, such dispersion-type electroluminescent devices are not in wide use because a relatively high AC voltage is necessary for their drive, with the attendant problem that a drive circuit becomes complicated along with low luminance.

On the other hand, an organic electroluminescent device using organic materials has been proposed by C. W. Tang, for example, in Japanese Laid-open Patent Application No. Hei 63-264692. The device includes a builtup structure of an electron transport organic fluorescent material layer and a hole-transport organic material layer wherein both electron and hole carriers are injected into the fluorescent material layer to permit light emission. It is stated in the application that this electroluminescent device has a much improved luminascent efficiency, and is capable of emission at 1000 cd/m$^2$ or more on application of a voltage of 10V or below. Since the beginning of the above proposal, extensive studies have been made on the related fields of the organic electroluminescent device. At present, various types of materials and device structures have been proposed with extensive studies and developments being directed to practical applications.

Organic electroluminescent devices using materials proposed up to now have, in fact, several problems to solve. Mention is made of some instances of the problems including the lowering of an emission luminance through degradation in function of a device which is only stored irrespective of whether the device is in a driven or non-driven condition, the occurrence of a degradation phenomenon wherein a non-emitting region called dark spot occurs and grows in the course of driving or non-driving, finally resulting in the breakage of the device via short-circuiting.

Such phenomena rely greatly on the fundamental problem of the materials used in the device, and the device may not be satisfactory with respect to the service life thereof. For the service of the device, limitation has to be placed on applications to devices of a type which are responsible only for a relatively short life.

Further, taking the color mode of the device into consideration, systems and light-emitting materials meeting this requirement are not provided satisfactorily at present. In order to solve the above problems and find use in wide fields of organic electroluminescent devices, there has been a strong demand of development of novel materials used in the device such as novel high-performance light-emitting materials, charge transport materials, and the like.

SUMMARY OF THE INVENTION

It is therefore an object of the invention to provide novel aromatic methylidene compounds useful as a light-emitting material so as to realize an organic electroluminescent device that can be driven at low voltage, ensures light emission of high luminance and is excellent in durability.

It is another object of the invention to provide novel aromatic aldehyde compounds and methylstyryl compounds, both useful for preparing the above-mentioned novel aromatic methylidene compounds.

It is a further object of the invention to provide methods for preparing the aromatic methylidene compounds.

It is a still further object of the invention to provide methods for preparing the aromatic aldehyde compounds and methylstyryl compounds, respectively.

According to one embodiment of the invention, there is provided a novel aromatic methylidene compound selected from the group consisting of compounds of the following general formulas (1), (1a), (1b), (1c) and (1d):

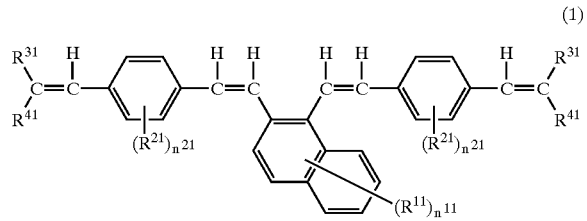

(1)

wherein $R^{11}$ and $R^{21}$ independently in each occurrence represent an unsubstituted or substituted alkyl group, an unsubstituted or substituted alkoxy group, a halogen, e.g. chlorine, bromine, iodine, fluorine, a cyano group or a nitro group, $n^{11}$ is an integer of 0, 1, 2, 3, 4, 5 or 6, and $n^{21}$ is an integer of 0, 1, 2, 3 or 4 provided that when $n^{11}$ and $n^{21}$ are, respectively, an integer of 2 or more, $R^{11}$ and $R^{21}$ may be, respectively, the same or different, and $R^{31}$ and $R^{41}$ independently represent hydrogen except the case where both $R^{31}$ and $R^{41}$ are hydrogen at the same time, an unsubstituted or substituted alkyl group except the case where both $R^{31}$ and $R^{41}$ are an alkyl group at the same time, an unsubstituted or substituted cycloalkyl group except the case where both $R^{31}$ and $R^{41}$ are the cycloalkyl group at the same time, an unsubstituted or substituted aromatic group, or an unsubstituted or substituted aromatic heterocyclic group, or may join to complete a condensed ring of unsubstituted or substituted aromatic rings or unsubstituted or substituted aromatic heterocyclic rings;

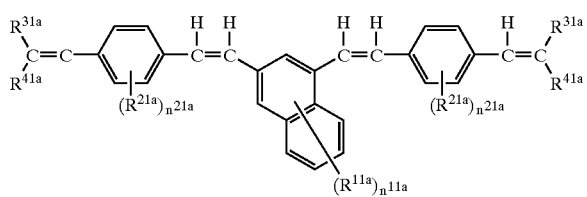
(1a)

wherein $R^{11a}$, $R^{21a}$, $n^{11a}$, $n^{21a}$, $R^{31a}$ and $R^{41a}$, respectively, have the same meanings as $R^{11}$, $R^{21}$, $n^{11}$, $n^{21}$, $R^{31}$ and $R^{41}$ defined with respect to the formula (1);

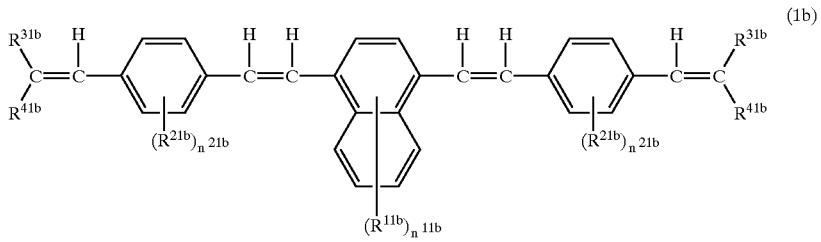
(1b)

wherein $R^{11b}$, $R^{21b}$, $n^{11b}$, $n^{21b}$, $R^{31b}$ and $R^{41b}$, respectively, have the same meanings as $R^{11}$, $R^{21}$, $n^{11}$, $n^{21}$, $R^{31}$ and $R^{41}$ defined with respect to the formula (1);

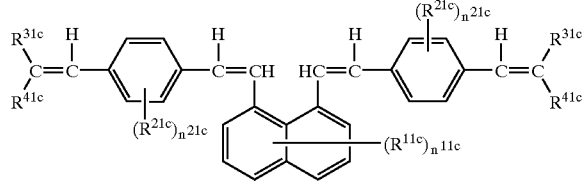
(1c)

wherein $R^{11c}$, $R^{21c}$, $n^{11c}$, $n^{21c}$, $R^{31c}$ and $R^{41c}$, respectively, have the same meanings as $R^{11}$, $R^{21}$, $n^{11}$, $n^{21}$, $R^{31}$ and $R^{41}$ defined with respect to the formula (1), like formulas (1a) and (1c); and

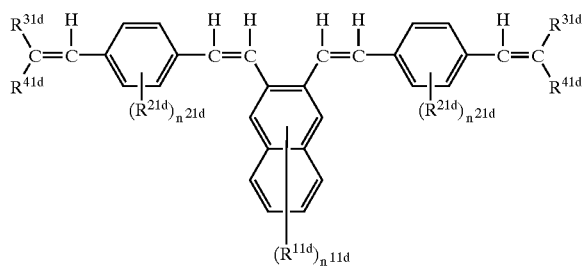
(1d)

wherein $R^{11d}$, $R^{21d}$, $n^{11d}$, $n^{21d}$, $R^{31d}$ and $R^{41d}$, respectively, have the same meanings as $R^{11}$, $R^{21}$, $n^{11}$, $n^{21}$, $R^{31}$ and $R^{41}$ defined with respect to the formula (1), like formulas (1a) and (1c).

According to another embodiment of the invention, there are also provided intermediate compounds useful for preparing the corresponding aromatic methylidene compounds of the above formulas (1), (1a), (1b), (1c) and (1c). The novel intermediate compounds corresponding to the aromatic methylidene compound (1) are indicated as having the following general formulas (2) and (3):

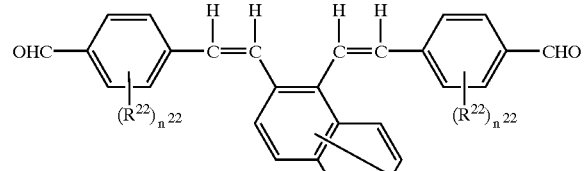
(2)

wherein $R^{12}$ and $R^{22}$, respectively, correspond to $R^{11}$ and $R^{21}$ and independently in each occurrence represent an unsubstituted or substituted alkyl group, an unsubstituted or substituted alkoxy group, a halogen, a cyano group or a nitro group, $n^{12}$ is an integer of 0, 1, 2, 3, 4, 5 or 6, and $n^{22}$ is an integer of 0, 1, 2, 3 or 4 provided that when $n^{12}$ and $n^{22}$ are, respectively, an integer of 2 or more, $R^{12}$'s and $R^{22}$'s may be, respectively, the same or different; and

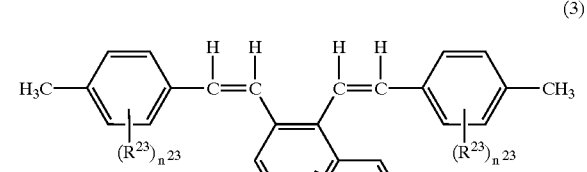
(3)

wherein $R^{13}$ and $R^{23}$, respectively, correspond to $R^{12}$ and $R^{22}$ and independently in each occurrence represent an unsubstituted or substituted alkyl group, an unsubstituted or substituted alkoxy group, a halogen, a cyano group or a nitro group, $n^{13}$ is an integer of 0, 1, 2, 3, 4, 5 or 6, and $n^{23}$ is an integer of 0, 1, 2, 3 or 4 provided that when $n^{13}$ and $n^{23}$ are, respectively, an integer of 2 or more, $R^{13}$'s and $R^{23}$'s may be, respectively, the same or different.

Likewise, the intermediate compounds corresponding to the aromatic methylidene compound (1a) are indicated by the following general formulas (2a) and (3a):

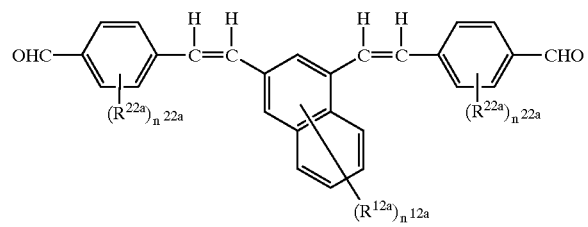
(2a)

wherein $R^{12a}$ and $R^{22a}$, respectively, correspond to $R^{12}$ and $R^{22}$ and independently in each occurrence represent an unsubstituted or substituted alkyl group, an unsubstituted or substituted alkoxy group, a halogen, a cyano group or a nitro group, $n^{12a}$ is an integer of 0, 1, 2, 3, 4, 5 or 6, and $n^{22a}$ is an integer of 0, 1, 2, 3 or 4 provided that when $n^{12a}$ and $n^{22a}$ are, respectively, an integer of 2 or more, $R^{12a}$'s and $R^{22a}$'s may be, respectively, the same or different; and

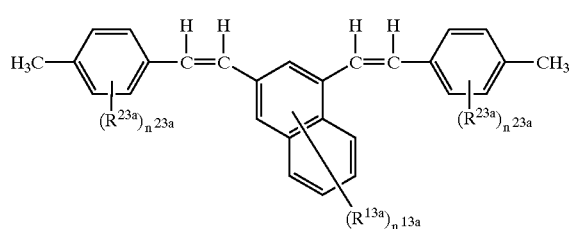
(3a)

wherein $R^{13a}$ and $R^{23a}$, respectively, correspond to $R^{13}$ and $R^{23}$ and independently in each occurrence represent an unsubstituted or substituted alkyl group, an unsubstituted or substituted alkoxy group, a halogen, a cyano group or a nitro group, $n^{13a}$ is an integer of 0, 1, 2, 3, 4, 5 or 6, and $n^{23a}$ is an integer of 0, 1, 2, 3 or 4 provided that when $n^{13a}$ and $n^{23a}$ are, respectively, an integer of 2 or more, $R^{13a}$'s and $R^{23a}$'s may be, respectively, the same or different.

The intermediate compounds corresponding to the aromatic methylidene compound (1b) are indicated by the following general formulas (2b) and (3b):

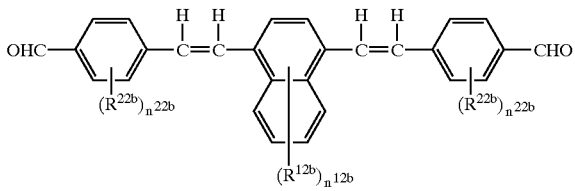
(2b)

wherein $R^{12b}$, $R^{22b}$, $n^{12b}$ and $n^{22b}$, respectively, have the same meanings as $R^{12}$, $R^{22}$ $n^{12}$ and $n^{22}$; and

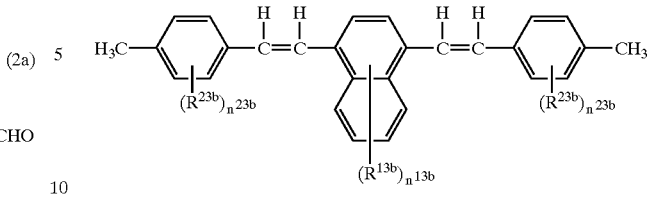
(3b)

wherein $R^{13a}$, $R^{23a}$, $n^{13b}$ and $n^{23b}$, respectively, have the same meanings as $R^{13}$, $R^{23}$ $n^{13}$ and $n^{23}$.

Moreover, the intermediate compounds corresponding to the aromatic methylidene compound (1c) are indicated by the following general formulas (2c) and (3c):

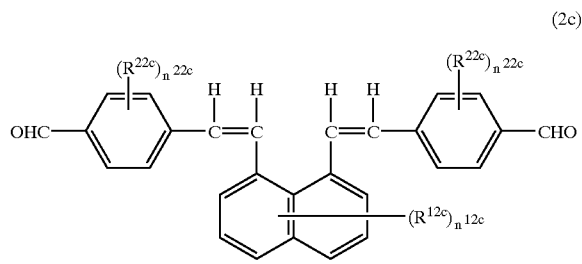
(2c)

wherein $R^{12c}$, $R^{22c}$, $n^{12c}$ and $n^{22c}$, respectively, have the same meanings as $R^{12}$, $R^{22}$ $n^{12}$ and $n^{22}$; and

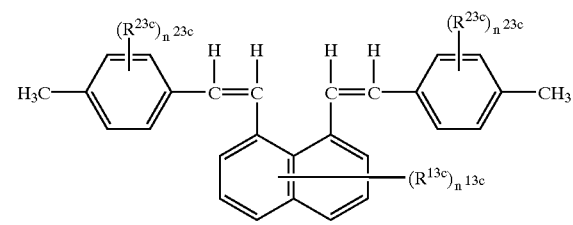
(3c)

wherein $R^{13c}$, $R^{23c}$, $n^{13c}$ and $n^{23c}$, respectively, have the same meanings as $R^{13}$, $R^{23}$ $n^{13}$ and $n^{23}$.

The intermediate compounds corresponding to the aromatic methylidene compound (1d) are indicated by the following general formulas (2d) and (3d):

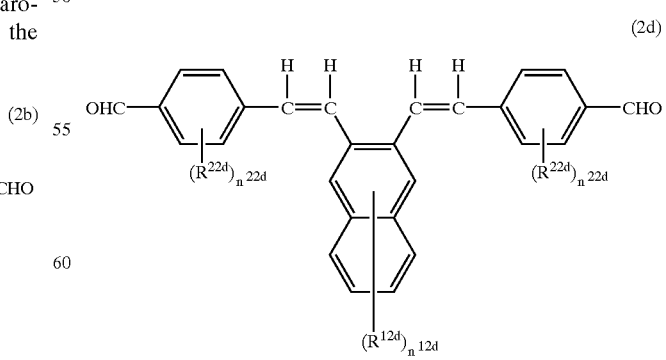
(2d)

wherein $R^{12d}$, $R^{22d}$, $n^{12d}$ and $n^{22d}$, respectively, have the same meanings as $R^{12}$, $R^{22}$ $n^{12}$ and $n^{22}$; and (3d)

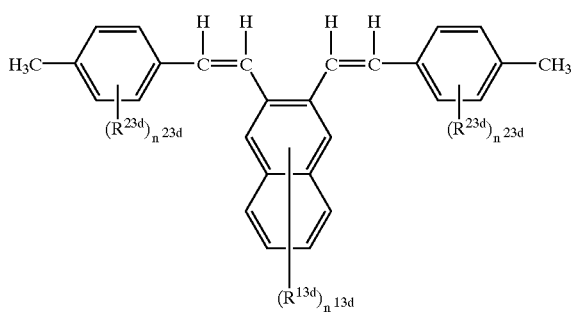

wherein $R^{13d}$ $R^{23d}$, $n^{13d}$ and $n^{23d}$, respectively, have the same meanings as $R^{13}$, $R^{23}$, $n^{13}$ and $n^{23}$.

The intermediate compounds of the above formulas (2), (2a), (2b), (2c), (2d), (3), (3a), (3b), (3c) and (3d) are useful for preparing the novel methylidene compounds (1), (1a), (1b), (1c), (1d), respectively, as one of starting materials for the methylidene compounds. Other types of compounds may also be used for the preparation of the methylidene compounds. More particularly, the aromatic methylidene compound, for example, of the afore-indicated formula (1) may be prepared broadly through four reaction routes including (I) the reaction between a bismethylphosphonic ester derivative and a styrylbenzaldehyde derivative, (II) the reaction between a bis(4-formylstyryl)naphthalene derivative and a methylphosphonic ester derivative, (III) the reaction between a phthalaldehyde derivative and a methylphosphonic ester derivative, and (IV) the reaction between a bismethylphosphonic ester derivative and a ketone derivative. In addition, the methylidene compound may also be prepared by using, in place of the methylphosphonic ester derivatives in (I) to (IV), corresponding methyltriarylphosphonium salts.

This is true of the preparation of the methylidene compounds of the general formulas (1a), (1b), (1c) and 1(d). Accordingly, the preparation of these compounds is first described with respect to the methylidene compound of the formula (1).

Thus, according to a further embodiment of the invention, there is provided a method for preparing an aromatic methylidene compound of the general formula (1). As described hereinabove, the methylidene compound is obtainable broadly through the four different reaction routes (I) to (IV) set out hereinbelow.

(I) The methylidene compound of the formula (1) is prepared by reaction between a bismethylphosphonic ester derivative of the following formula (4), or a corresponding methyl triarylphosphonium compound thereof wherein the aryl moiety includes, for example, phenyl, tolyl or the like herein and whenever it the term "corresponding methyl triarylphosphonium compound" appears hereafter and, and a benzaldehyde derivative of the following formula (5);

(4)

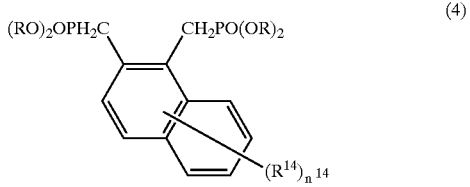

wherein $R^{14}$ represents an unsubstituted or substituted alkyl group, an unsubstituted or substituted alkoxy group, both as defined with respect to $R^{11}$ in the general formula (1), a halogen group, a cyano group or a nitro group, $n^{14}$ is an integer of 0, 1, 2, 3, 4, 5 or 6 provided that if $n^{14}$ is an integer of 2 or over, $R^{14}$'s may be the same or different, and R represents an unsubstituted or substituted alkyl group; and (5)

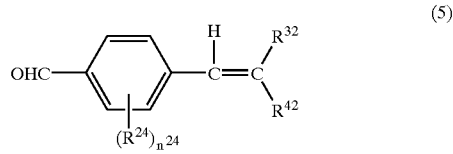

wherein $R^{24}$ represents an unsubstituted or substituted alkyl group, an unsubstituted or substituted alkoxy group, both as defined with respect to $R^{21}$ in the general formula (1), a halogen group, a cyano group or a nitro group, $n^{24}$ is an integer of 0, 1, 2, 3 or 4 provided that if $n^{24}$ is an integer of 2 or over, $R^{24}$'s may be the same or different, and $R^{32}$ and $R^{42}$, respectively, have the same meanings as $R^{31}$ and $R^{41}$ in the formula (1) and independently represent hydrogen except the case where both $R^{32}$ and $R^{42}$ are hydrogen at the same time, an unsubstituted or substituted alkyl group except the case where both $R^{32}$ and $R^{42}$ are an alkyl group at the same time, an unsubstituted or substituted cycloalkyl group except the case where both $R^{32}$ and $R^{42}$ are the cycloalkyl group at the same time, an unsubstituted or substituted aromatic group, or an unsubstituted or substituted aromatic heterocyclic group, or may join to complete a condensed ring of unsubstituted or substituted aromatic rings or unsubstituted or substituted aromatic heterocyclic rings.

(II) The methylidene compound of the formula (1) is also obtained by reaction between a bis(4-formylstyryl) naphthalene derivative of the afore-indicated general formula (2) and a methylphosphonic ester derivative of the following general formula (6) or a corresponding methyl triarylphosphonium compound thereof;

(6)

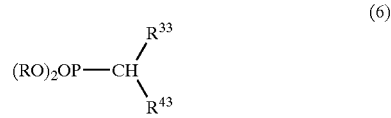

wherein $R^{33}$ and $R^{43}$, respectively, have the same meanings as $R^{31}$ and $R^{41}$ in the formula (1), like $R^{32}$ and $R^{42}$, and R represents an unsubstituted or substituted alkyl group having from 1 to 4 carbon atoms.

(III) The methylidene compound of the formula (1) is obtained by reaction between a phthalaldehyde derivative of the following general formula (7) and a methylphosphonic ester derivative of the following general formula (8), or a corresponding methyl triarylphosphonium compound thereof:

(7)

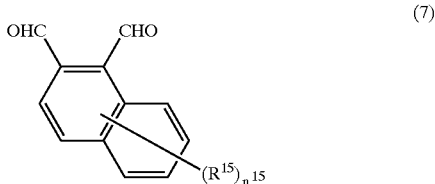

wherein $R^{15}$ has the same meaning as $R^{11}$ in the formula (1) and $n^{15}$ has the same meaning as $n^{11}$ provided that when $n^{15}$ is 2 or over, $R^{15}$'s may be the same or different; and

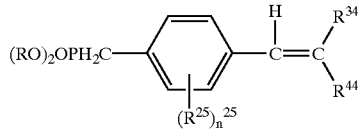

(8)

wherein $R^{25}$ has the same meaning as $R^{21}$ in the formula (1), $n^{25}$ is an integer of 0, 1, 2, 3 or 4 provided that if $n^{25}$ is 2 or over, $R^{25}$'s may be the same or different, $R^{34}$ and $R^{44}$, respectively, have the same meanings as $R^{31}$ and $R^{41}$, like $R^{32}$ and $R^{42}$ and the like, and R represents an unsubstituted or substituted alkyl group as defined in the foregoing formulas.

(IV) The methylidene compound of the formula (1) is also obtained by reaction between a bismethylphosphonic ester derivative of the following general formula (9), or a corresponding methyl triarylphosphonium compound thereof, and a ketone derivative of the following general formula (10):

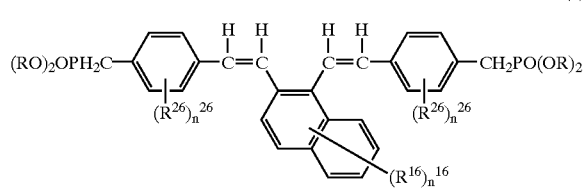

(9)

wherein $R^{16}$ and $R^{26}$, respectively, have the same meanings as $R^{11}$ and $R^{21}$ in the formula (1) and $n^{16}$ is an integer of 0, 1, 2, 3, 4, 5, or 6 and $n^{26}$ is an integer of 0, 1, 2, 3 or 4 provided that if $n^{16}$ and $n^{26}$, respectively, are 2 or over, $R^{16}$'s and $R^{26}$'s may be the same or different, and R represents an unsubstituted or substituted alkyl group defined in the foregoing formulas; and

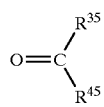

(10)

wherein $R^{35}$ and $R^{45}$, respectively, have the same meanings as $R^{31}$ and $R^{41}$ in the formula (1).

The preparation of other types of methylidene compounds represented by the general formulas (1a), (1b), (1c) and (1d) is likewise feasible using slightly different types of starting materials, and four reaction routes of individual methylidene compounds are depicted below as (Ia) to (IV a) to (Id) to (IV d) wherein like symbols, such as 11, 11a, 11b, 11c, 11d, in the chemical formulas indicate like groups or values and are not defined in the following formulas.

(Ia) The methylidene compound of the formula (1a) is prepared by reaction between a bismethylphosphonic ester derivative of the following formula (4a), or a corresponding methyl triarylphosphonium compound thereof, and a benzaldehyde derivative of the following formula (5a);

(4a)

(5a)

(IIa) The methylidene compound of the formula (1a) is also obtained by reaction between a bis(4-formylstyryl) naphthalene derivative of the afore-indicated general formula (2a) and a methylphosphonic ester derivative of the following general formula (6a) or a corresponding methyl triarylphosphonium compound thereof;

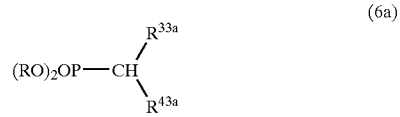

(6a)

(IIIa) The methylidene compound of the formula (1a) is obtained by reaction between a phthalaldehyde derivative of the following general formula (7a) and a methylphosphonic ester derivative of the following general formula (8a), or a corresponding methyl triarylphosphonium compound thereof:

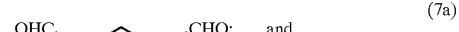

(7a)

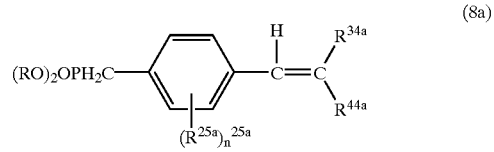

(8a)

(IV a) The methylidene compound of the formula (1a) is also obtained by reaction between a bismethylphosphonic ester derivative of the following general formula (9a), or a corresponding methyl triarylphosphonium compound thereof, and a ketone derivative of the following general formula (10a):

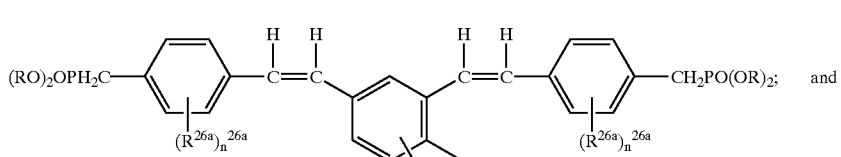

(9a)

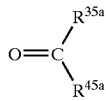

(10a)

(Ib) The methylidene compound of the formula (1b) is prepared by reaction between a bismethylphosphonic ester derivative of the following formula (4b), or a corresponding methyl triarylphosphonium compound thereof, and a benzaldehyde derivative of the following formula (5b);

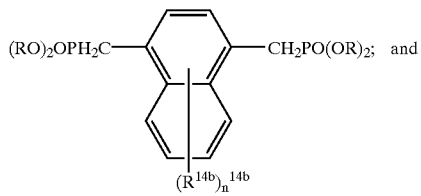

(4b)

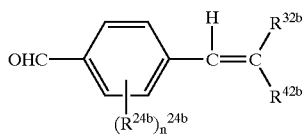

(5b)

(IIb) The methylidene compound of the formula (1b) is also obtained by reaction between a bis(4-formylstyryl) naphthalene derivative of the afore-indicated general formula (2b) and a methylphosphonic ester derivative of the following general formula (6b) or a corresponding methyl triarylphosphonium compound thereof;

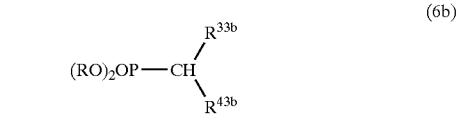

(6b)

(IIIb) The methylidene compound of the formula (1b) is obtained by reaction between a phthalaldehyde derivative of the following general formula (7b) and a methylphosphonic ester derivative of the following general formula (8b), or a corresponding methyl triarylphosphonium compound thereof:

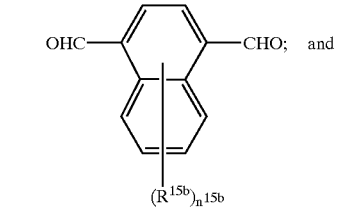

(7b)

(8b)

(IVb) The methylidene compound of the formula (1b) is obtained by reaction between a bismethylphosphonic ester derivative of the following general formula (9b), or a corresponding methyl triarylphosphonium compound thereof, and a ketone derivative of the following general formula (10b):

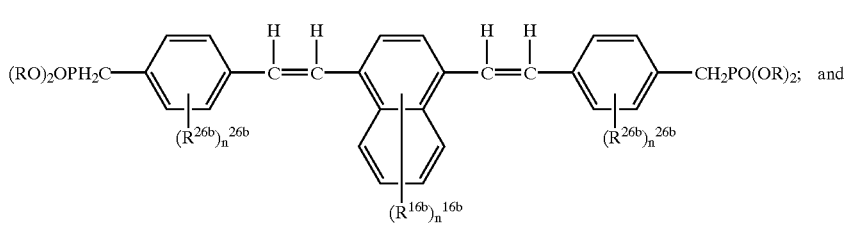

(9b)

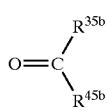

(Ic) The methylidene compound of the formula (1c) is prepared by reaction between a bismethylphosphonic ester derivative of the following formula (4c), or a corresponding methyl triarylphosphonium compound thereof, and a benzaldehyde derivative of the following formula (5c);

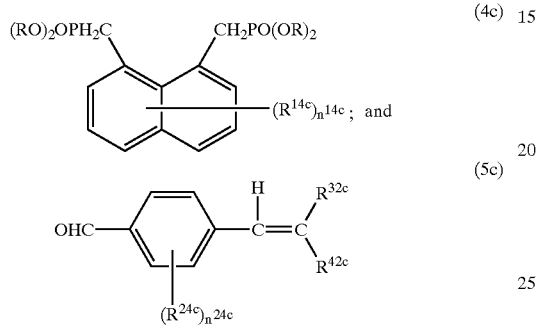

(IIc) The methylidene compound of the formula (1c) is also obtained by reaction between a bis(4-formylstyryl) naphthalene derivative of the afore-indicated general formula (2c) and a methylphosphonic ester derivative of the following general formula (6c) or a corresponding methyl triarylphosphonium compound thereof;

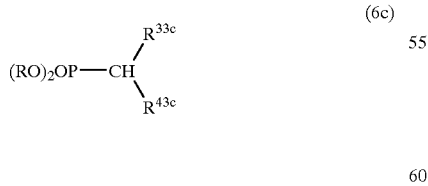

(IIIc) The methylidene compound of the formula (1c) is obtained by reaction between a phthalaldehyde derivative of the following general formula (7c) and a methylphosphonic ester derivative of the following general formula (8c), or a corresponding methyl triarylphosphonium compound thereof:

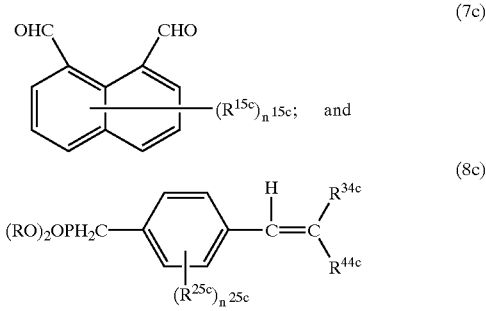

(IV c) The methylidene compound of the formula (1c) is obtained by reaction between a bismethylphosphonic ester derivative of the following general formula (9c), or a corresponding methyl triarylphosphonium compound thereof, and a ketone derivative of the following general formula (10c):

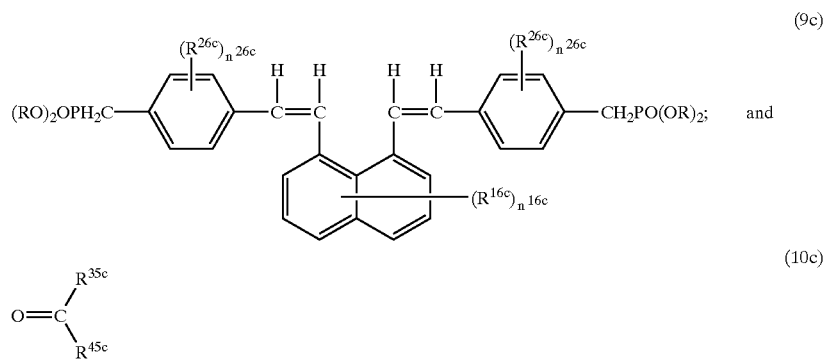

(Id) The methylidene compound of the formula (1d) is prepared by reaction between a bismethylphosphonic ester derivative of the following formula (4d), or a corresponding methyl triarylphosphonium compound thereof, and a benzaldehyde derivative of the following formula (5d);

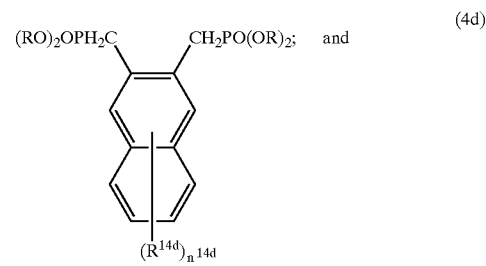

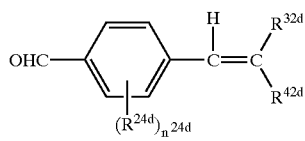
(5d)

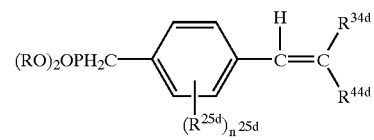
(8d)

(IId) The methylidene compound of the formula (1d) is also obtained by reaction between a bis(4-formylstyryl) naphthalene derivative of the afore-indicated general formula (2d) and a methylphosphonic ester derivative of the following general formula (6d) or a corresponding methyl triarylphosphonium compound thereof;

(IV d) The methylidene compound of the formula (1d) is obtained by reaction between a bismethylphosphonic ester derivative of the following general formula (9d), or a corresponding methyl triarylphosphonium compound thereof, and a ketone derivative of the following general formula (10d):

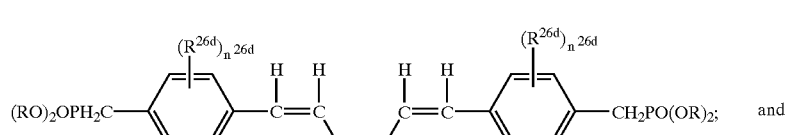
(9d) and

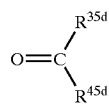
(10d)

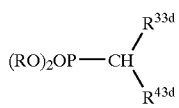
(6d)

(IIId) The methylidene compound of the formula (1d) is obtained by reaction between a phthalaldehyde derivative of the following general formula (7d) and a methylphosphonic ester derivative of the following general formula (8d), or a corresponding methyl triarylphosphonium compound thereof:

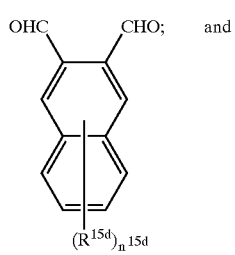
(7d)

Next, the preparation of the intermediate compounds of the afore-indicated formulas (2), (2a), (2b), (2c), (2d), and (3), (3a), (3b), (3c), (3d) are described.

The compound of the general formula (2) is prepared by reaction between the bismethylphosphonic ester derivative of the afore-indicated formula (4), or a corresponding methyl triarylphosphonium compound thereof, and an aldehyde compound of the following general formula (11)

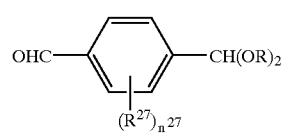
(12)

wherein $R^{27}$ represents a unsubstituted or substituted alkyl group, an unsubstituted or substituted alkyl group, a halogen atom, a cyano group or a nitro group as defined in $R^{22}$ in the formula (2), $n^{27}$ is an integer of 0, 1, 2, 3 or 4 provided that if $n^{27}$ is 2 or over, $R^{27}$'s may be the same or different, and R represents an unsubstituted or substituted alkyl group as defined in the foregoing formulas, followed by conversion of the resultant acetal compound into an aldehyde compound.

Likewise, the compounds of the general formulas (2a), (2b), (2c) and (2d) are, respectively, prepared in the same manner as stated above, but using the reaction between each of the bismethylphosphonic ester derivatives of the afore-indicated formula (4a), (4b), (4c) and 4(d) and the compound of the above-indicated compound of the formula (11), followed by conversion of the resultant acetal compounds into corresponding aldehyde compounds.

Further, the compound of the general formula (2) may also be prepared by reaction between the bismethylphosphonic ester derivative of the afore-indicated formula (4), or a corresponding methyl triarylphosphonium compound thereof, and a tolualdehyde compound of the following general formula (12)

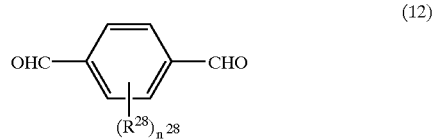

(12)

wherein $R^{28}$ represents a unsubstituted or substituted alkyl group, an unsubstituted or substituted alkyl group, a halogen atom, a cyano group or a nitro group as defined in $R^{27}$ in the formula (11), and $n^{28}$ is an integer of 0, 1, 2, 3 or 4 provided that if $n^{28}$ is 2 or over, $R^{28}$'s may be the same or different.

In the latter case, no conversion reaction is necessary.

The compounds of the general formulas (2a), (2b), (2c) and (2d) are also prepared in the same manner as mentioned above using the ester derivatives of the afore-indicated general formulas (4a), (4b), (4c) and (4d), respectively.

The compound of the general formula (3) is prepared by reaction between the bismethylphosphonic ester derivative of the afore-indicated formula (4), or a corresponding methyl triarylphosphonium compound thereof, and an aldehyde compound of the following general formula (13):

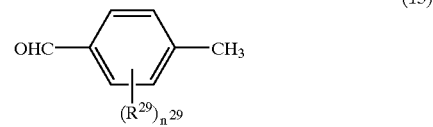

(13)

wherein $R^{29}$ represents an unsubstituted or substituted alkyl group, an unsubstituted or substituted alkoxy group, a halogen atom, a cyano group or a nitro group as defined as $R^{14}$ in the formula (4), and $n^{29}$ is an integer of 0, 1, 2, 3 or 4 provided that if $n^{29}$ is 2 or over, $R^{29}$'s may be the same or different.

The compounds of the general formulas (3a), (3b), (3c) and (3c) can be, respectively, prepared in the same manner as stated above but using, in place of the compound of the general formula (4), the compounds of the afore-indicated general formulas (4a), 4(b), 4(c) and 4(d), respectively.

Moreover, the compound of the general formula (3) may also be prepared by reaction between the aromatic aldehyde compound of the afore-indicated formula (7) and a methylphosphonic ester derivative of the following general formula (14) or a corresponding methyl triarylphosphonium compound thereof:

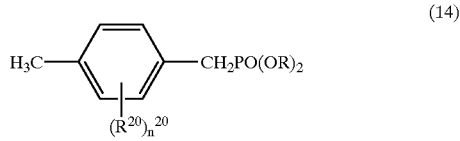

(14)

wherein $R^{20}$ represents an unsubstituted or substituted alkyl group, an unsubstituted or substituted alkoxy group, a halogen atom, a cyano group or a nitro group as defined as $R^{23}$ in the afore-indicated formula (3), $n^{20}$ is an integer of 0, 1, 2, 3 or 4 provided that if $n^{20}$ is 2 or over, $R^{20}$'s may be the same or different, and R represents an unsubstituted or substituted alkyl group having from 1 to 4 carbon atoms.

Likewise, the compounds of the afore-indicated general formulas (3a), (3b), (3c) and (3d) can be prepared in the same manner as set our above but using the compounds of the afore-indicated formulas (7a), (7b), (7c) and (7d) in place of the compound of the formula (7).

DETAILED DESCRIPTION OF THE PREFERRED EMBODIMENTS

Figure 1:
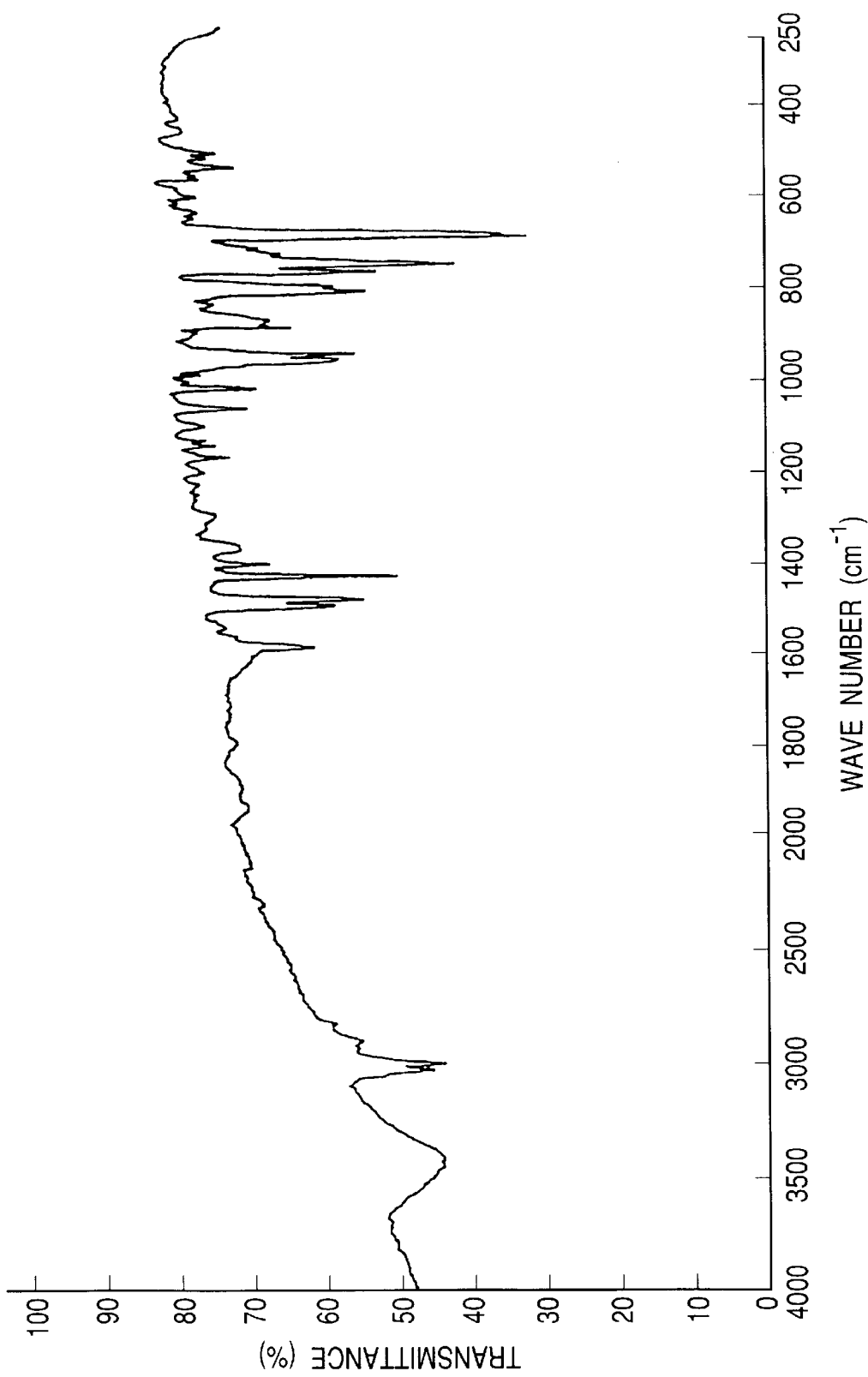
FIG. 1 is a spectrogram showing infrared absorption spectra of compound No. 1-02 according to the invention.
Figure 2:
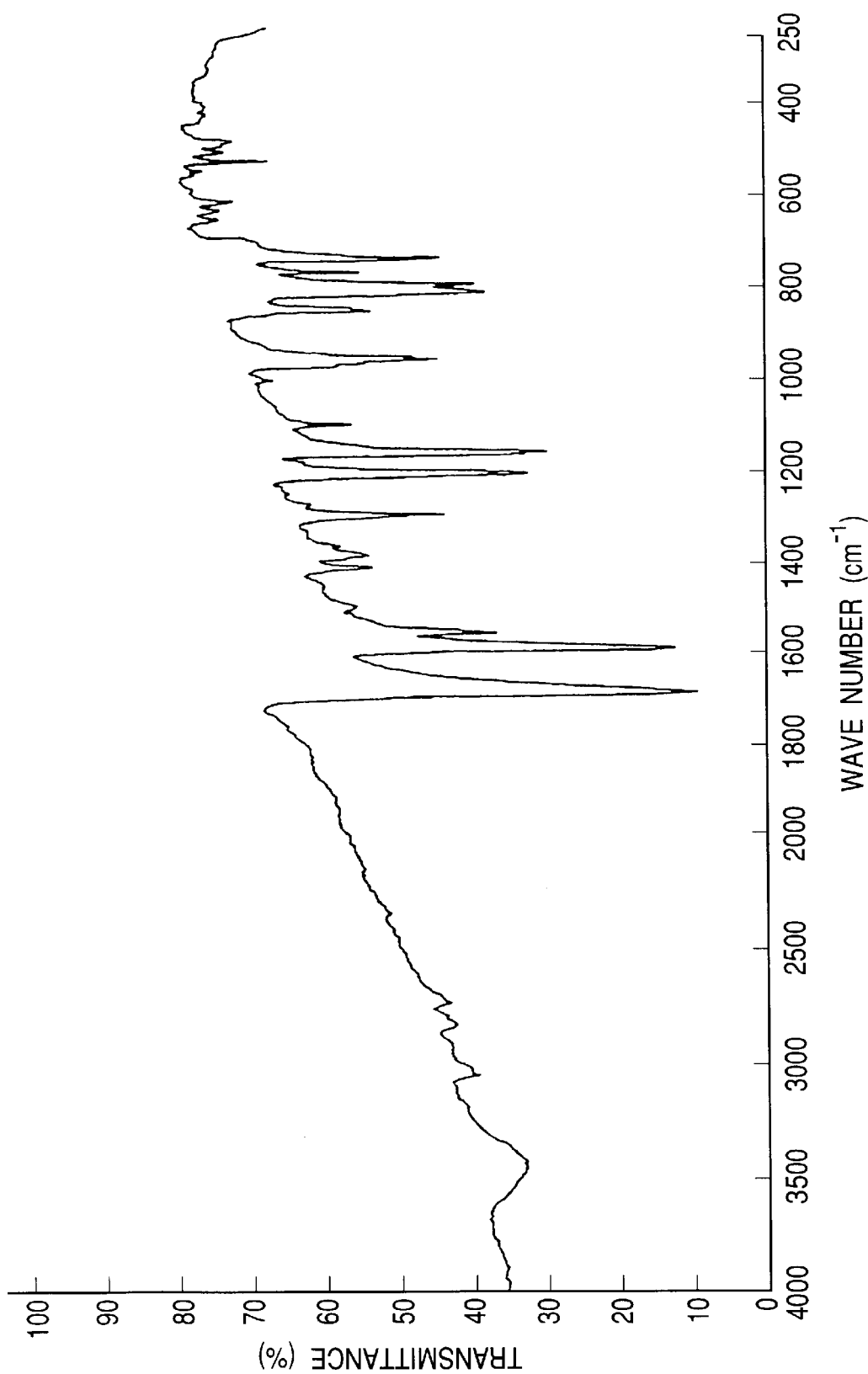
FIG. 2 is a spectrogram showing infrared absorption spectra of compound No. 2-01 according to the invention.

The compounds of the general formulas (1), (1a), (1b), 1(c) and (1d) according to the invention are, respectively, useful as a constituent material of an organic electroluminescent device and particularly excellent as a luminescent material. The compounds of the general formulas (2) to (2d) and (3) to (3d) are useful as intermediates for preparing the compounds of the general formulas (1) to (1d), respectively. The compounds provided according to the invention and also the preparation thereof would greatly contribute to the realization of an organic electroluminescent device ensuring high luminance emission and high durability.

Initially, the compounds of the general formulas (1), (1a), (1b), (1c) and 1(d) are described. For convenience's sake, the aromatic methylidene compound of the formula (1) is mainly described because the other compounds of the formulas (1a) to (1d) differ from the compound of the formula (1) only with respect to the positions of the moieties attached to the naphthalene ring. In these compounds, the substituents indicated by like symbols are similar or identical to one another.

In the compound of the general formula (1), $R^{11}$ and $R^{21}$ independently in each occurrence represent an unsubstituted or substituted alkyl group, an unsubstituted or substituted alkoxy group, a halogen, a cyano group or a nitro group, $n^{11}$ is an integer of 0, 1, 2, 3, 4, 5 or 6, and $n^{21}$ is an integer of 0, 1, 2, 3 or 4 provided that when $n^{11}$ and $n^{21}$ are, respectively, an integer of 2 or more, $R^{11}$'s and $R^{21}$'s may be, respectively, the same or different, and $R^{31}$ and $R^{41}$ may be the same or different and independently represent hydrogen except the case where both $R^{31}$ and $R^{41}$ are hydrogen at the same time, an unsubstituted or substituted alkyl group provided that both $R^{31}$ and $R^{41}$ are an alkyl group at the same time, an unsubstituted or substituted cycloalkyl group provided that both $R^{31}$ and $R^{41}$ are the cycloalkyl group at the same time, an unsubstituted or substituted aromatic group or an unsubstituted or substituted aromatic heterocyclic group and may join to complete a condensed ring of unsubstituted or substituted aromatic rings or unsubstituted or substituted aromatic heterocyclic rings.

The unsubstituted or substituted alkyl group represented by $R^{11}$ and $R^{21}$ preferably has from 1 to 8 carbon atoms and includes, for example, methyl, ethyl, n-propyl, n-butyl, n-pentyl, n-hexyl, n-heptyl, n-octyl, iso-butyl, sec-butyl, methoxylmethyl, chloromethyl, trifluoromethyl, benzyl, phenetyl or the like.

Likewise, the unsubstituted or substituted alkoxy group preferably has from 1 to 8 carbon atoms and includes, for example, methoxy, ethoxy, n-propoxy, n-butoxy, n-hexyloxy, n-octyloxy, iso-propoxy, sec-butoxy, chloromethyloxy, trifluoromethyloxy, benzyloxy or the like.

The halogen includes chlorine, bromine, iodine or fluorine. $n^{11}$ is preferably a value of 0, and $n^{21}$ is preferably a value of 0.

The substituted or unsubstituted alkyl group represented by $R^{31}$ and $R^{41}$ may be one defined with respect to $R^{11}$ and $R^{21}$.

The unsubstituted or substituted cycloalkyl group has from 3 to 8 carbon atoms and includes, for example, cyclopropane, cyclopentane, cyclohexane, 4-methylcyclohexane, cycloheptane or the like.

Examples of the unsubstituted or substituted aromatic ring and unsubstituted or substituted aromatic heterocyclic ring include phenyl, xylyl, furyl, pyridyl, quinolyl, chienyl, phenanthryl and the like.

The rings formed by joining of $R^{31}$ and $R^{41}$ to complete a condensed ring of unsubstituted or substituted aromatic rings and/or unsubstituted or substituted aromatic heterocyclic rings include, for example, those rings indicated below:

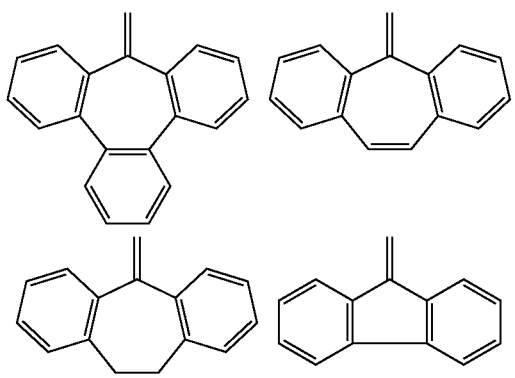

The preparation of the aromatic methylidene compound of the general formula (1) is now described.

As described hereinbefore, not only the compound of the general formula (1), but also the respective compounds of the general formulas (1a) to (1d) can be broadly prepared according to four procedures. More particularly, the compound of the general formula (1) can be prepared by (I) reaction between a bismethylphosphonic ester derivative of the afore-indicated formula (4), and a benzaldehyde derivative of the afore-indicated formula (5), (II) reaction between a bis(4-formylstyryl)naphthalene derivative of the afore-indicated general formula (2) and a methylphosphonic ester derivative of the afore-indicated general formula (6), (III) by reaction between a phthalaldehyde derivative of the afore-indicated general formula (7) and a methylphosphonic ester derivative of the afore-indicated general formula (8), and (IV) reaction between a bismethylphosphonic ester derivative of the afore-indicated general formula (9), and a ketone derivative of the afore-indicated general formula (10).

The substituent groups and the suffixes in the formulas (4) to (10) are, respectively, ones that have been defined hereinbefore and are not repeatedly set forth herein.

In the respective procedures, the methylphosphonic ester derivatives of the formulas (4), (6), (8) and (9) may be replaced by corresponding methyltriarylphosphonium salts wherein the aryl includes phenyl, tolyl or the like as set forth hereinbefore.

All the reactions (I) to (IV) are those reactions between the aldehydes and active methylene and are usually carried out in an organic solvent. The solvent for the reactions may be water, an alcohol such as methanol, ethanol, butanol, amyl alcohol or the like, an aromatic hydrocarbon such as benzene, toluene, xylene, mesitylene, chlorobenzene, nitrobenzene or the like, an ether such as diethyl ether, tetrahydrofuran, dioxane or the like, a halogenated hydrocarbon such as chloroform, dichloromethane, dichloroethane or the like, a heterocyclic aromatic hydrocarbon such as pyridine, quinoline, and other type of compound such as N,N-dimethylformamide, dimethylsulfoxide or the like. Besides, ordinarily employed organic solvents may also be used without limitation.

Bases are used for all the reactions so as to cause the reaction to proceed smoothly. Examples of the base include inorganic bases such as potassium carbonate, sodium carbonate, potassium hydroxide, sodium hydroxide and the like, organic bases such as triethylamine, triethanolamine, pyridine and hexamethylenetetramine and the like, alkali metal alcoholates such as sodium methoxide, sodium ethoxide, potassium butoxide and the like, and sodium amides. The amount of a base ranges from a catalytic amount to a stoichiometric amount or over as required.

All the reactions proceed under relatively mild reaction conditions. More particularly, the reaction may be carried out at a temperature ranging from about −10° C. to about 150° C., preferably about 0° C. to about 80° C. The reaction time usually depends on the reaction temperature and ranges from about 30 minutes to about 100 hours. The reaction time should be properly selected depending on the combination of starting materials.

In order to obtain an intended product from a reaction mixture after completion of reaction, the reaction mixture may be concentrated or diluted with a bad solvent to obtain a crude product in the form of crystals or a solid matter. Examples of such a bad solvent include alcohols such as methanol, ethanol and the like. Preferably, the crude product is washed with water to remove inorganic matters therefrom. Thereafter, the crude product is purified through an ordinary purifying technique such as chromatography, recrystallization or sublimation, thereby obtaining a pure product.

Next, the novel intermediate compound of the afore-indicated general formula (2) is now described. In the formula (2), $R^{12}$, $R^{22}$, $n^{12}$ and $n^{22}$, respectively, have the same meanings as $R^{11}$, $R^{21}$, $n^{11}$ and $n^{21}$.

This intermediate compound (2) may be prepared by a procedure wherein a bismethylphosphonic ester derivative of the afore-indicated general formula (4) and a monodialkylacetal of a terephthalaldehyde derivative of the afore-indicated general formula (11) are reacted with each other, after which the resulting acetal compound is converted to an aldehyde compound by use of a diluted acid such as a diluted hydrochloric acid, a diluted sulfuric acid or the like while heating the reaction system. Alternatively, when using a terephthalaldehyde derivative of the afore-indicated general formula (12) in place of the monodialkylacetal of the terephthalaldehyde derivative, there can be directly obtained the intermediate compound (2).

The novel intermediate compound of the afore-indicated general formula (3) is described. In the general formula (3), $R^{13}$ and $R^{23}$ are, respectively, similar or identical to $R^{11}$ and $R^{21}$ defined in the general formula (1), $n^{13}$ has the same meaning as $n^{11}$ in the formula (1) and is an integer of 0, 1, 2, 3, 4, 5 or 6, and $n^{23}$ has the same meaning as $n^{13}$ in the formula (1) and is an integer of 0, 1, 2, 3 or 4. The intermediate compound (3) is obtained by reaction between the bismethylphophonic ester derivative of the afore-indicated general formula (4) and the tolualdehyde of the afore-indicated general formula (12) or by reaction between the phthalaldehyde derivative of the afore-indicated general formula (7) and the methylphosphonic ester derivative of the afore-indicated general formula (14).

These reactions for the compounds of the general formulas (2) and (3) are those reactions between the aldehydes and the active methylene compounds, like the reactions for the compound of the general formula (1). The reactions are usually performed in an organic solvent by use of a base. The reaction solvent and base used herein may, respectively, be ones which are illustrated with respect to the preparation of the compound of the general formula (1). This is true of the reaction conditions, which are not repeatedly set out again.

The compound of the general formula (3) is particularly important as an intermediate for obtaining the bismethylphosphonic ester derivative of the general formula (9), which is useful as a starting material for obtaining the compound of the general formula (1). More particularly, the compound of the general formula (3) is converted to a halomethyl product of the following general formula (15), followed by reaction with a trialkyl phosphite to conveniently obtain a bismethylphosphonic ester derivative of the afore-indicated general formula (9)

(15)

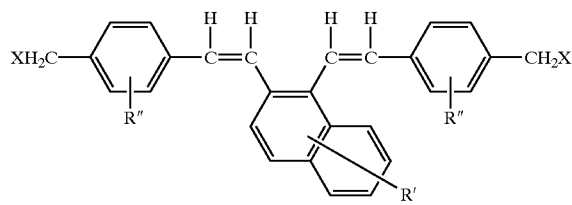

wherein R' and R" independently represent a substituent group such as $R^{16}$, $R^{26}$ in the general formula (9) and X represents a halogen such as F, Cl, Br or I.

It will be noted that when using, in place of the compound of the general formula (3), the compounds of the afore-indicated general formulas (3a), (3b), 3(c) and (3d), corresponding halomethyl products have the following general formulas (15a), (15b), (15c) and (15d):

(15a)

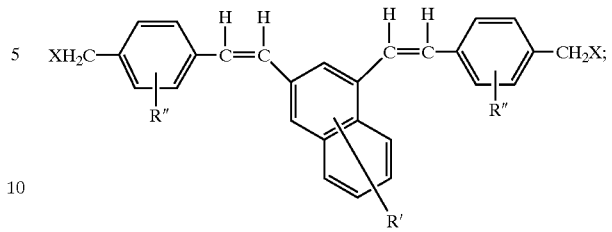

(15b)

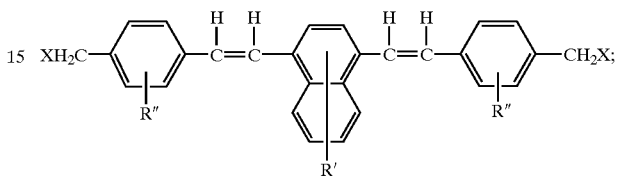

(15c)

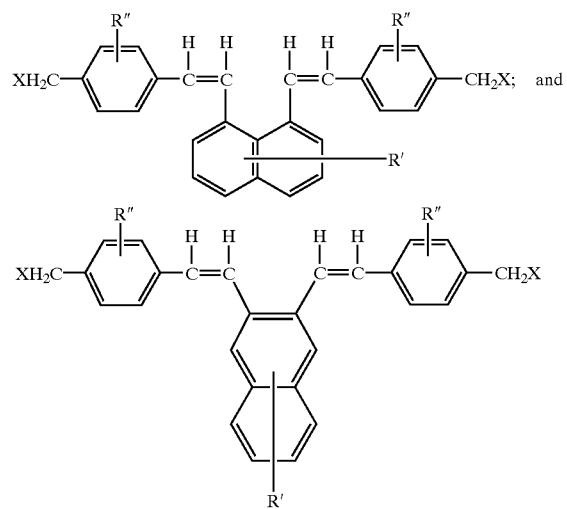

wherein R', R" and X in each occurrence independently have the same meanings as defined above.

The intermediate compounds of the formulas (2) and (3) and their preparation have been described above. It should be noted that the intermediate compounds of the formulas (2a) to (2d) and the preparations thereof are similar to the compounds (2) and (3) and the preparations thereof particularly with respect to the substituents attached thereof and the manner of preparation including reaction conditions such as the reaction temperature, time and the like, solvents and bases, and the like, and thus such compounds and preparations are not specifically described herein.

The compounds of the general formulas (1) to (1d) according to the invention have similar chemical structures but with methylidene moieties being attached to the naphtyl group at different positions as shown in the respective general formulas. These compounds can be prepared in a similar way, and have different characteristic properties when applied to as an electroluminescent material. From the standpoint of electroluminescent characteristics, the compound of the general formula (1) is better than the other types of compounds and is thus preferred although the other compounds are also usable as an electroluminescent material.

It should be noted that $R^{11}$ to $R^{16}$ and $R^{20}$ to $R^{29}$ in the general formulas (1) to (14) and like symbols, such as $R^{11a}$, $R^{11b}$, $R^{11c}$, $R^{11d}$ to $R^{21a}$, $R^{21b}$, $R^{21c}$, $R^{21d}$ etc., in the corresponding general formulas of (1a) to (1d) to (14a) to (14d), respectively, the same meaning as defined, particularly, in the general formula (1).

Likewise, $R^{31}$ to $R^{35}$ and $R^{41}$ to $R^{45}$ in the general formulas (1), (5), (6), (8) and (10) as well as like symbols in the corresponding general formulas (1a) to (1d) and the like, respectively, have the same meaning as particularly defined in the general formula (1). This is true of the value of $n^{11}$ to $n^{16}$ in the general formulas (1) to (4), (7) and (9) and of the values of the like symbols such as $n^{11a}$, $n^{11b}$, etc., in the corresponding general formulas (1a) to (1d) and the like. This is also true of the value of $n^{20}$ to $n^{29}$ and the like symbols.

Now, specific and, in fact, preferred examples of the compounds of the general formulas (1) to (1d), (2) to (2d) and (3) to (3d) are shown in the following tables.

TABLE 1

| Compound No. | Structural Formula |
| --- | --- |
| 1-01 | |
| 1-02 | |
| 1-03 | |
| 1-04 | |

TABLE 1-continued
| Compound No. | Structural Formula |
| --- | --- |
| 1-05 | 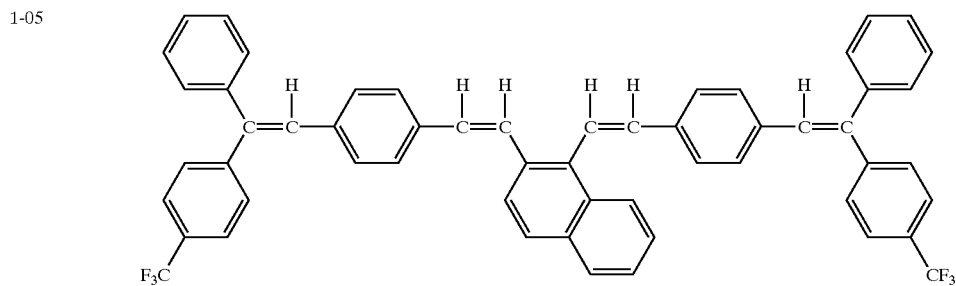 |
| 1-06 | 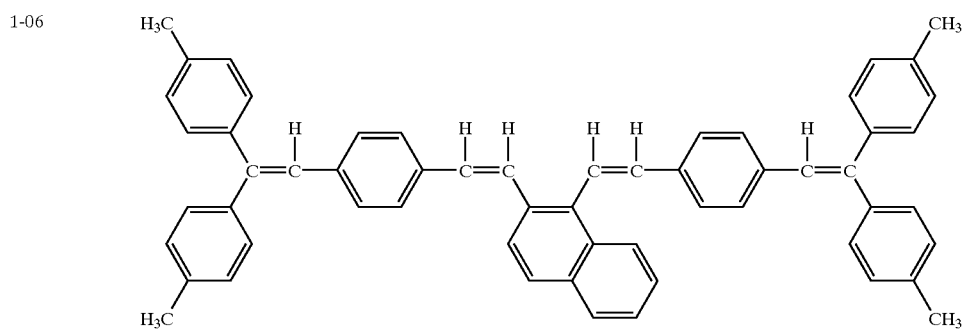 |
| 1-07 | 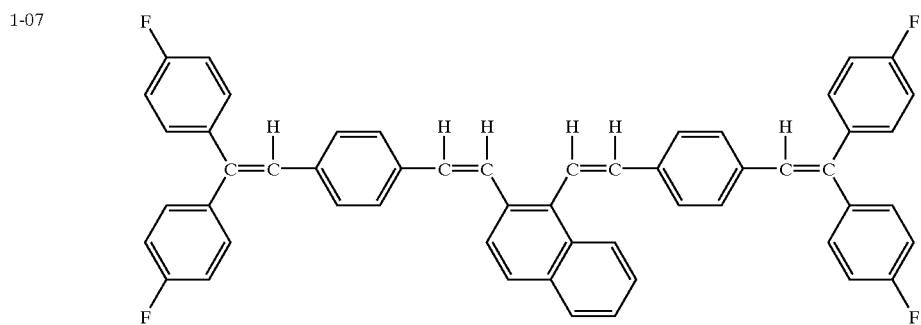 |
TABLE 1-1
| Compound No. | Structural Formula |
| --- | --- |
| 1-08 | 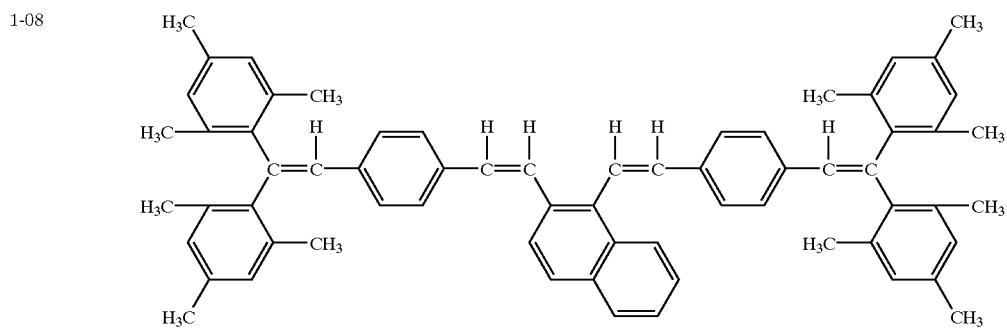 |

TABLE 1-1-continued
| Compound No. | Structural Formula |
|---|---|
| 1-09 | 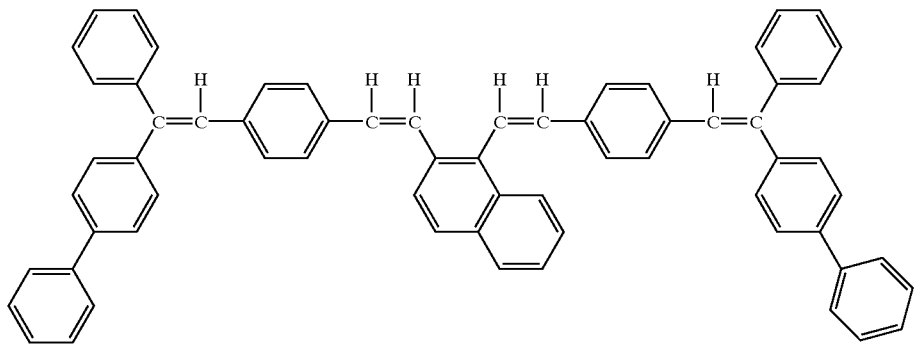 |
| 1-10 | 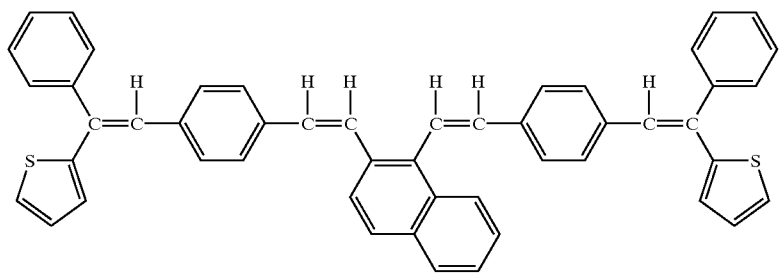 |
| 1-11 | 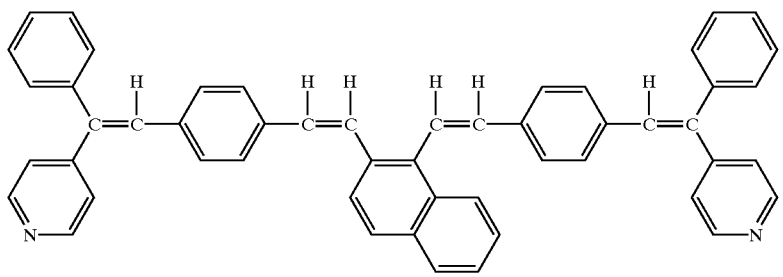 |
| 1-12 | 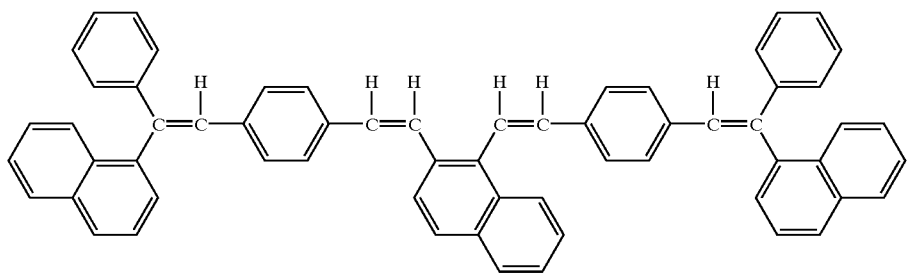 |
| 1-13 | 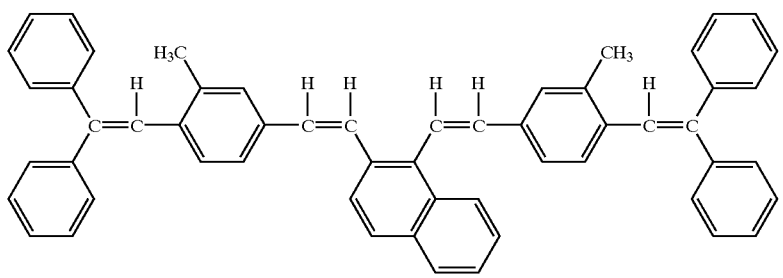 |

TABLE 1-2
| Compound No. | Structural Formula |
| --- | --- |
| 1-14 | 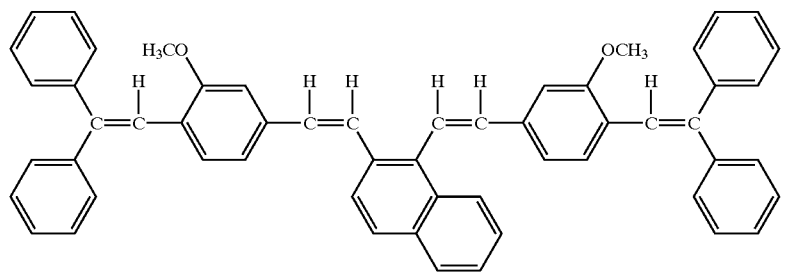 |
| 1-15 | 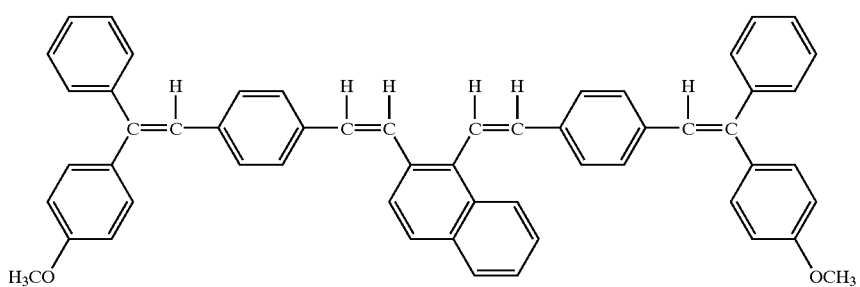 |
| 1-16 | 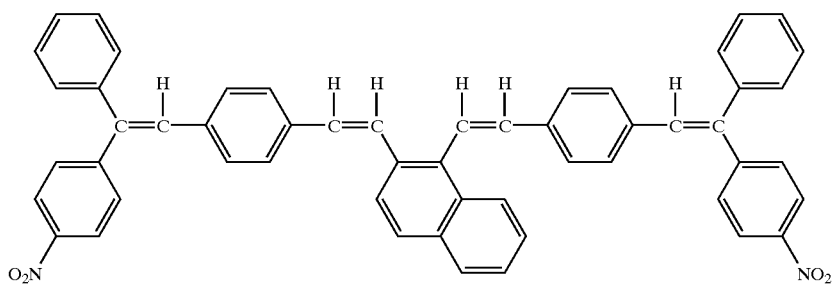 |
| 1-17 | 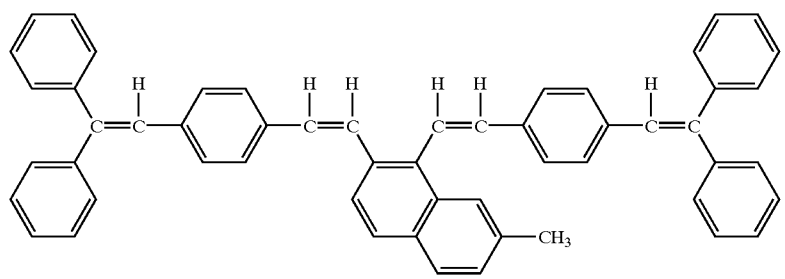 |
| 1-18 | 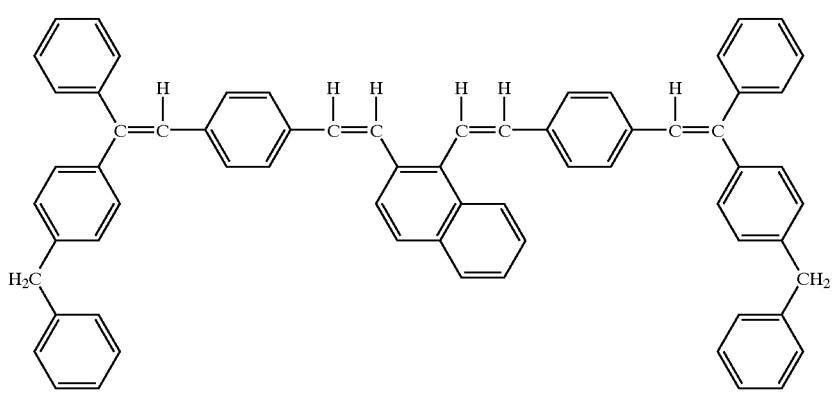 |

TABLE 1-2-continued
| Compound No. | Structural Formula |
|---|---|
| 1-19 | 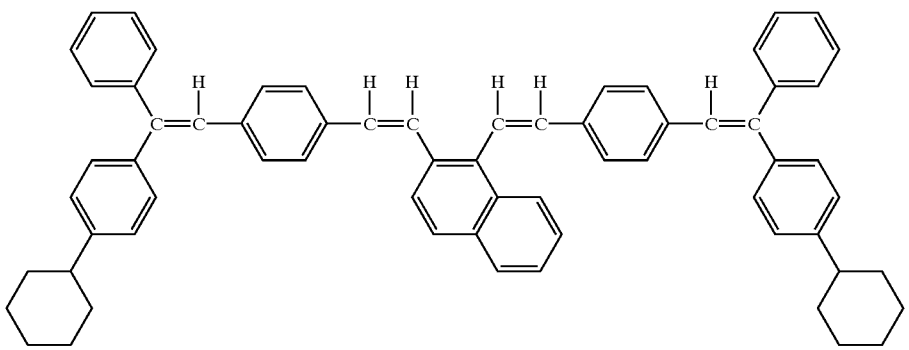 |
TABLE 2
| Compound No. | Structural Formula |
|---|---|
| 2-01 | 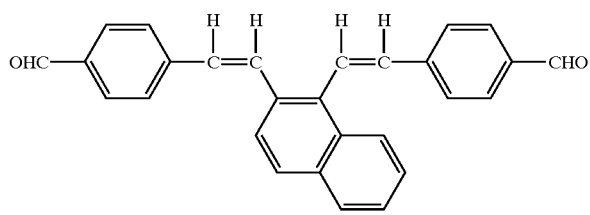 |
| 2-02 | 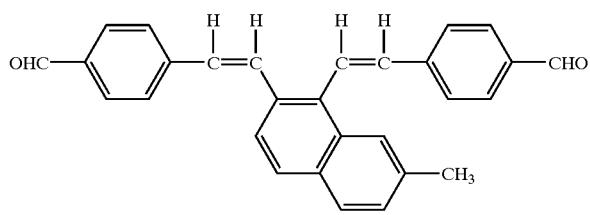 |
| 2-03 | 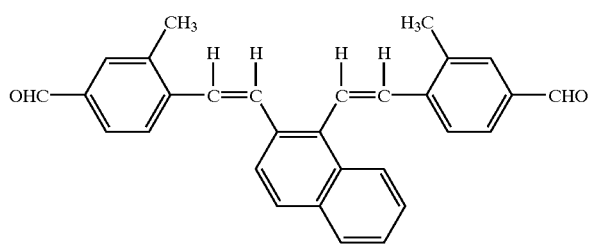 |
| 2-04 | 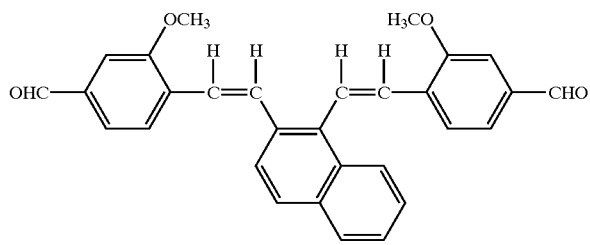 |

TABLE 3
| Compound No. | Structural Formula |
|---|---|
| 3-01 | 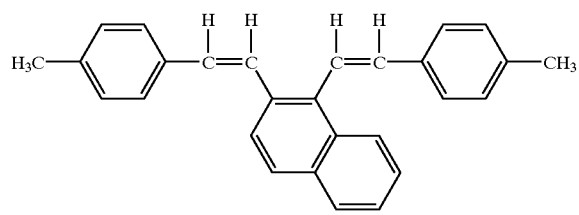 |
| 3-02 | 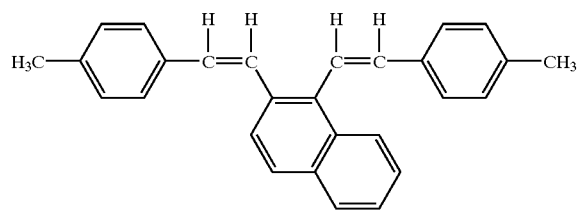 |
| 3-03 | 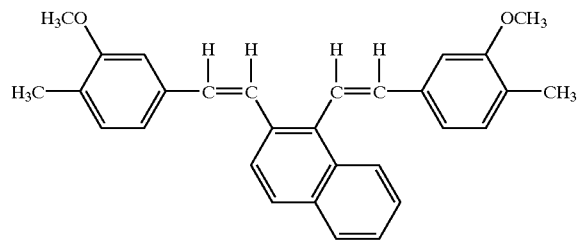 |
| 3-04 | 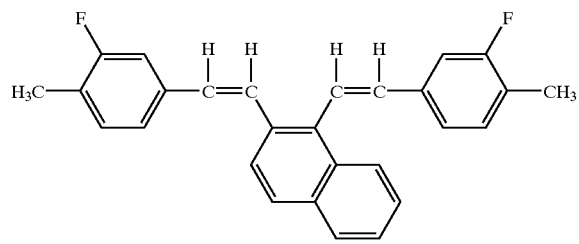 |
TABLE 1a
| Compound No. | Structural Formula |
|---|---|
| 1a-01 | 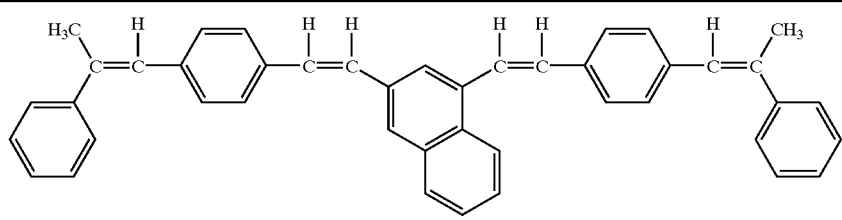 |
| 1a-02 | 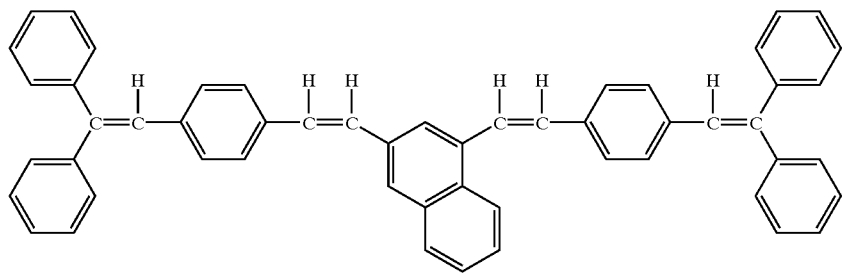 |

TABLE 1a-continued
| Compound No. | Structural Formula |
|---|---|
| 1a-03 | 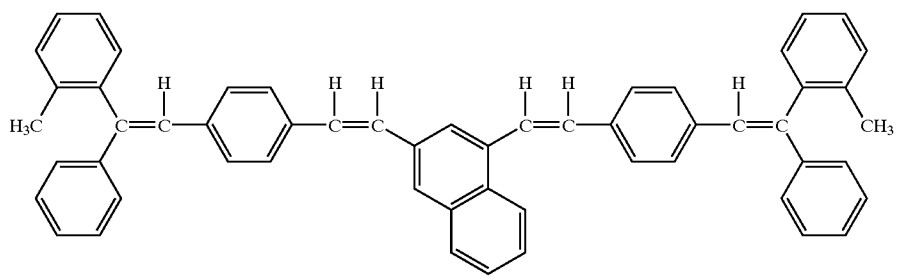 |
| 1-04 | 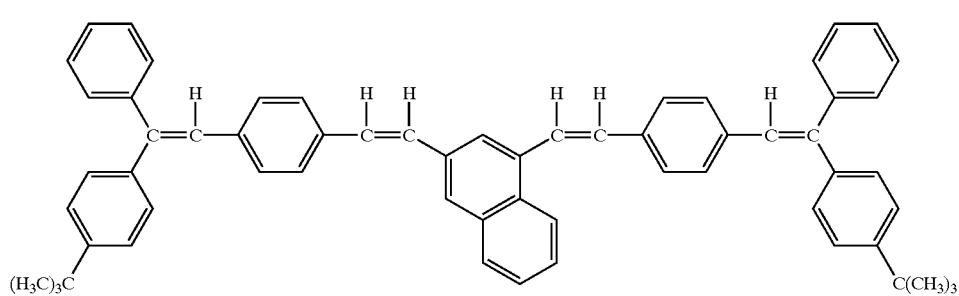 |
| 1a-05 | 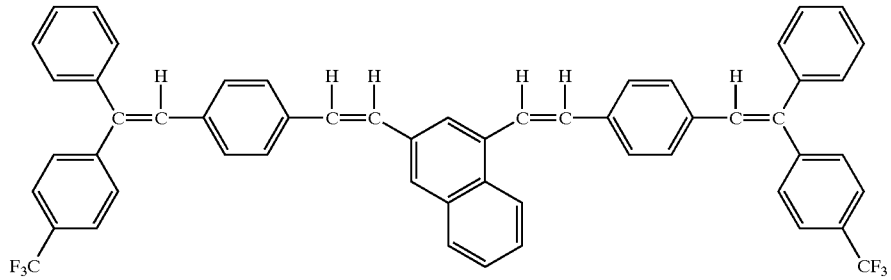 |
| 1a-06 | 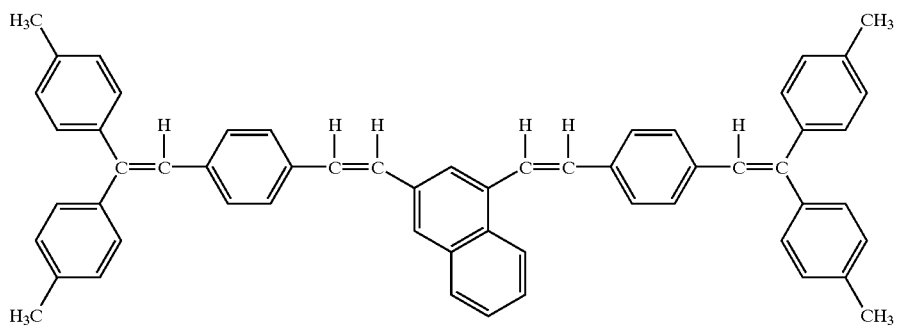 |

TABLE 1a-1
| Compound No. | Structural Formula |
|---|---|
| 1a-07 | 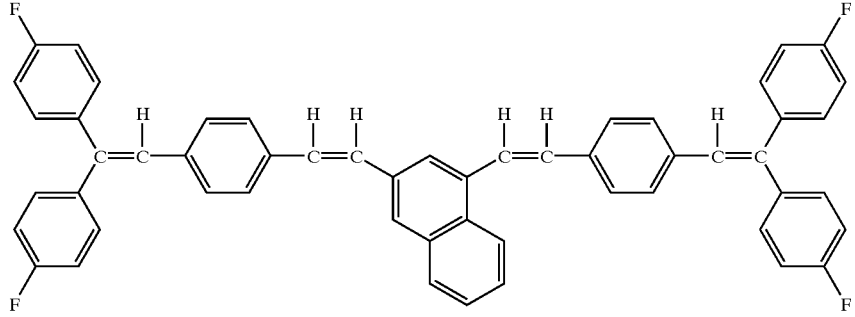 |
| 1a-08 | 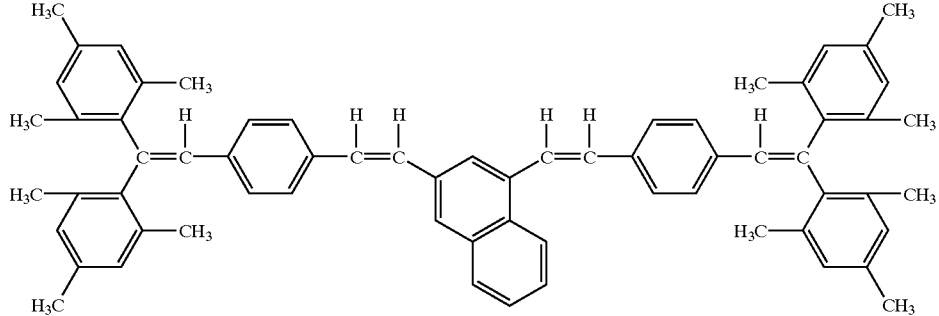 |
| 1a-09 | 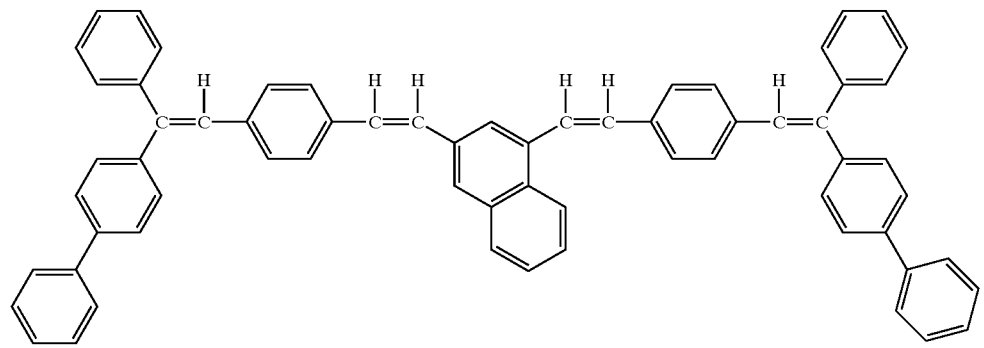 |
| 1a-10 | 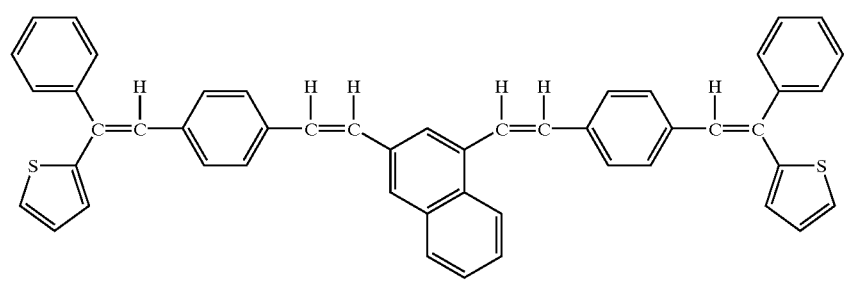 |
| 1a-11 | 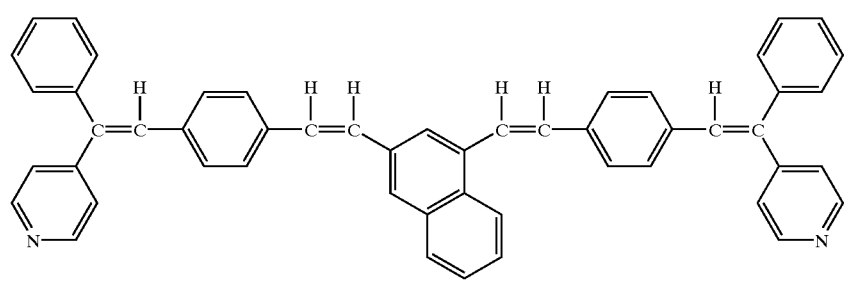 |

TABLE 1a-1-continued
| Compound No. | Structural Formula |
|---|---|
| 1a-12 | 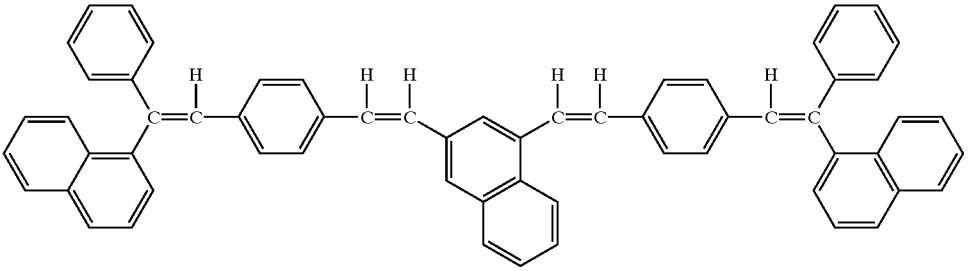 |
TABLE 1a-2
| Compound No. | Structural Formula |
|---|---|
| 1a-13 | 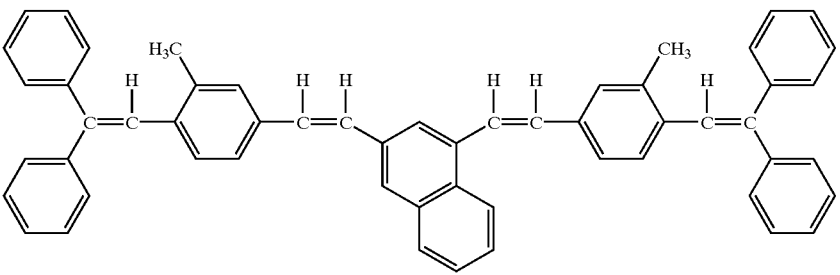 |
| 1a-14 | 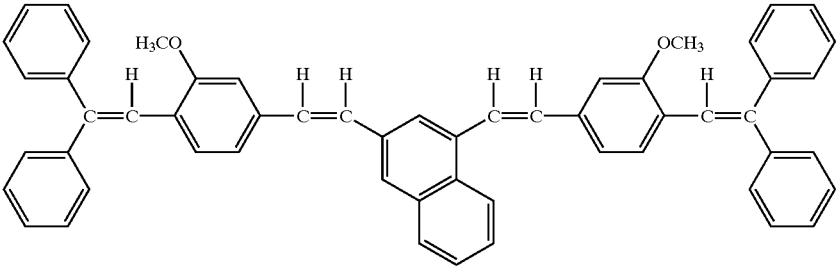 |
| 1a-15 | 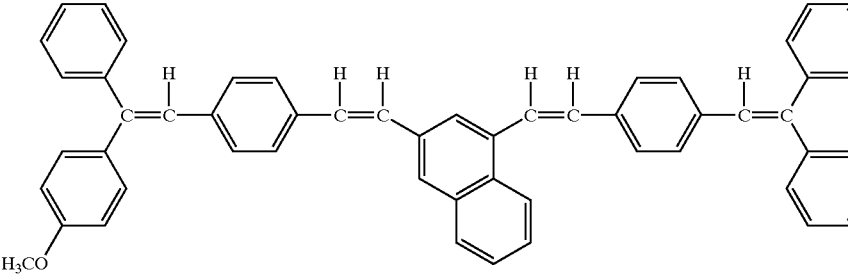 |
| 1a-16 | 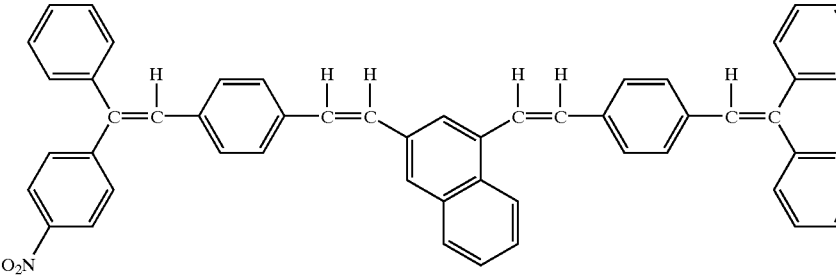 |

TABLE 1a-2-continued

| Compound No. | Structural Formula |
|---|---|
| 1a-17 | |
| 1a-18 | |

TABLE 1a-3

| Compound No. | Structural Formula |
|---|---|
| 1a-19 | |

TABLE 2a

| Compound No. | Structural Formula |
|---|---|
| 2a-01 | |

TABLE 2a-continued
| Compound No. | Structural Formula |
|---|---|
| 2a-02 | 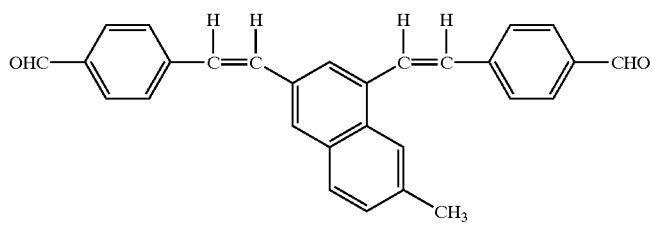 |
| 2a-03 | 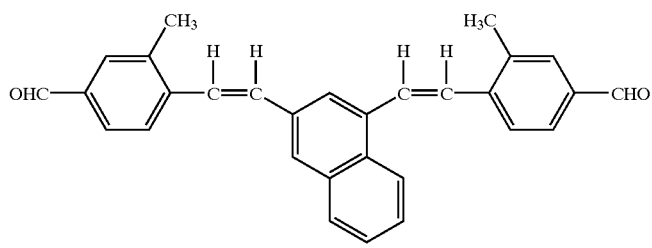 |
| 2a-04 | 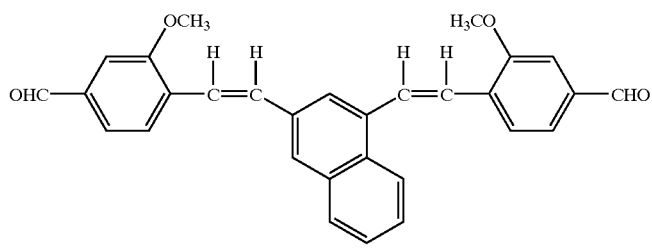 |
TABLE 3a
| Compound No. | Structural Formula |
|---|---|
| 3a-01 | 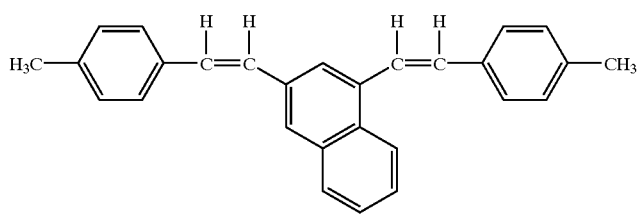 |
| 3a-02 | 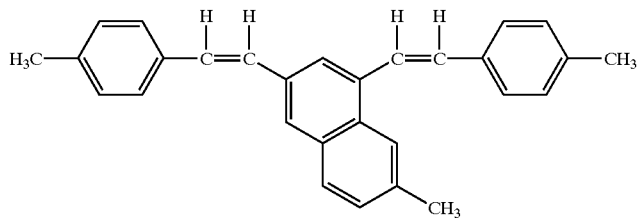 |
| 3a-03 | 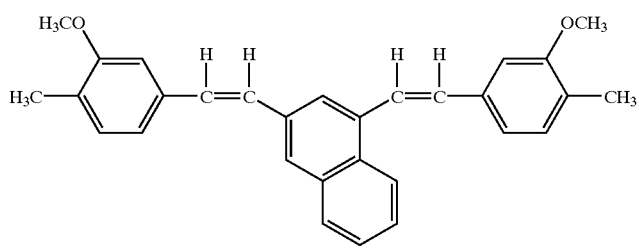 |

TABLE 3a-continued
| Compound No. | Structural Formula |
|---|---|
| 3a-04 | 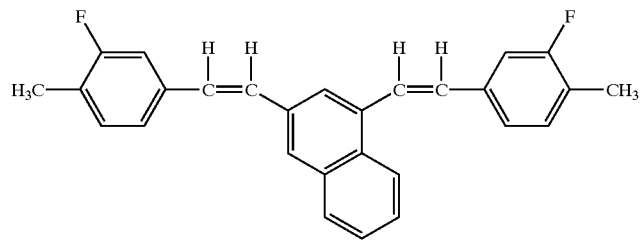 |
TABLE 1b
| Compound No. | Structural Formula |
|---|---|
| 1b-01 | 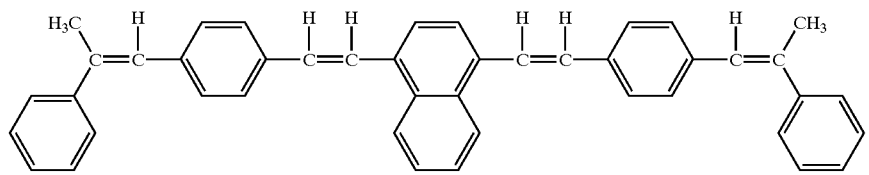 |
| 1b-02 | 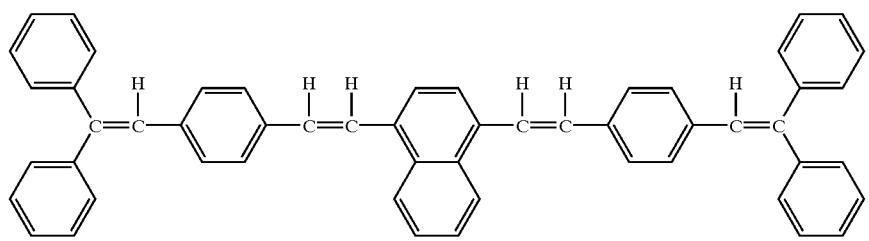 |
| 1b-03 | 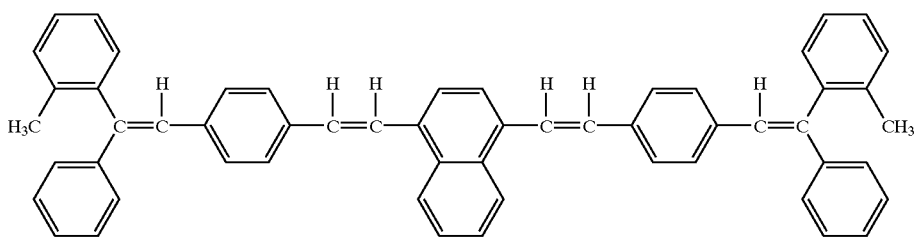 |
| 1b-04 | 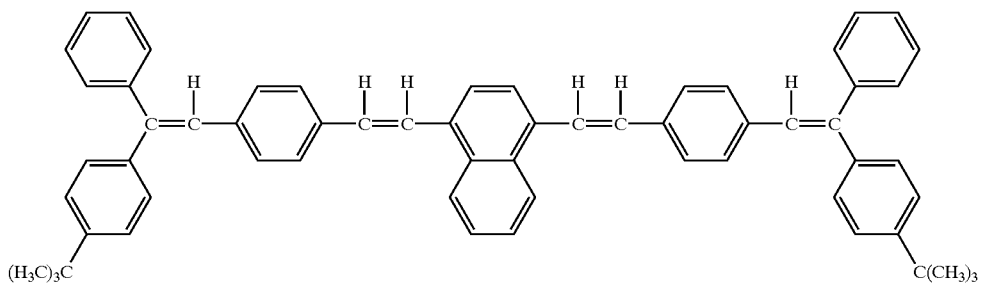 |

TABLE 1b-continued

| Compound No. | Structural Formula |
| --- | --- |
| 1b-05 | (structure) |
| 1b-06 | (structure) |
| 1b-07 | (structure) |

TABLE 1b-1

| Compound No. | Structural Formula |
| --- | --- |
| 1b-08 | (structure) |

TABLE 1b-1-continued

| Compound No. | Structural Formula |
|---|---|
| 1b-09 | |
| 1b-10 | |
| 1b-11 | |
| 1b-12 | |
| 1b-13 | |

TABLE 1b-2

| Compound No. | Structural Formula |
| --- | --- |
| 1b-14 | |
| 1b-15 | |
| 1b-16 | |
| 1b-17 | |
| 1b-18 | |

TABLE 1b-2-continued
| Compound No. | Structural Formula |
|---|---|
| 1b-19 | 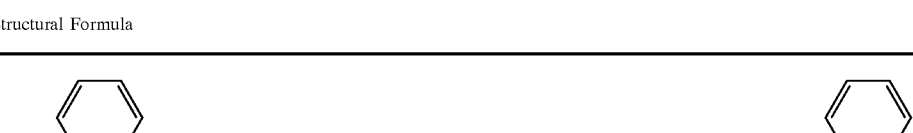 |
TABLE 2b
| Compound No. | Structural Formula |
|---|---|
| 2b-01 | |
| 2b-02 | |
| 2b-03 | |
| 2b-04 | |

TABLE 3b

| Compound No. | Structural Formula |
|---|---|
| 3b-01 | (structure) |
| 3b-02 | (structure) |
| 3b-03 | (structure) |
| 3b-04 | (structure) |

TABLE 1c

| Compound No. | Structural Formula |
|---|---|
| 1c-01 | (structure) |
| 1c-02 | (structure) |

TABLE 1c-continued

| Compound No. | Structural Formula |
|---|---|
| 1c-03 | |
| 1c-04 | |
| 1c-05 | |
| 1c-06 | |
| 1c-07 | |

TABLE 1c
| Compound No. | Structural Formula |
|---|---|
| 1c-08 | 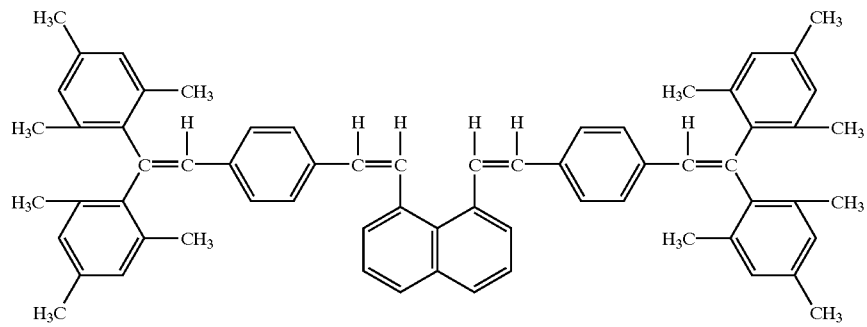 |
| 1c-09 | 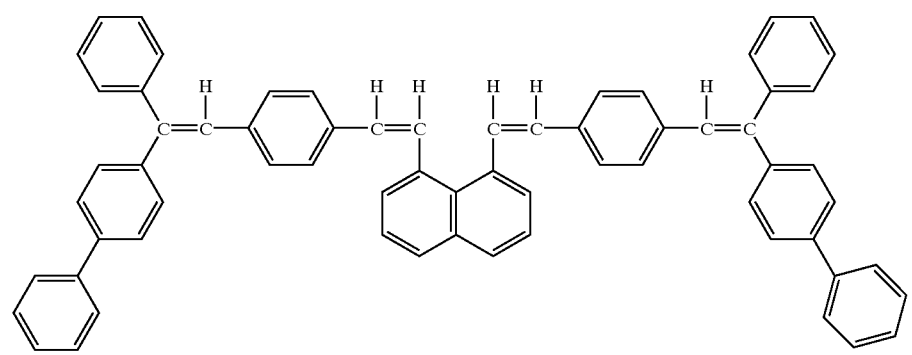 |
| 1c-10 | 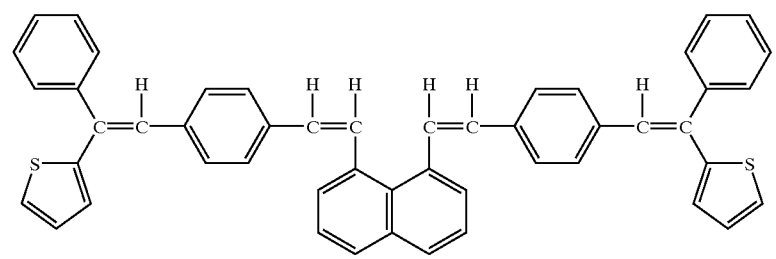 |
| 1c-11 | 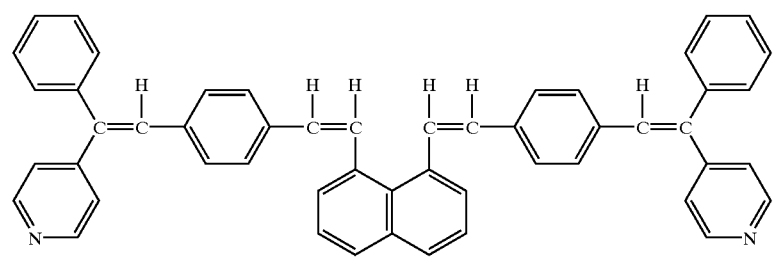 |
| 1c-12 | 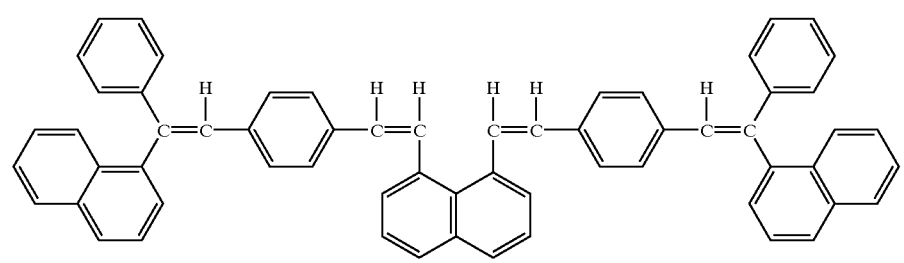 |

TABLE 1c-continued
| Compound No. | Structural Formula |
|---|---|
| 1c-13 | 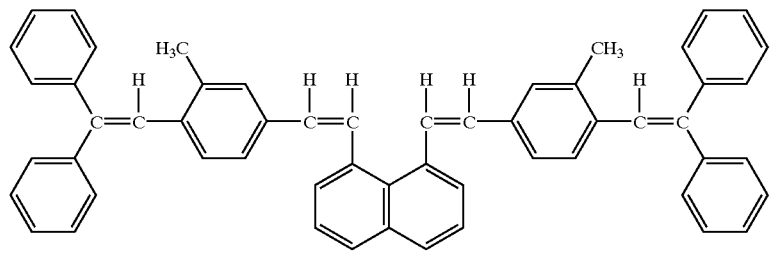 |
TABLE 1c
| Compound No. | Structural Formula |
|---|---|
| 1c-14 | 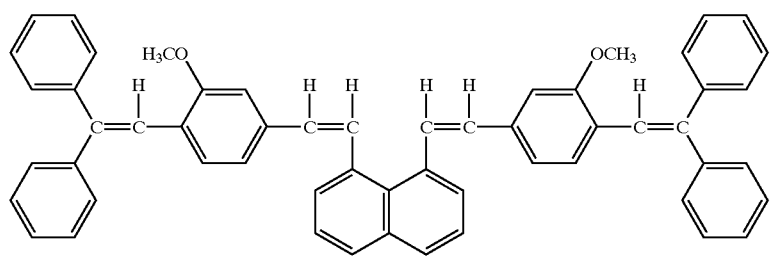 |
| 1c-15 | 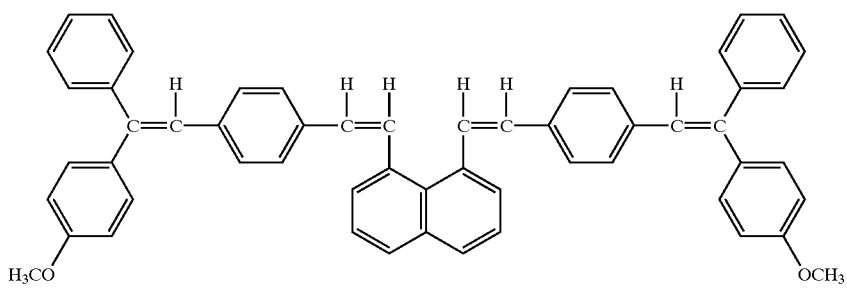 |
| 1c-16 | 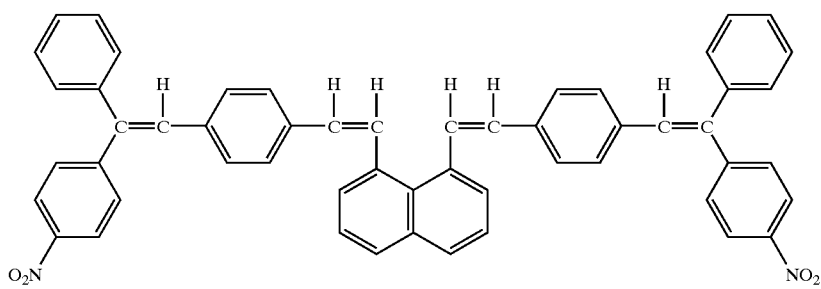 |
| 1c-17 | 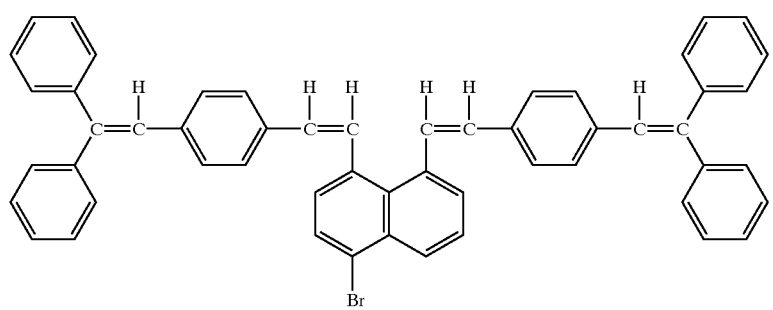 |

TABLE 1c-continued
| Compound No. | Structural Formula |
| --- | --- |
| 1c-18 | 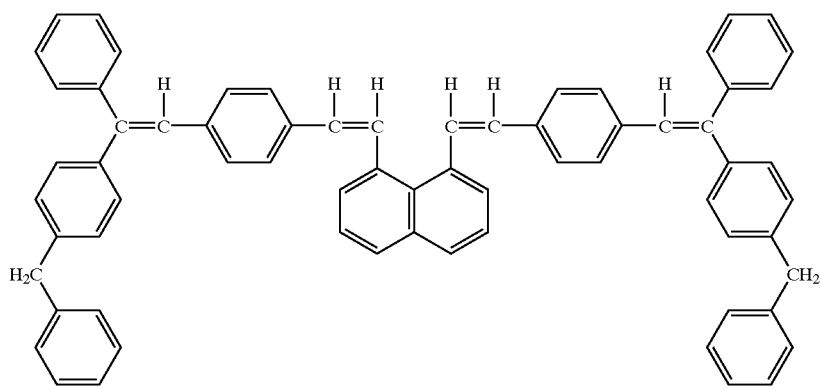 |
| 1c-19 | 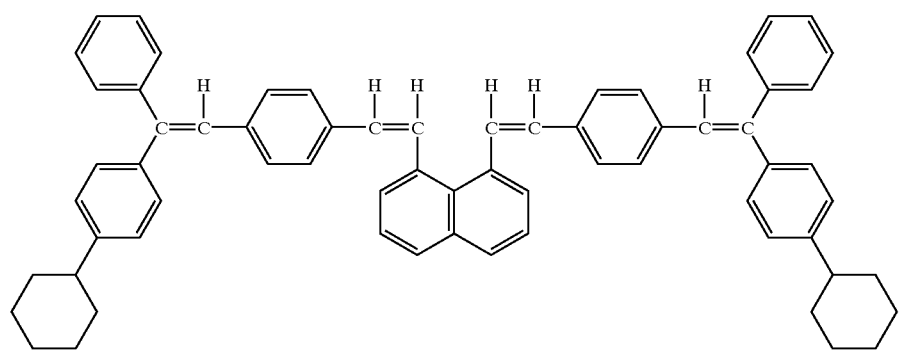 |
TABLE 2c
| Compound No. | Structural Formula |
| --- | --- |
| 2c-01 | 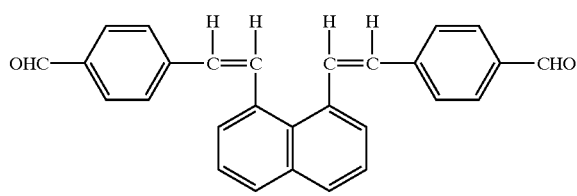 |
| 2c-02 | 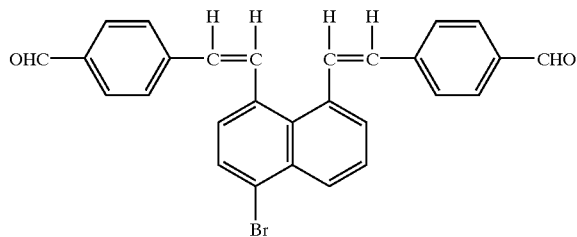 |
| 2c-03 | 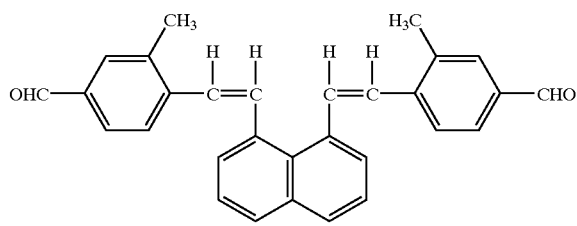 |

TABLE 2c-continued

| Compound No. | Structural Formula |
|---|---|
| 2c-04 | (1,8-naphthalene bis-styryl with 3-methoxy-4-formylphenyl groups) |

TABLE 3c

| Compound No. | Structural Formula |
|---|---|
| 3c-01 | (1,8-naphthalene bis-styryl with 4-methylphenyl groups) |
| 3c-02 | (4-bromo-1,8-naphthalene bis-styryl with 4-methylphenyl groups) |
| 3c-03 | (1,8-naphthalene bis-styryl with 3-methoxy-4-methylphenyl groups) |
| 3c-04 | (1,8-naphthalene bis-styryl with 3-fluoro-4-methylphenyl groups) |

TABLE 1d

| Compound No. | Structural Formula |
|---|---|
| 1d-01 | |
| 1d-02 | |
| 1d-03 | |
| 1d-04 | |
| 1d-05 | |

TABLE 1d-continued

| Compound No. | Structural Formula |
|---|---|
| 1d-06 | |

TABLE 1d-1

| Compound No. | Structural Formula |
|---|---|
| 1d-07 | |
| 1d-08 | |
| 1d-09 | |

TABLE 1d-1-continued

| Compound No. | Structural Formula |
| --- | --- |
| 1d-10 | |
| 1d-11 | |
| 1d-12 | |

TABLE 1d-2

| Compound No. | Structural Formula |
| --- | --- |
| 1d-13 | |

TABLE 1d-2-continued

| Compound No. | Structural Formula |
| --- | --- |
| 1d-14 | |
| 1d-15 | |
| 1d-16 | |
| 1d-17 | |

TABLE 1d-2-continued
| Compound No. | Structural Formula |
|---|---|
| 1d-18 | 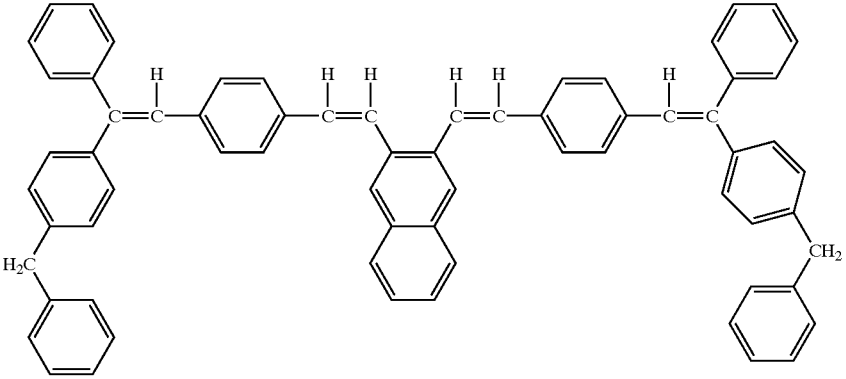 |
TABLE 1d
| Compound No. | Structural Formula |
|---|---|
| 1d-19 | 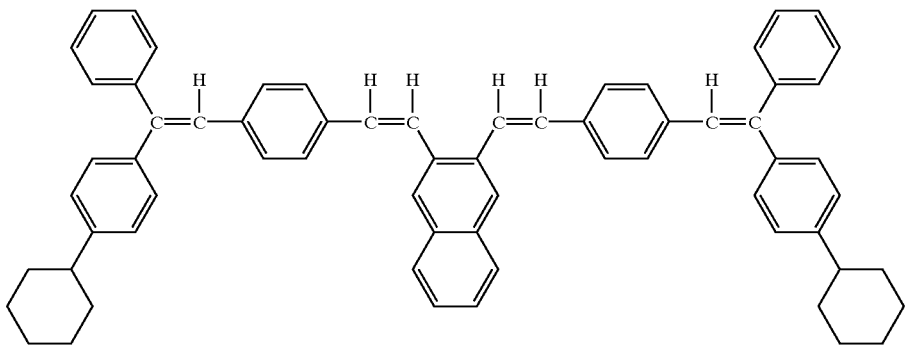 |
TABLE 2d
| Compound No. | Structural Formula |
|---|---|
| 2d-01 | 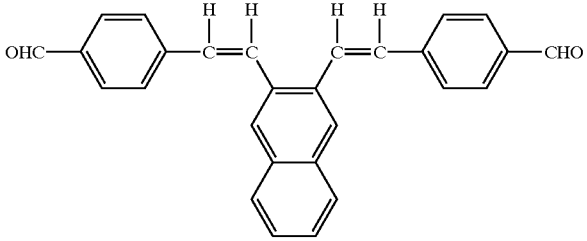 |
| 2d-02 | 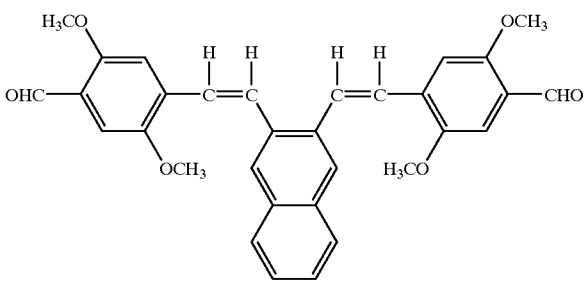 |

TABLE 2d-continued
| Compound No. | Structural Formula |
|---|---|
| 2d-03 | 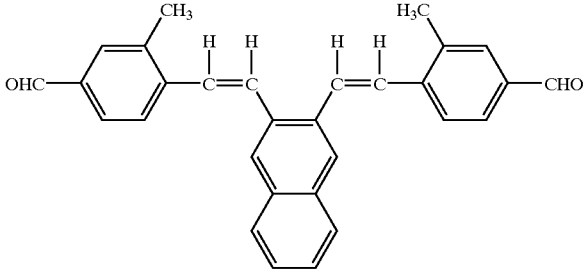 |
| 2d-04 | 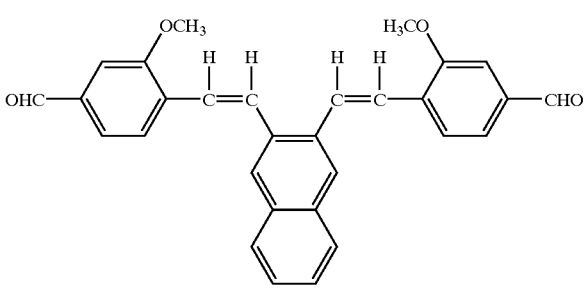 |
TABLE 3d
| Compound No. | Structural Formula |
|---|---|
| 3d-01 | 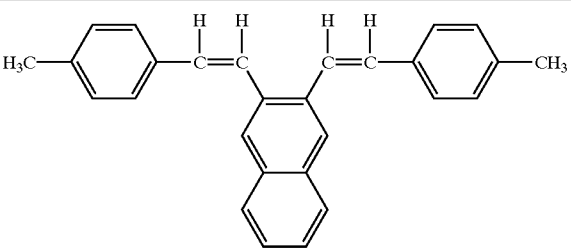 |
| 3d-02 | 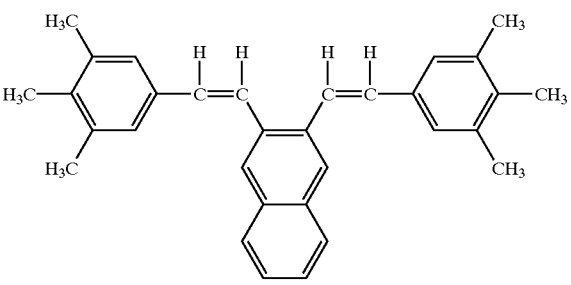 |
| 3d-03 | 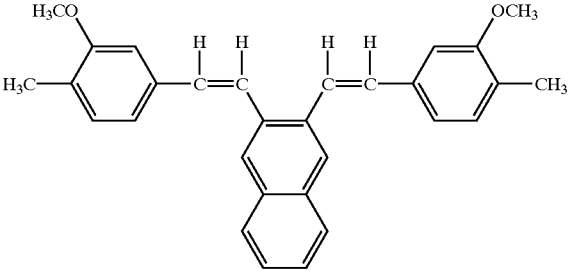 |

TABLE 3d-continued

| Compound No. | Structural Formula |
| --- | --- |
| 3d-04 | 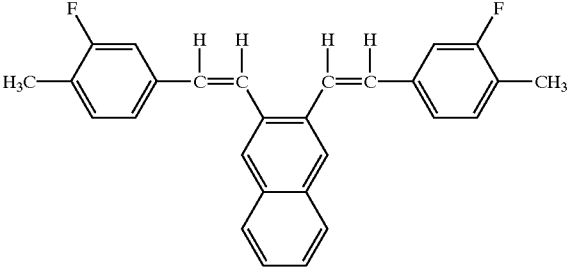 |

The compounds of the general formulas (1) to (1d) (e.g. Compound Nos. 1-01-1-19 to 1d-01-1d-19 indicated above) are useful as a constituent material for electroluminescent device, particularly as a light-emitting material.

In the general formula (1), it is preferred that $n^{11}$ and $n^{21}$ are, respectively, zero. It is also preferred that $R^{31}$ and $R^{41}$ are, respectively, phenyl. More preferably, $n^{11}$ and $n^{21}$ are, respectively, zero and $R^{31}$ and $R^{41}$ are, respectively, phenyl. Moreover, of the above-indicated specific compounds, the compound No. 1-02 of the following formula is most preferred from the standpoint of electroluminescent characteristics:

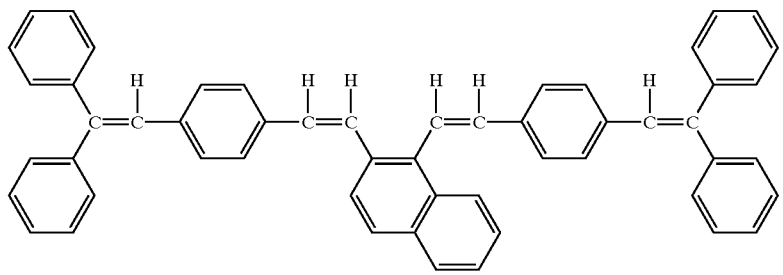

The compounds of the general formulas (2) to (2d) (e.g. Compound Nos. 2-01 to 2-04 to 2d-01 to 2d-04 and 3-01 to 3-04 to 3d-01 to 3d-04 indicated above) are, respectively, intermediates for preparing the compounds of the general formulas (1) to (1d). When using the compounds of the general formulas (1) to (1d), there can be obtained an organic electroluminescent device which exhibits high luminance and high durability.

The invention is more particularly described by way of examples, which should not be construed as limiting the invention thereto.

EXAMPLE 1

Preparation 1 of Compound No. 1-02

2.14 g of tetraethyl 1,2-dimethylnaphthalene-α,α'-diyldiphosphonate and 2.84 g of 4'-formyl-α-phenylstilbene were dissolved in 30 ml of N,N-dimethylformamide, to which 1.30 g of potassium tert-butoxide was added portion by portion over 10 minutes at 5 to 10° C. Thereafter, the resulting mixture was agitated at room temperature for 20 hours, to which 80 ml of ethanol was added. The resultant crystals were removed by filtration, washed with water and dried to obtain 2.53 g of yellow crystals.

Next, the yellow crystals were subjected to column chromatography using a stationary phase of silica gel and a mobile phase made of a mixed solvent of toluene and hexane (at a ratio by volume of 1:1), thereby obtaining a yellow, vitreous substance. Further, this yellow vitreous substance was again subjected to column chromatograph using silica gel as a stationary phase and a mixed solvent of toluene and hexane (with a ratio by volume of 1:2) as a mobile phase, thereby obtaining 2.38 g of a yellow vitreous substance.

Subsequently, the substance was recrystallized from a mixed solvent of chloroform and ethanol and vacuum dried at 100° C. to obtain 2.29 g of yellow crystals having intense fluorescence at a yield of 67%. The crystals had a melting point of 181.5 to 185° C.

The elemental analysis of the crystals revealed that carbon was found at 94.10% (94.15%, calculated for compound No. 1-02) and hydrogen was found at 5.82% (5.85%, calculated for compound No. 1-02). The infrared absorption spectral chart of the crystals (determined by a KBr tablet method) is shown in FIG. 1, from which the stretch vibrations ascribed to the aromatic rings are observed in the vicinity of 1600 $cm^{-1}$. The crystals were subjected to the analysis of proton nuclear magnetic resonance (using a solvent of $CDCl_3$ and an internal standard of TMS (tetramethylsilane), revealing that the proton of the aromatic rings and the proton of the alkene were found at δ=6.7 to 8.1 ppm (40H).

With the mass spectra of the crystals, the molecular ion peak was observed at m/z=688. From the results of the above analyses, the crystals were identified as Compound No. 1-02.

EXAMPLE 2

Preparation 2 of Compound No. 1-02

3.04 g of diethyl diphenylmethylphosphate and 1.94 g of 1,2-bis((4-formylstyryl)naphthalene (compound No. 2-01)

were dissolved in 30 ml of N,N-dimethylformamide, to which 1.30 g of potassium tert-butoxide was added portion by portion over 10 minutes at 5 to 10° C. Thereafter, the resulting mixture was agitated at room temperature for 20 hours, to which 80 ml of ethanol was added. The resultant crystals were removed by filtration, washed with water and dried to obtain 2.00 g of yellow crystals.

Next, the yellow crystals were subjected, in the same manner as in Example 1, to column chromatography using a stationary phase of silica gel and a mobile phase of a mixed solvent of toluene and hexane (at a ratio by volume of 1:1), thereby obtaining a yellow, vitreous substance. Further, this yellow vitreous substance was again subjected to column chromatograph using silica gel as a stationary phase and a mixed solvent of toluene and hexane (with a ratio by volume of 1:2) as a mobile phase, thereby obtaining 1.67 g of a yellow vitreous substance.

Subsequently, the substance was recrystallized from a mixed solvent of chloroform and ethanol and vacuum dried at 100° C. to obtain 1.58 g of yellow crystals having intense fluorescence at a yield of 46%. The crystals had a melting point of 181.5 to 185° C.

The elemental analysis of the crystals revealed that carbon was found at 94.05% (94.15%, calculated for compound No. 1-02) and hydrogen was found at 5.73% (5.85%, calculated for compound No. 1-02). The infrared absorption spectra, nuclear magnetic resonance spectra and mass spectra were, respectively, coincident with those of the compound obtained in Example 1, demonstrating that both compounds were identical to each other and were identified as compound No. 1-02.

EXAMPLE 3

Preparation 3 of Compound No. 1-02

0.921 g of 1,2-naphthalene dicarbaldehyde and 4.06 g of diethyl 4-(2,2'-diphenylvinyl)benzylphosphonate were dissolved in 30 ml of N,N-dimethylformamide, to which 1.30 g of potassium tert-butoxide was added portion by portion over 10 minutes at 5 to 10° C. Thereafter, the resulting mixture was agitated at room temperature for 20 hours, to which 80 ml of ethanol was added. The resultant crystals were removed by filtration, washed with water and dried to obtain 2.23 g of yellow crystals.

Next, the yellow crystals were subjected, in the same manner as in Example 1, to column chromatography using a stationary phase of silica gel and a mobile phase of a mixed solvent of toluene and hexane (at a ratio by volume of 1:1), thereby obtaining a yellow, vitreous substance. Further, this yellow vitreous substance was again subjected to column chromatograph using silica gel as a stationary phase and a mixed solvent of toluene and hexane (with a ratio by volume of 1:2) as a mobile phase, thereby obtaining 1.91 g of a yellow vitreous substance.

Subsequently, the substance was recrystallized from a mixed solvent of chloroform and ethanol and vacuum dried at 100° C. to obtain 1.60 g of yellow crystals having intense fluorescence at a yield of 47%. The crystals had a melting point of 181.5 to 185° C.

The elemental analysis of the crystals revealed that carbon was found at 94.00% (94.15%, calculated for compound No. 1-02) and hydrogen was found at 5.69% (5.85%, calculated for compound No. 1-02). The infrared absorption spectra, nuclear magnetic resonance spectra and mass spectra were, respectively, coincident with those of the compound obtained in Example 1, demonstrating that both compounds were identical to each other and were identified as compound No. 1-02.

EXAMPLE 4

Preparation 4 of Compound No. 1-02

1.82 g of benzophenone and 3.16 g of tetraethyl 1,2-bis (4-methylstyryl)naphthalene-α,α'-diyldiphosphonate were dissolved in 30 ml of N,N-dimethylformamide, to which 1.30 g of potassium tert-butoxide was added portion by portion over 10 minutes at 5 to 10° C. Thereafter, the resulting mixture was agitated at room temperature for 20 hours, to which 80 ml of ethanol was added. The resultant crystals were removed by filtration, washed with water and dried to obtain 1.90 g of yellow crystals.

Next, the yellow crystals were subjected, in the same manner as in Example 1, to column chromatography using a stationary phase of silica gel and a mobile phase of a mixed solvent of toluene and hexane (at a ratio by volume of 1:1), thereby obtaining a yellow, vitreous substance. Further, this yellow vitreous substance was again subjected to column chromatograph using silica gel as a stationary phase and a mixed solvent of toluene and hexane (with a ratio by volume of 1:2) as a mobile phase, thereby obtaining 1.64 g of a yellow vitreous substance.

Subsequently, the substance was recrystallized from a mixed solvent of chloroform and ethanol and vacuum dried at 100° C. to obtain 1.33 g of yellow crystals having intense fluorescence at a yield of 39%. The crystals had a melting point of 181.5 to 185° C.

The elemental analysis of the crystals revealed that carbon was found at 94.03% (94.15%, calculated for compound No. 1-02) and hydrogen was found at 5.75% (5.85%, calculated for compound No. 1-02). The infrared absorption spectra, nuclear magnetic resonance spectra and mass spectra were, respectively, coincident with those of the compound obtained in Example 1, demonstrating that both compounds were identical to each other and were identified as compound No. 1-02.

EXAMPLE 5

Preparation 1 of Compound No. 2-01

8.57 g of tetraethyl 1,2-dimethylnaphthalene-α,α'-diyldiphosphonate and 8.75 g of terephthalaldehyde mono-diethylacetal were dissolved in 80 ml of N,N-dimethylformamide, to which 5.67 g of potassium tert-butoxide was added portion by portion over 10 minutes at 5 to 10° C. Thereafter, the resulting mixture was agitated at room temperature for 25 hours, to which 38.5 ml of 36% hydrochloric acid was added, followed by further agitation on a bath at a temperature of 80 to 85° C. for 30 minutes. After standing the reaction mixture to cool, about 150 ml of water was added thereto, and the resultant crystals were removed by filtration, washed with water and vacuum dried at 60° C. to obtain 7.27 g of yellow crystals.

The thus obtained yellow crystals were recrystallized from a mixed solvent of toluene and ethanol (at a ratio by volume of 1:1) and vacuum dried at 80° C., thereby obtaining 5.98 g of yellow needle crystals at a yield of 77% with a melting point of 168.6 to 171.5° C.

The elemental analysis of the crystals revealed that carbon was found at 86.44% (86.57%, calculated for compound No. 2-01) and hydrogen was found at 5.04% (5.19%, calculated for compound No. 2-01). The infrared absorption spectral chart (determined by a KBr tablet method) is shown in FIG.

2, revealing stretch vibrations ascribed to the aldehyde in the vicinity of 1690 cm$^{-1}$ and stretch vibrations ascribed to the aromatic rings in the vicinity of at 1595 cm$^{-1}$. From the results of proton nuclear magnetic resonance spectroscopy (using DMSO (dimethyl sulfoxide)-d$_6$ as a solvent and TMS as an internal standard), the proton of the aldehyde was recognized at δ=10.00 ppm (1H) and δ=10.1 ppm (1H) and the protons of the aromatic rings and alkene were recognized at δ=6.8 to 8.3 ppm (18H).

Moreover, with mass spectra, the molecular ion peak was observed at m/z=388. From the foregoing, the compound obtained was identified as compound No. 2-01.

EXAMPLE 6

Preparation 2 of Compound No. 2-01

8.57 g of tetraethyl 1,2-dimethylnaphthalene-α,α'-diyldiphosphonate and 13.41 g of terephthalaldehyde were dissolved in 160 ml of N,N-dimethylformamide, to which 5.67 g of potassium tert-butoxide was added portion by portion over 10 minutes at 5 to 10° C. Thereafter, the resulting mixture was agitated at room temperature for 20 hours, to which about 300 ml of water was added. The resultant crystals were removed by filtration, washed with water, and further washed with 200 ml of hot ethanol to obtain 6.85 g of yellow powder.

The thus obtained yellow powder was repeatedly recrystallized from a mixed solvent of toluene and ethanol (at a ratio by volume of 1:1) and vacuum dried at 80° C., thereby obtaining 1.28 g of yellow needle crystals with a melting point of 168.5 to 171.5° C. at a yield of 16%.

The elemental analysis of the crystals revealed that carbon was found at 86.40% (86.57%, calculated for compound No. 2-01) and hydrogen was found at 5.00% (5.19%, calculated for compound No. 2-01). The infrared absorption spectra, nuclear magnetic resonance spectra and mass spectra were, respectively, coincident with those of the compound obtained in Example 5, demonstrating that both compounds were identical to each other as compound No. 2-01.

EXAMPLE 7

Preparation 1 of Compound No. 3-01

4.28 g of tetraethyl 1,2-dimethylnaphthalene-α,α'-diyldiphosphonate and 2.64 g of 4-methylbenzaldehyde were dissolved in 60 ml of N,N-dimethylformamide, to which 2.60 g of potassium tert-butoxide was added portion by portion over 10 minutes at 5 to 10° C. Thereafter, the resulting mixture was agitated at room temperature for 20 hours, to which about 150 ml of water was added. The resulting crystals were removed by filtration, washed with water and vacuum dried to obtain 3.41 g of light brown powder.

Figure 3:
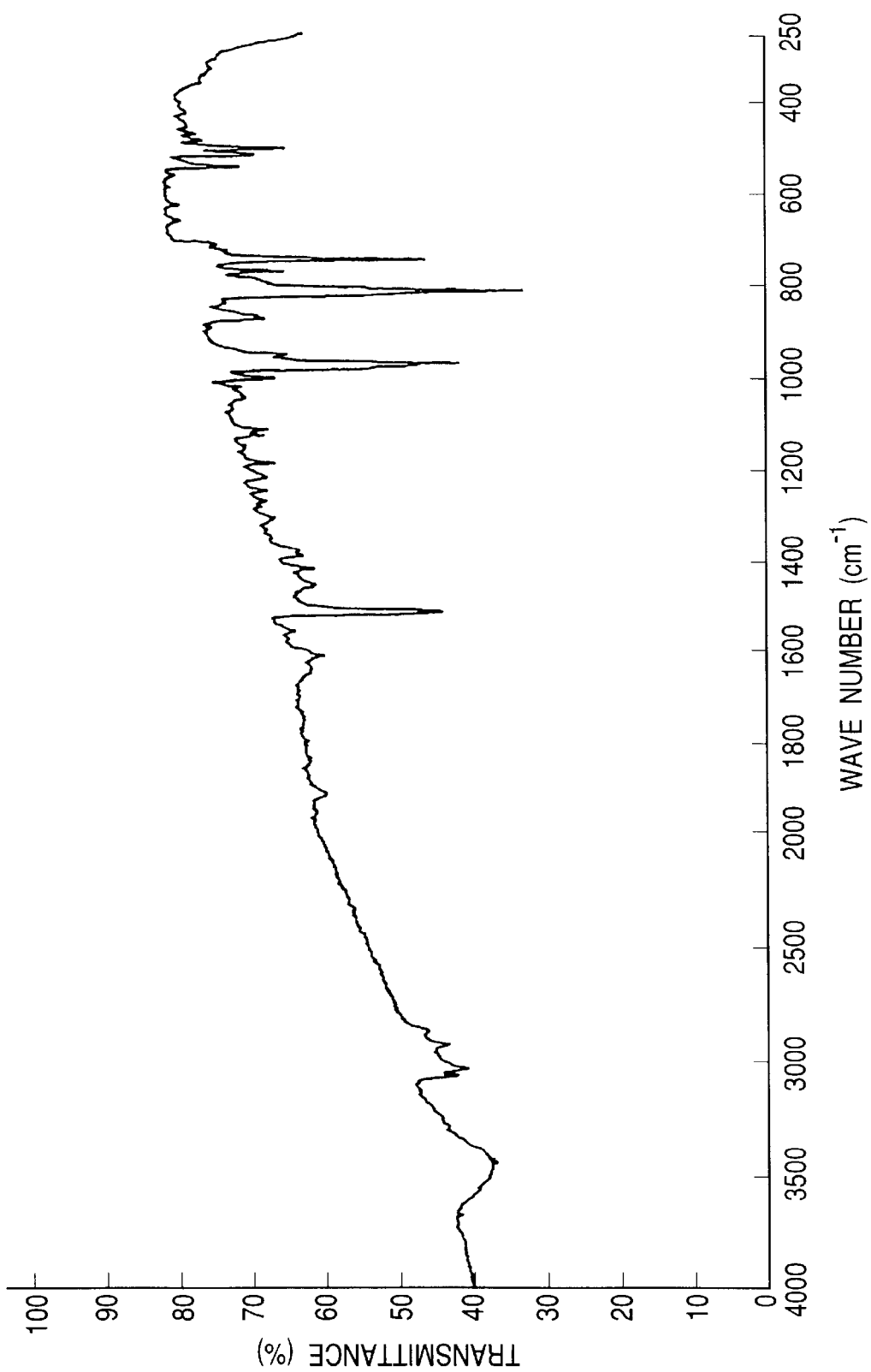
FIG. 3 is a spectrogram showing infrared absorption spectra of compound No. 3-01 according to the invention.

The thus obtained powder was recrystallized from about 500 ml of ethanol to obtain 2.09 g of light yellow needle crystals at a yield of 58% with a melting point of 161.5 to 163.0° C. The elemental analysis of the crystals revealed that carbon was found at 93.18% (93.29%, calculated for compound No. 3-01) and hydrogen was found at 6.55% (6.71%, calculated for compound No. 3-01). The infrared absorption spectral chart (determined by a KBr tablet method) is shown in FIG. 3, revealing stretch vibrations ascribed to the aromatic rings in the vicinity of 1510 and 1605 cm$^{-1}$. From the results of proton nuclear magnetic resonance spectroscopy (using CDCl$_3$ as a solvent and TMS as an internal standard), the proton of the methyl group was recognized at δ=2.3 ppm (3H) and δ=2.4 ppm (3H) and the protons of the aromatic rings and alkene were recognized at δ=6.8 to 8.2 ppm (18H).

With mass spectra, the molecular ion peak was observed at m/z=360. From the foregoing, the compound obtained was identified as compound No. 3-01.

EXAMPLE 8

Preparation 2 of Compound 3-01

1.84 g of 1,2-naphthalene dicarbaldehyde and 4.85 g of diethyl 4-methylbenzylphosphonate were dissolved in 60 ml of N,N-dimethylformamide, to which 2.60 g of potassium tert-butoxide was added portion by portion over 10 minutes at 5 to 10° C. Thereafter, the resulting mixture was agitated at room temperature for 20 hours, to which about 150 ml of water was added. The resulting crystals were removed by filtration, washed with water and vacuum dried to obtain 3.20 g of light brown powder.

The thus obtained powder was recrystallized from about 500 ml of ethanol to obtain 1.98 g of light yellow needle crystals at a yield of 55% with a melting point of 161.5 to 163.0° C. The elemental analysis of the crystals revealed that carbon was found at 93.14% (93.29%, calculated for compound No. 3-01) and hydrogen was found at 6.62% (6.71%, calculated for compound No. 3-01).

The infrared absorption spectra, nuclear magnetic resonance spectra and mass spectra were, respectively, coincident with those of the compound obtained in Example 7, demonstrating that both compounds were identical to each other and were identified as compound No. 3-01

EXAMPLE 9

Preparation of Compound No. 1-03

1.91 g of diethyl (2-methylphenyl) phenylmethylphosphonate and 1.17 g of 1,2-bis(4-formylstyryl)naphthalene (corresponding to compound No. 2-01) were dissolved in 18 ml of N,N-dimethylformamide, to which 0.78 g of potassium tert-butoxide was added portion by portion over 10 minutes at 5 to 10° C. Thereafter, the resulting mixture was agitated at room temperature for 20 hours, and the reaction mixture was charged into about 100 ml of water. The resulting solid matter was removed by filtration, washed with water and dried to obtain 1.29 g of orangish yellow powder.

Next, this yellow powder was subjected to column chromatography using a stationary phase of silica gel and a mobile phase of a mixed solvent of toluene and hexane (at a ratio by volume of 1:1), thereby obtaining a yellow, vitreous substance. Further, this yellow vitreous substance was again subjected to column chromatograph using silica gel as a stationary phase and a mixed solvent of toluene and hexane (with a ratio by volume of 1:2) as a mobile phase, thereby obtaining 1.00 g of a yellow vitreous substance.

Subsequently, the substance was recrystallized from a mixed solvent of chloroform and ethanol and vacuum dried at 100° C. to obtain 0.86 g of yellow crystals having intense fluorescence at a yield of 40%. The elemental analysis of the crystals revealed that carbon was found at 93.70% (93.81%, calculated for compound No. 1-03) and hydrogen was found at 6.00% (6.19%, calculated for compound No. 1-03). The crystals were identified as compound No. 1-03 through the infrared absorption spectra, nuclear magnetic resonance spectra and mass spectra in the same manner as in forgoing examples.

EXAMPLE 10

Preparation of Compound No. 1-07

2.04 g of diethyl (4-fluorophenyl) phenylmethylphosphonate and 1.17 g of 1,2-bis(4- formylstyryl)naphthalene (corresponding to compound No. 2-01) were dissolved in 18 ml of N,N-dimethylformamide, to which 0.780 g of potassium tert-butoxide was added portion by portion over 10 minutes at 5 to 10° C. Thereafter, the resulting mixture was agitated at room temperature for 20 hours, and the reaction mixture was charged into about 100 ml of water. The resulting solid matter was removed by filtration, washed with water and dried to obtain 1.96 g of yellow powder.

Next, this yellow powder was subjected to column chromatography using a stationary phase of silica gel and a mobile phase of a mixed solvent of toluene and hexane (at a ratio by volume of 1:1), thereby obtaining a yellow, vitreous substance.

Further, this yellow vitreous substance was again subjected to column chromatograph using silica gel as a stationary phase and a mixed solvent of toluene and hexane (with a ratio by volume of 1:2) as a mobile phase, thereby obtaining 1.43 g of a yellow vitreous substance. Subsequently, the substance was recrystallized from a mixed solvent of chloroform and ethanol and vacuum dried at 100° C. to obtain 1.22 g of yellow crystals having intense fluorescence at a yield of 54%. The elemental analysis of the crystals revealed that carbon was found at 84.98% (85.24%, calculated for compound No. 1-07) and hydrogen was found at 4.50% (4.77%, calculated for compound No. 1-07).

The crystals were identified as compound No. 1-07 through the infrared absorption spectra, nuclear magnetic resonance spectra and mass spectra in the same manner as in forgoing examples.

EXAMPLE 11

An organic electroluminescent device was made in such a way that a hole transport layer, an emission layer, an electron transport layer and a cathode (aluminium/lithium (Al/Li)) were successively deposited by vacuum deposition on an electrode of a glass substrate wherein an indium tin oxide (ITO) thin film had been previously formed as a transparent electrode (i.e. an ITO glass substrate).

More particularly, the ITO glass substrate, N,N'-diphenyl-N,N'-bis(3-methylphenyl)benzidine (TPD) serving as a hole transport material, an aromatic methylidene compound corresponding to compound No. 1-02 of the invention and serving as a light-emitting material, and tris(8-hydroxyquinolino)aluminium (Alq) serving as an electron transport material) were, respectively, set in a vacuum deposition device, followed by evacuation to $10^{-4}$ Pa.

Next, TPD used as a hole transport material was vacuum deposited on the electrode of the ITO glass substrate at a rate of 0.1 to 0.5 nm/second, thereby forming a 50 nm thick hole transport layer. Thereafter, the compound No. 1-02 used as an emission material was vacuum deposited at a deposition rate of 0.1 to 0.5 nm/second to form a 50 nm thick emission layer. Alq used as an electron transport material was vacuum deposited at a rate of 0.1 nm/second to form a 10 nm thick electron transport layer. Moreover, Li and Al were simultaneously subjected to vacuum deposition at rates of 0.01 to 0.02 nm/second and 1 to 2 nm/second, respectively, thereby forming an Al/Li electrode with a thickness of 150 nm.

These depositions were continuously performed without breakage of vacuum, and the respective thicknesses were controlled by monitoring with a crystal oscillator. Immediately after making of the device, lead wires were attached to the respective electrodes in dry nitrogen to complete an organic electroluminescent device. When a voltage was applied to the device, uniform blue emission was obtained.

The emission spectrum has a peak wavelength at 483 nm. When a drive voltage and an emission luminance were measured by application of an electric current of 100 mA/cm$^2$, the drive voltage was found at 7.4V and the luminance was at 2500 cd/m$^2$.

Next, examples relating to the compounds of the general formulas (1a), (2a) and (3a) and the preparation thereof are described.

EXAMPLE 12

Preparation 1 of Compound No. 1a-02

0.857 g of tetraethyl 1,3-dimethylnaphthalene-α,α'-diyldiphosphonate and 1.14 g of 4'-formyl-α-phenylstilbene were dissolved in 12 ml of N,N-dimethylformamide, to which 0.520 g of potassium tert-butoxide was added portion by portion over 10 minutes at 5 to 10° C. Thereafter, the resulting mixture was agitated at room temperature for 20 hours, after which the reaction mixture was charged into about 150 ml of ethanol. The resultant precipitate was removed by filtration, washed with water and dried to obtain 1.33 g of light yellow powder.

Next, the light yellow powder was subjected to column chromatography using a stationary phase of silica gel and a mobile phase made of a mixed solvent of toluene and hexane (at a ratio by volume of 1:1), thereby obtaining a light yellow, vitreous substance. Further, this light yellow vitreous substance was again subjected to column chromatograph using silica gel as a stationary phase and a mixed solvent of toluene and hexane (with a ratio by volume of 1:2) as a mobile phase, thereby obtaining 1.26 g of a yellow vitreous substance.

Subsequently, the substance was recrystallized from a mixed solvent of chloroform and ethanol and vacuum dried at 100° C. to obtain 1.17 g of light yellow crystals having intense fluorescence at a yield of 85%. The crystals had a melting point of 180° C.

Figure 4:
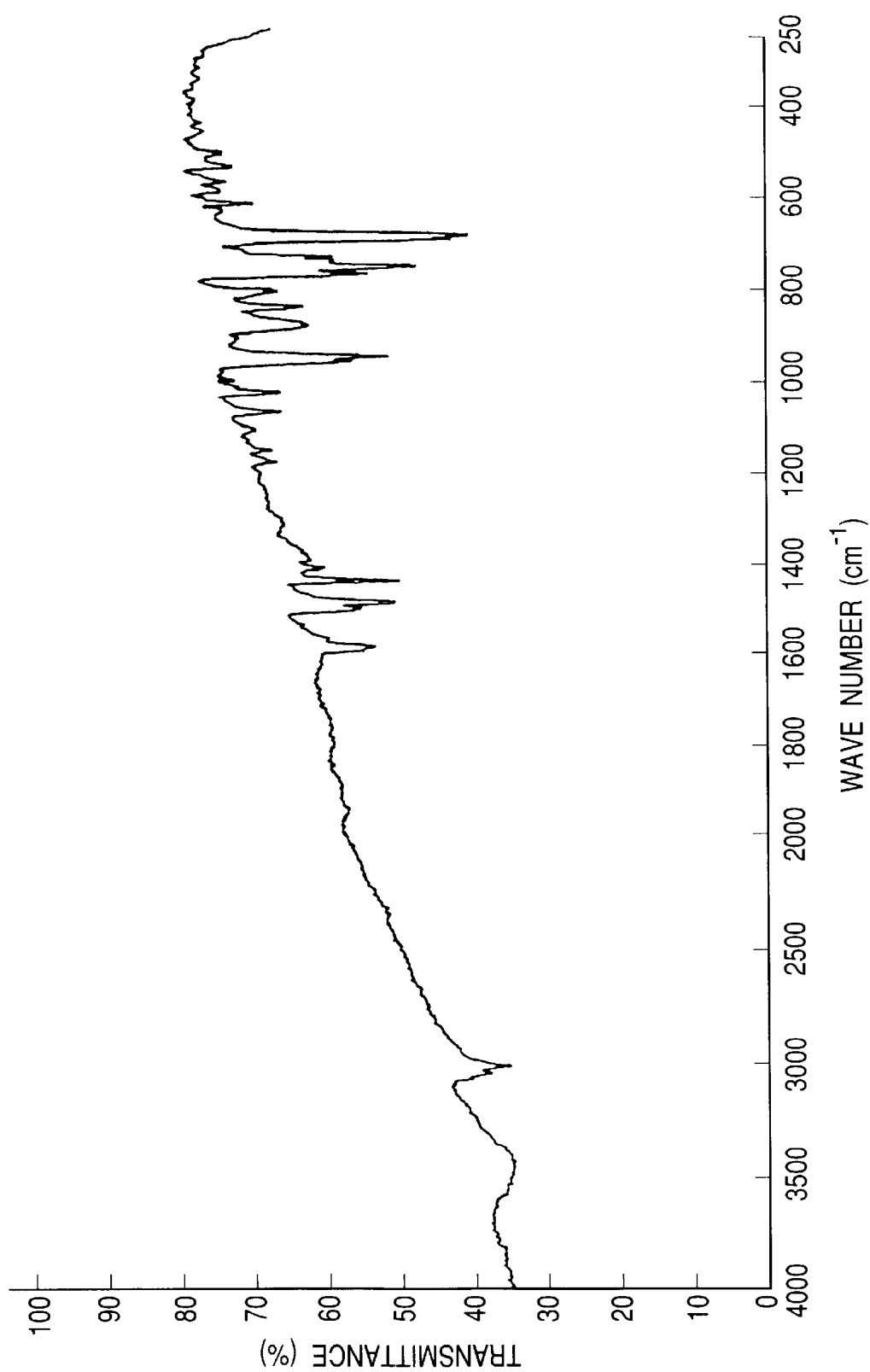
FIG. 4 is a spectrogram showing infrared absorption spectra of compound No. 1a-02 according to the invention.

The elemental analysis of the crystals revealed that carbon was found at 94.03% (94.15%, calculated for compound No. 1a-02) and hydrogen was found at 5.68% (5.85%, calculated for compound No. 1a-02). The infrared absorption spectral chart of the crystals (determined by a KBr tablet method) is shown in FIG. 4, from which the stretch vibrations ascribed to the aromatic rings are observed in the vicinity of 1590 cm$^{-1}$. The crystals were subjected to the analysis of proton nuclear magnetic resonance (using a solvent of CDCl$_3$ and an internal standard of TMS), revealing that the proton of the aromatic rings and the proton of the alkene were found at δ=6.9 to 8.2 ppm (40H).

With the mass spectra of the crystals, the molecular ion peak was observed at m/z=688. From the results of the above analyses, the crystals were identified as Compound No. 1a-02.

EXAMPLE 13

Preparation 2 of Compound No. 1a-02

3.04 g of diethyl diphenylmethylphosphate and 1.94 g of 1,3-bis((4-formylstyryl)naphthalene (compound No. 2a-01) were dissolved in 30 ml of N,N-dimethylformamide, to which 1.30 g of potassium tert-butoxide was added portion by portion over 10 minutes at 5 to 10° C. Thereafter, the resulting mixture was agitated at room temperature for 20 hours, to which 100 ml of ethanol was added. The resultant precipitate was removed by filtration, washed with water and dried to obtain 2.28 g of light yellow powder.

Next, the light yellow powder was subjected, in the same manner as in Example 12, to column chromatography using a stationary phase of silica gel and a mobile phase of a mixed solvent of toluene and hexane (at a ratio by volume of 1:1), thereby obtaining a light yellow, vitreous substance. Further, this light yellow vitreous substance was again subjected to column chromatograph using silica gel as a stationary phase and a mixed solvent of toluene and hexane (with a ratio by volume of 1:2) as a mobile phase, thereby obtaining 2.10 g of a yellow vitreous substance.

Subsequently, the substance was recrystallized from a mixed solvent of chloroform and ethanol and vacuum dried at 100° C. to obtain 1.88 g of yellow crystals having intense fluorescence at a yield of 55%. The crystals had a melting point of 180° C. The elemental analysis of the crystals revealed that carbon was found at 93.89% (94.15%, calculated for compound No. 1a-02) and hydrogen was found at 5.66% (5.85%, calculated for compound No. 1a-02).

The infrared absorption spectra, nuclear magnetic resonance spectra and mass spectra were, respectively, coincident with those of the compound obtained in Example 12, demonstrating that both compounds were identical to each other and were identified as compound No. 1a-02.

EXAMPLE 14

Preparation 3 of Compound No. 1a-02

0.921 g of 1,3-naphthalene dicarbaldehyde and 4.06 g of diethyl 4-(2,2'-diphenylvinyl)benzylphosphonate were dissolved in 30 ml of N,N-dimethylformamide, to which 1.30 g of potassium tert-butoxide was added portion by portion over 10 minutes at 5 to 10° C. Thereafter, the resulting mixture was agitated at room temperature for 20 hours, to which 80 ml of ethanol was added. The resultant precipitate was removed by filtration, washed with water and dried to obtain 2.23 g of light yellow powder.

Next, the light yellow powder was subjected, in the same manner as in Example 12, to column chromatography using a stationary phase of silica gel and a mobile phase of a mixed solvent of toluene and hexane (at a ratio by volume of 1:1), thereby obtaining a light yellow, vitreous substance. Further, this light yellow vitreous substance was again subjected to column chromatograph using silica gel as a stationary phase and a mixed solvent of toluene and hexane (with a ratio by volume of 1:2) as a mobile phase, thereby obtaining 1.83 g of a yellow vitreous substance.

Subsequently, the substance was recrystallized from a mixed solvent of chloroform and ethanol and vacuum dried at 100° C. to obtain 1.55 g of light yellow crystals having intense fluorescence at a yield of 45%. The crystals had a melting point of 180° C. The elemental analysis of the crystals revealed that carbon was found at 93.91% (94.15%, calculated for compound No. 1a-02) and hydrogen was found at 5.68% (5.85%, calculated for compound No. 1a-02).

The infrared absorption spectra, nuclear magnetic resonance spectra and mass spectra were, respectively, coincident with those of the compound obtained in Example 12, demonstrating that both compounds were identical to each other and were identified as compound No. 1a-02.

EXAMPLE 15

Preparation 4 of Compound No. 1a-02

1.82 g of benzophenone and 3.16 g of tetraethyl 1,3-bis (4-methylstyryl)naphthalene-$\alpha,\alpha'$-diyldiphosphonate were dissolved in 30 ml of N,N-dimethylformamide, to which 1.30 g of potassium tert-butoxide was added portion by portion over 10 minutes at 5 to 10° C. Thereafter, the resulting mixture was agitated at room temperature for 20 hours, to which 100 ml of water was added. The resultant precipitate was filtered out, washed with water and dried to obtain 1.90 g of light yellow powder.

Next, the light yellow powder was subjected, in the same manner as in Example 12, to column chromatography using a stationary phase of silica gel and a mobile phase of a mixed solvent of toluene and hexane (at a ratio by volume of 1:1), thereby obtaining a light yellow, vitreous substance. Further, this light yellow vitreous substance was again subjected to column chromatograph using silica gel as a stationary phase and a mixed solvent of toluene and hexane (with a ratio by volume of 1:2) as a mobile phase, thereby obtaining 1.42 g of a light yellow vitreous substance.

Subsequently, the substance was recrystallized from a mixed solvent of chloroform and ethanol and vacuum dried at 100° C. to obtain 1.28 g of yellow crystals having intense fluorescence at a yield of 37%. The crystals had a melting point of 180° C. The elemental analysis of the crystals revealed that carbon was found at 94.10% (94.15%, calculated for compound No. 1a-02) and hydrogen was found at 5.79% (5.85%, calculated for compound No. 1a-02). The infrared absorption spectra, nuclear magnetic resonance spectra and mass spectra were, respectively, coincident with those of the compound obtained in Example 12, demonstrating that both compounds were identical to each other and were identified as compound No. 1a-02.

EXAMPLE 16

Preparation 1 of Compound No. 2a-01

8.57 g of tetraethyl 1,3-dimethylnaphthalene-$\alpha,\alpha'$-diyldiphosphonate and 8.75 g of terephthalaldehyde monodiethylacetal were dissolved in 80 ml of N,N-dimethylformamide, to which 5.67 g of potassium tert-butoxide was added portion by portion over 10 minutes at 5 to 10° C. Thereafter, the resulting mixture was agitated at room temperature for 25 hours, to which 38.5 ml of 36% hydrochloric acid was added, followed by further agitation on a bath at a temperature of 80 to 85° C. for 30 minutes. After standing the reaction mixture to cool, about 150 ml of water was added thereto, and the resultant crystals were removed by filtration, washed with water and vacuum dried at 60° C. to obtain 7.30 g of light yellow crystals.

The thus obtained light yellow crystals were recrystallized from a mixed solvent of toluene and ethanol and vacuum dried at 80° C., thereby obtaining 6.13 g of light yellow crystals at a yield of 79%. The elemental analysis of the crystals revealed that carbon was found at 86.39% (86.57%, calculated for compound No. 2a-01) and hydrogen was found at 4.97% (5.19%, calculated for compound No. 2a-01).

The crystals were identified as compound No. 2a-01 through infrared absorption spectra, proton nuclear magnetic resonance spectra and mass spectra, like the foregoing examples.

EXAMPLE 17

Preparation 2 of Compound No. 2a-01

8.57 g of tetraethyl 1,3-dimethylnaphthalene-$\alpha,\alpha'$-diyldiphosphonate and 13.41 g of terephthalaldehyde were dissolved in 160 ml of N,N-dimethylformamide, to which 5.67 g of potassium tert-butoxide was added portion by portion over 10 minutes at 5 to 10° C. Thereafter, the resulting mixture was agitated at room temperature for 20 hours, to which about 300 ml of water was added. The resultant crystals were removed by filtration, washed with water, and further washed with 200 ml of hot ethanol to obtain 6.20 g of light yellow powder.

The thus obtained light yellow powder was repeatedly recrystallized from a mixed solvent of toluene and ethanol and vacuum dried at 80° C., thereby obtaining 1.40 g of light yellow crystals at a yield of 18%. The elemental analysis of the crystals revealed that carbon was found at 86.43% (86.57%, calculated for compound No. 2a-01) and hydrogen was found at 5.12% (5.19%, calculated for compound No. 2a-01).

The infrared absorption spectra, nuclear magnetic resonance spectra and mass spectra were, respectively, coincident with those of the compound obtained in Example 16, demonstrating that both compounds were identical to each other and were identified as compound No. 2a-01.

EXAMPLE 18

Preparation 1 of Compound No. 3a-01

4.28 g of tetraethyl 1,3-dimethylnaphthalene-$\alpha,\alpha'$-diyldiphosphonate and 2.64 g of 4-methylbenzaldehyde were dissolved in 60 ml of N,N-dimethylformamide, to which 2.60 g of potassium tert-butoxide was added portion by portion over 10 minutes at 5 to 10° C. Thereafter, the resulting mixture was agitated at room temperature for 20 hours, to which about 150 ml of water was added. The resulting crystals were removed by filtration, washed with water and vacuum dried to obtain 3.33 g of light brown powder.

The thus obtained powder was recrystallized from ethanol to obtain 2.12 g of light yellow crystals at a yield of 59%. The elemental analysis of the crystals revealed that carbon was found at 93.07% (93.29%, calculated for compound No. 3a-01) and hydrogen was found at 6.49% (6.71%, calculated for compound No. 3a-01).

The crystals were identified as compound No. 3a-01 through the analyses of the infrared absorption spectra, proton nuclear magnetic resonance spectra and mass spectra.

EXAMPLE 19

Preparation 2 of Compound 3a-01

1.84 g of 1,3-naphthalene dicarbaldehyde and 4.85 g of diethyl 4-methylbenzylphosphonate were dissolved in 60 ml of N,N-dimethylformamide, to which 2.60 g of potassium tert-butoxide was added portion by portion over 10 minutes at 5 to 10° C. Thereafter, the resulting mixture was agitated at room temperature for 20 hours, to which about 150 ml of water was added. The resulting crystals were removed by filtration, washed with water and vacuum dried to obtain 3.20 g of light brown powder.

The thus obtained powder was recrystallized from ethanol to obtain 2.11 g of light yellow needle crystals at a yield of 59%. The elemental analysis of the crystals revealed that carbon was found at 93.18% (93.29%, calculated for compound No. 3a-01) and hydrogen was found at 6.69% (6.71%, calculated for compound No. 3a-01).

The infrared absorption spectra, nuclear magnetic resonance spectra and mass spectra were, respectively, coincident with those of the compound obtained in Example 18, demonstrating that both compounds were identical to each other and were identified as compound No. 3a-01

EXAMPLE 20

An organic electroluminescent device was made in such a way that a hole transport layer, an emission layer, an electron transport layer and a cathode (aluminium/lithium (Al/Li)) were successively deposited by vacuum deposition on an electrode of a glass substrate wherein an indium tin oxide (ITO) thin film had been previously formed as a transparent electrode (i.e. an ITO glass substrate).

More particularly, the ITO glass substrate, N,N'-diphenyl-N,N'-bis(3-methylphenyl)benzidine (TPD) serving as a hole transport material, an aromatic methylidene compound corresponding to compound No. 1a-02 of the invention and serving as a light-emitting material, and tris(8-hydroxyquinolino)aluminium (Alq) serving as an electron transport material) were, respectively, set in a vacuum deposition device, followed by evacuation to $10^{-4}$ Pa.

Next, TPD used as a hole transport material was vacuum deposited on the electrode of the ITO glass substrate at a rate of 0.1 to 0.5 nm/second, thereby forming a 50 nm thick hole transport layer.

Thereafter, the compound No. 1a-02 used as an emission material was vacuum deposited at a deposition rate of 0.1 to 0.5 nm/second to form a 50 nm thick emission layer. Alq used as an electron transport material was vacuum deposited at a rate of 0.1 nm/second to form a 10 nm thick electron transport layer. Moreover, Li and Al were simultaneously subjected to vacuum deposition at rates of 0.01 to 0.02 nm/second and 1 to 2 nm/second, respectively, thereby forming an Al/Li electrode with a thickness of 150 nm.

These depositions were continuously performed without breakage of vacuum, and the respective thicknesses were controlled by monitoring with a crystal oscillator. Immediately after making of the device, lead wires were attached to the respective electrodes in dry nitrogen to complete an organic electroluminescent device. When a voltage was applied to the device, uniform blue emission was obtained. When a drive voltage and an emission luminance were measured by application of an electric current of 100 mA/cm$^2$, the drive voltage was found at 7.3V and the luminance was at 2200 cd/m$^2$.

EXAMPLE 21

Preparation 1 of Compound No. 1b-02

0.857 g of tetraethyl 1,4-dimethylnaphthalene-$\alpha,\alpha'$-diyldiphosphonate and 1.14 g of 4'-formyl-$\alpha$-phenylstilbene were dissolved in 12 ml of N,N-dimethylformamide, to which 0.520 g of potassium tert-butoxide was added portion by portion over 10 minutes at 5 to 10° C. Thereafter, the resulting mixture was agitated at room temperature for 20 hours, to which about 30 ml of ethanol was added. The resulting precipitate was removed by filtration, washed with water and dried to obtain 1.21 g of yellow powder.

Figure 5:
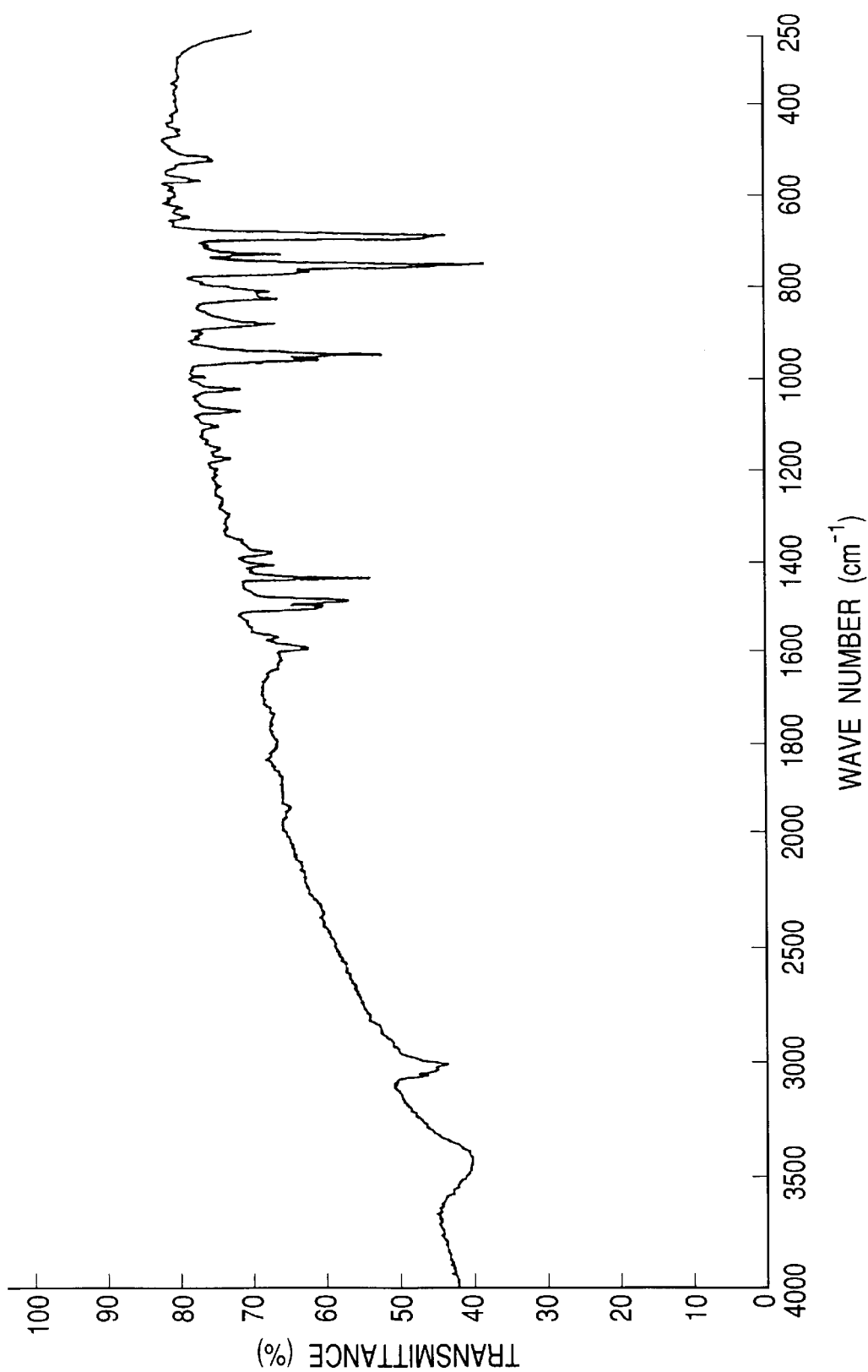
FIG. 5 is a spectrogram showing infrared absorption spectra of compound No. 1b-02 according to the invention.

Next, the yellow powder was subjected to column chromatography using a stationary phase of silica gel and a mobile phase made of toluene, thereby obtaining yellowish orange crystals. Further, the crystals were recrystallized from a mixed solvent of toluene and hexane and vacuum dried at 120° C. to obtain 1.15 g of orangish yellow crystals having intense fluorescence at a yield of 83%. The crystals had a melting point of 209.0 to 210.0° C. The elemental analysis of the crystals revealed that carbon was found at 94.09% (94.15%, calculated for compound No. 1b-02) and hydrogen was found at 5.66% (5.85%, calculated for compound No. 1b-02). The infrared absorption spectral chart of the crystals (determined by a KBr tablet method) is shown in FIG. 5, from which the stretch vibrations ascribed to the aromatic rings are observed in the vicinity of 1590 cm$^{-1}$. The crystals were subjected to the analysis of proton nuclear magnetic resonance (using a solvent of CDCl$_3$ and an internal standard of TMS), revealing that the proton of the aromatic rings and the proton of the alkene were found at δ=7.0 to 8.2 ppm (40H).

With the mass spectra of the crystals, the molecular ion peak was observed at m/z=688. From the results of the above analyses, the crystals were identified as Compound No. 1b-02.

EXAMPLE 22

Preparation 2 of Compound No. 1b-02

3.04 g of diethyl diphenylmethylphosphate and 1.94 g of 1,4-bis((4-formylstyryl)naphthalene (compound No. 2b-01) were dissolved in 30 ml of N,N-dimethylformamide, to which 1.30 g of potassium tert-butoxide was added portion by portion over 10 minutes at 5 to 10° C. Thereafter, the resulting mixture was agitated at room temperature for 20 hours, to which 100 ml of ethanol was added. The resultant precipitate was removed by filtration, washed with water and dried to obtain 2.55 g of orangish yellow powder.

Next, the orangish yellow powder was subjected, in the same manner as in Example 21, to column chromatography using a stationary phase of silica gel and a mobile phase of toluene, thereby obtaining orangish yellow crystals. Further, the crystals were recrystallized from a mixed solvent of toluene and hexane and vacuum dried at 120° C. to obtain 2.34 g of orangish yellow crystals having intense fluorescence at a yield of 68%. The crystals had a melting point of 209.0 to 210.0° C. The elemental analysis of the crystals revealed that carbon was found at 94.00% (94.15%, calculated for compound No. 1b-02) and hydrogen was found at 5.73% (5.85%, calculated for compound No. 1b-02).

The infrared absorption spectra, nuclear magnetic resonance spectra and mass spectra were, respectively, coincident with those of the compound obtained in Example 21, demonstrating that both compounds were identical to each other and were identified as compound No. 1b-02.

EXAMPLE 23

Preparation 3 of Compound No. 1b-02

0.921 g of 1,4-naphthalene dicarbaldehyde and 4.06 g of diethyl 4-(2,2'-diphenylvinyl)benzylphosphonate were dissolved in 30 ml of N,N-dimethylformamide, to which 1.30 g of potassium tert-butoxide was added portion by portion over 10 minutes at 5 to 10° C. Thereafter, the resulting mixture was agitated at room temperature for 20 hours, to which 80 ml of ethanol was added. The resultant precipitate was removed by filtration, washed with water and dried to obtain 2.08 g of orangish yellow powder.

Next, the orangish yellow powder was subjected, in the same manner as in Example 21, to column chromatography using a stationary phase of silica gel and a mobile phase of toluene, thereby obtaining an orangish yellow crystals. Further, the orangish yellow crystals were recrystallized from a mixed solvent of toluene and hexane and vacuum dried at 120° C. to obtain 1.92 g of orangish yellow crystals having intense fluorescence at a yield of 56%. The crystals had a melting point of 209.0 to 210.0° C. The elemental analysis of the crystals revealed that carbon was found at 94.12% (94.15%, calculated for compound No. 1b-02) and hydrogen was found at 5.77% (5.85%, calculated for compound No. 1b-02).

The infrared absorption spectra, nuclear magnetic resonance spectra and mass spectra were, respectively, coincident with those of the compound obtained in Example 21, demonstrating that both compounds were identical to each other and were identified as compound No. 1b-02.

EXAMPLE 25

Preparation 1 of Compound No. 2b-01

8.57 g of tetraethyl 1,4-dimethylnaphthalene-α,α'-diyldiphosphonate and 8.75 g of terephthalaldehyde monodiethylacetal were dissolved in 80 ml of N,N-dimethylformamide, to which 5.67 g of potassium tert-butoxide was added portion by portion over 10 minutes at 5 to 10° C. Thereafter, the resulting mixture was agitated at room temperature for 25 hours, to which 38.5 ml of 36% hydrochloric acid was added, followed by further agitation on a bath at a temperature of 80 to 85° C. for 30 minutes. After standing the reaction mixture to cool, about 150 ml of water was added thereto, and the resultant crystals were removed by filtration, washed with water and vacuum dried at 60° C. to obtain 7.01 g of yellow crystals.

The thus obtained yellow crystals were recrystallized from toluene and vacuum dried at 80° C., thereby obtaining 6.77 g of yellow crystals at a yield of 87%. The elemental analysis of the crystals revealed that carbon was found at 86.31% (86.57%, calculated for compound No. 2b-01) and hydrogen was found at 4.99% (5.19%, calculated for compound No. 2b-01). The crystals were identified as compound No. 2b-01 through infrared absorption spectra, proton nuclear magnetic resonance spectra and mass spectra, like the foregoing examples.

EXAMPLE 26

Preparation 2 of Compound No. 2b-01

8.57 g of tetraethyl 1,4-dimethylnaphthalene-α,α'-diyldiphosphonate and 13.41 g of terephthalaldehyde were dissolved in 160 ml of N,N-dimethylformamide, to which 5.67 g of potassium tert-butoxide was added portion by portion over 10 minutes at 5 to 10° C. Thereafter, the resulting mixture was agitated at room temperature for 20 hours, to which about 300 ml of water was added. The resultant crystals were removed by filtration, washed with water, and further washed with 200 ml of hot ethanol to obtain 7.04 g of yellow powder.

The thus obtained yellow powder was repeatedly recrystallized from toluene and vacuum dried at 80° C., thereby obtaining 1.55 g of yellow crystals at a yield of 20%. The elemental analysis of the crystals revealed that carbon was found at 86.48% (86.57%, calculated for compound No. 2b-01) and hydrogen was found at 5.11% (5.19%, calculated for compound No. 2b-01).

The infrared absorption spectra, nuclear magnetic resonance spectra and mass spectra were, respectively, coincident with those of the compound obtained in Example 25, demonstrating that both compounds were identical to each other and were identified as compound No. 2b-01.

EXAMPLE 27

Preparation 1 of Compound No. 3b-01

4.28 g of tetraethyl 1,4-dimethylnaphthalene-α,α'-diyldiphosphonate and 2.64 g of 4-methylbenzaldehyde were dissolved in 60 ml of N,N-dimethylformamide, to which 2.60 g of potassium tert-butoxide was added portion by portion over 10 minutes at 5 to 10° C. Thereafter, the resulting mixture was agitated at room temperature for 20 hours, to which about 150 ml of water was added. The resulting crystals were removed by filtration, washed with water and vacuum dried to obtain 3.26 g of yellowish brown powder.

The thus obtained powder was recrystallized from N,N-dimethylformamide to obtain 3.03 g of yellow crystals at a yield of 84%. The elemental analysis of the crystals revealed that carbon was found at 93.14% (93.29%, calculated for compound No. 3b-01) and hydrogen was found at 6.52% (6.71%, calculated for compound No. 3b-01). The crystals were identified as compound No. 3b-01 through the analyses of the infrared absorption spectra, proton nuclear magnetic resonance spectra and mass spectra, like the above example.

EXAMPLE 28

Preparation 2 of compound 3b-01

1.84 g of 1,4-naphthalene dicarbaldehyde and 4.85 g of diethyl 4-methylbenzylphosphonate were dissolved in 60 ml of N,N-dimethylformamide, to which 2.60 g of potassium tert-butoxide was added portion by portion over 10 minutes at 5 to 10° C. Thereafter, the resulting mixture was agitated at room temperature for 20 hours, to which about 150 ml of water was added. The resulting crystals were removed by filtration, washed with water and vacuum dried to obtain 3.12 g of yellowish brown powder.

The thus obtained powder was recrystallized from N,N-dimethylformamide to obtain 2.97 g of yellow crystals at a yield of 83%. The elemental analysis of the crystals revealed that carbon was found at 93.14% (93.29%, calculated for compound No. 3b-01) and hydrogen was found at 6.64% (6.71%, calculated for compound No. 3b-01).

The infrared absorption spectra, nuclear magnetic resonance spectra and mass spectra were, respectively, coincident with those of the compound obtained in Example 27, demonstrating that both compounds were identical to each other and were identified as compound No. 3b-01

EXAMPLE 29

An organic electroluminescent device was made in such a way that a hole transport layer, an emission layer, an electron transport layer and a cathode (aluminium/lithium (Al/Li)) were successively deposited by vacuum deposition on an electrode of a glass substrate wherein an indium tin oxide (ITO) thin film had been previously formed as a transparent electrode (i.e. an ITO glass substrate).

More particularly, the ITO glass substrate, N,N'-diphenyl-N,N'-bis(3-methylphenyl)benzidine (TPD) serving as a hole transport material, an aromatic methylidene compound corresponding to compound No. 1b-02 of the invention and serving as a light-emitting material, and tris(8-hydroxyquinolino)aluminium (Alq) serving as an electron transport material) were, respectively, set in a vacuum deposition device, followed by evacuation to $10^{-4}$ Pa.

Next, TPD used as a hole transport material was vacuum deposited on the electrode of the ITO glass substrate at a rate of 0.1 to 0.5 nm/second, thereby forming a 50 nm thick hole transport layer.

Thereafter, the compound No. 1b-02 used as an emission material was vacuum deposited at a deposition rate of 0.1 to 0.5 nm/second to form a 50 nm thick emission layer. Alq used as an electron transport material was vacuum deposited at a rate of 0.1 nm/second to form a 10 nm thick electron transport layer. Moreover, Li and Al were simultaneously subjected to vacuum deposition at rates of 0.01 to 0.02 nm/second and 1 to 2 nm/second, respectively, thereby forming an Al/Li electrode with a thickness of 150 nm.

These depositions were continuously performed without breakage of vacuum, and the respective thicknesses were controlled by monitoring with a crystal oscillator. Immediately after making of the device, lead wires were attached to the respective electrodes in dry nitrogen to complete an organic electroluminescent device. When a voltage was applied to the device, uniform green emission was obtained. When a drive voltage and an emission luminance were measured by application of an electric current of 100 mA/cm$^2$, the drive voltage was found at 7.0V and the luminance was at 2200 cd/m$^2$.

EXAMPLE 30

Preparation 1 of Compound No. 1c-02

0.857 g of tetraethyl 1,8-dimethylnaphthalene-α,α'-diyldiphosphonate and 1.14 g of 4'-formyl-α-phenylstilbene were dissolved in 17 ml of N,N-dimethylformamide, to which 0.520 g of potassium tert-butoxide was added portion by portion over 10 minutes at 5 to 10° C. Thereafter, the resulting mixture was agitated at room temperature for 20 hours, to which about 50 ml of ethanol was added. The resulting precipitate was removed by filtration, washed with water and dried to obtain 1.10 g of light yellow powder.

Next, the light yellow powder was subjected to column chromatography using a stationary phase of silica gel and a mobile phase made of toluene, thereby obtaining light yellow crystals. Further, the crystals were recrystallized from a mixed solvent of toluene and hexane and vacuum dried at 120° C. to obtain 1.06 g of light yellow needle crystals having intense fluorescence at a yield of 77%. The crystals had a melting point of 212.0 to 213.0° C. The elemental analysis of the crystals revealed that carbon was found at 94.06% (94.15%, calculated for compound No. 1c-02) and hydrogen was found at 5.71% (5.85%, calculated for compound No. 1c-02).

Figure 6:
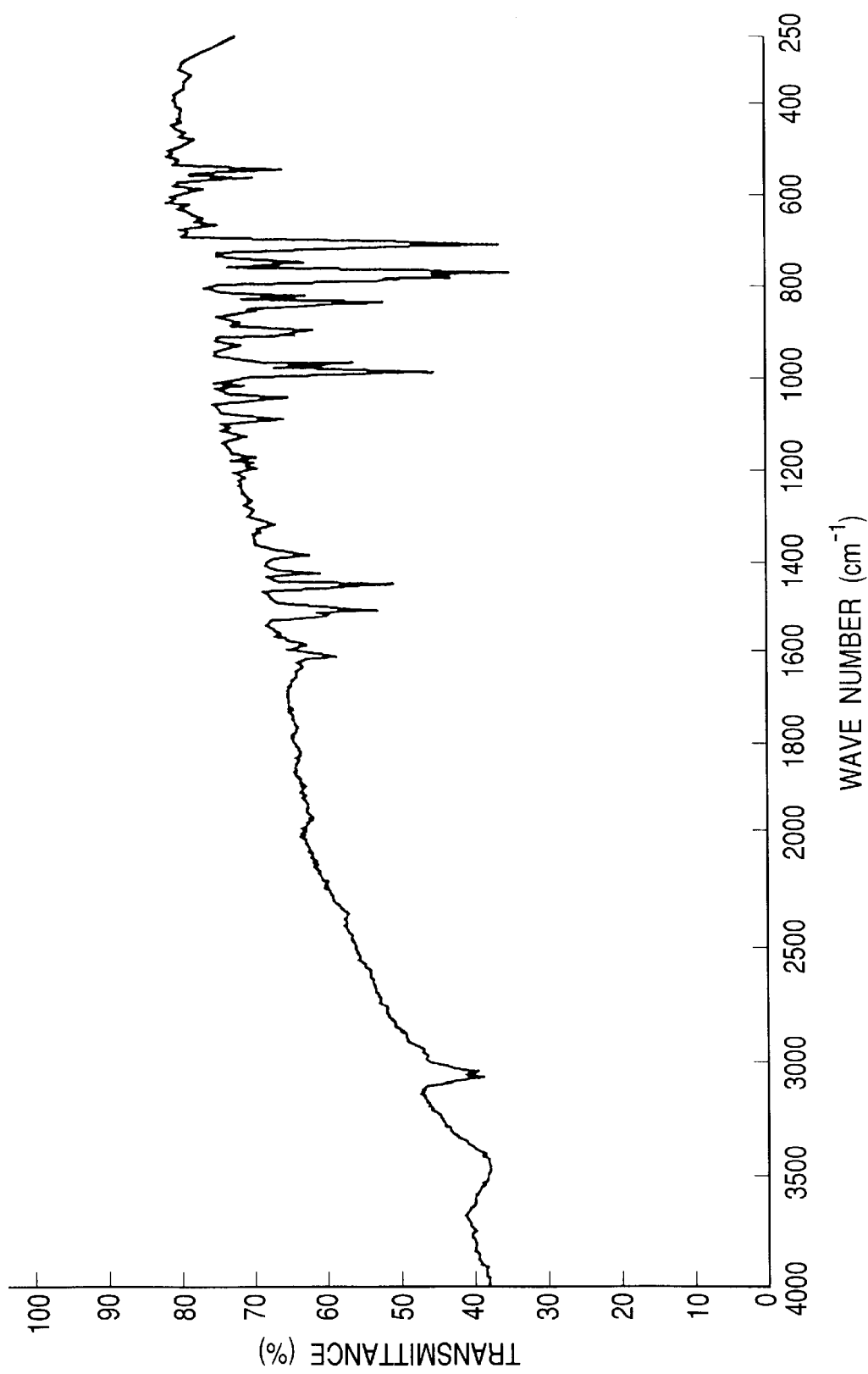
FIG. 6 is a spectrogram showing infrared absorption spectra of compound No. 1c-02 according to the invention.

The infrared absorption spectral chart of the crystals (determined by a KBr tablet method) is shown in FIG. 6, from which the stretch vibrations ascribed to the aromatic rings are observed in the vicinity of 1590 cm$^{-1}$. The crystals were subjected to the analysis of proton nuclear magnetic resonance (using a solvent of CDCl$_3$ and an internal standard of TMS), revealing that the proton of the aromatic rings and the proton of the alkene were found at δ=6.8 to 7.9 ppm (40H). With the mass spectra of the crystals, the molecular ion peak was observed at m/z=688. From the results of the above analyses, the crystals were identified as Compound No. 1c-02.

EXAMPLE 31

Preparation 2 of Compound No. 1c-02

3.04 g of diethyl diphenylmethylphosphate and 1.94 g of 1,8-bis((4-formylstyryl)naphthalene (compound No. 2c-01) were dissolved in 30 ml of N,N-dimethylformamide, to which 1.30 g of potassium tert-butoxide was added portion by portion over 10 minutes at 5 to 10° C. Thereafter, the resulting mixture was agitated at room temperature for 20 hours, to which 100 ml of ethanol was added. The resultant precipitate was removed by filtration, washed with water and dried to obtain 2.80 g of light yellow powder.

Next, the light yellow powder was subjected, in the same manner as in Example 30, to column chromatography using a stationary phase of silica gel and a mobile phase of toluene, thereby obtaining light yellow crystals. Further, the crystals were recrystallized from a mixed solvent of toluene and hexane and vacuum dried at 120° C. to obtain 2.35 g of light yellow crystals having intense fluorescence at a yield of 68%. The crystals had a melting point of 212.0 to 213.0° C. The elemental analysis of the crystals revealed that carbon was found at 94.02% (94.15%, calculated for compound No. 1c-02) and hydrogen was found at 5.71% (5.85%, calculated for compound No. 1c-02).

The infrared absorption spectra, nuclear magnetic resonance spectra and mass spectra were, respectively, coincident with those of the compound obtained in Example 30, demonstrating that both compounds were identical to each other and were identified as compound No. 1c-02.

EXAMPLE 32

Preparation 3 of Compound No. 1c-02

0.921 g of 1,8-naphthalene dicarbaldehyde and 4.06 g of diethyl 4-(2,2'-diphenylvinyl)benzylphosphonate were dissolved in 30 ml of N,N-dimethylformamide, to which 1.30 g of potassium tert-butoxide was added portion by portion over 10 minutes at 5 to 10° C. Thereafter, the resulting mixture was agitated at room temperature for 20 hours, to which 80 ml of ethanol was added. The resultant precipitate was removed by filtration, washed with water and dried to obtain 2.23 g of light yellow powder.

Next, the light yellow powder was subjected, in the same manner as in Example 30, to column chromatography using a stationary phase of silica gel and a mobile phase of toluene, thereby obtaining a light yellow crystals. Further, the light yellow crystals were recrystallized from a mixed solvent of toluene and hexane and vacuum dried at 120° C. to obtain 2.13 g of light yellow crystals having intense fluorescence at a yield of 62%. The crystals had a melting point of 212.0 to 213.0° C. The elemental analysis of the crystals revealed that carbon was found at 94.00% (94.15%, calculated for compound No. 1c-02) and hydrogen was found at 5.63% (5.85%, calculated for compound No. 1c-02).

The infrared absorption spectra, nuclear magnetic resonance spectra and mass spectra were, respectively, coincident with those of the compound obtained in Example 30, demonstrating that both compounds were identical to each other and were identified as compound No. 1c-02.

EXAMPLE 33

Preparation 4 of Compound No. 1c-02

1.82 g of benzophenone and 3.16 g of tetraethyl 1,8-bis(4-methylstyryl)naphthalene-α,α'-diyldiphosphonate were dissolved in 30 ml of N,N-dimethylformamide, to which 1.30 g of potassium tert-butoxide was added portion by portion over 10 minutes at 5 to 10° C. Thereafter, the resulting mixture was agitated at room temperature for 20 hours, to which 100 ml of ethanol was added. The resultant precipitate was filtered out, washed with water and dried to obtain 1.99 g of light yellow powder.

Next, the light yellow powder was subjected, in the same manner as in Example 30, to column chromatography using a stationary phase of silica gel and a mobile phase of toluene, thereby obtaining light yellow crystals. Further, the light yellow crystals were recrystallized from a mixed solvent of chloroform and hexane and vacuum dried at 120° C. to obtain 1.64 g of light yellow crystals having intense fluorescence at a yield of 48%. The crystals had a melting point of 212.0 to 213.0° C. The elemental analysis of the crystals revealed that carbon was found at 93.95% (94.15%, calculated for compound No. 1c-02) and hydrogen was found at 5.56% (5.85%, calculated for compound No. 1c-02).

The infrared absorption spectra, nuclear magnetic resonance spectra and mass spectra were, respectively, coincident with those of the compound obtained in Example 30, demonstrating that both compounds were identical to each other and were identified as compound No. 1c-02.

EXAMPLE 34

Preparation 1 of Compound No. 2c-01

8.57 g of tetraethyl 1,8-dimethylnaphthalene-α,α'-diyldiphosphonate and 8.75 g of terephthalaldehyde monodiethylacetal were dissolved in 80 ml of N,N-dimethylformamide, to which 5.67 g of potassium tert-butoxide was added portion by portion over 10 minutes at 5 to 10° C.

Thereafter, the resulting mixture was agitated at room temperature for 25 hours, to which 38.5 ml of 36% hydrochloric acid was added, followed by further agitation on a bath at a temperature of 80 to 85° C. for 30 minutes. After standing the reaction mixture to cool, about 150 ml of water was added thereto, and the resultant crystals were removed by filtration, washed with water and vacuum dried at 60° C. to obtain 7.51 g of light yellow crystals. The thus obtained light yellow crystals were recrystallized from a mixed solvent of toluene and ethanol and vacuum dried at 80° C., thereby obtaining 6.55 g of light yellow crystals at a yield of 84%. The elemental analysis of the crystals revealed that carbon was found at 86.29% (86.57%, calculated for compound No. 2c-01) and hydrogen was found at 4.98% (5.19%, calculated for compound No. 2c-01).

Like the above examples, the crystals were identified as compound No. 2c-01 through infrared absorption spectra, proton nuclear magnetic resonance spectra and mass spectra.

EXAMPLE 35

Preparation 2 of Compound No. 2c-01

8.57 g of tetraethyl 1,8-dimethylnaphthalene-α,α'-diyldiphosphonate and 13.41 g of terephthalaldehyde were dissolved in 160 ml of N,N-dimethylformamide, to which 5.67 g of potassium tert-butoxide was added portion by portion over 10 minutes at 5 to 10° C. Thereafter, the resulting mixture was agitated at room temperature for 20 hours, to which about 300 ml of water was added. The resultant crystals were removed by filtration, washed with water, and further washed with 200 ml of hot ethanol to obtain 5.90 g of light yellow powder.

The thus obtained light yellow powder was repeatedly recrystallized from a mixed solvent of toluene and ethanol and vacuum dried at 80° C., thereby obtaining 1.27 g of yellow crystals at a yield of 16%. The elemental analysis of the crystals revealed that carbon was found at 86.33% (86.57%, calculated for compound No. 2c-01) and hydrogen was found at 5.02% (5.19%, calculated for compound No. 2c-01).

The infrared absorption spectra, nuclear magnetic resonance spectra and mass spectra were, respectively, coincident with those of the compound obtained in Example 34, demonstrating that both compounds were identical to each other and were identified as compound No. 2c-01.

EXAMPLE 36

Preparation 1 of Compound No. 3c-01

4.28 g of tetraethyl 1,8-dimethylnaphthalene-$\alpha,\alpha'$-diyldiphosphonate and 2.64 g of 4-methylbenzaldehyde were dissolved in 60 ml of N,N-dimethylformamide, to which 2.60 g of potassium tert-butoxide was added portion by portion over 10 minutes at 5 to 10° C. Thereafter, the resulting mixture was agitated at room temperature for 20 hours, to which about 150 ml of water was added. The resulting crystals were removed by filtration, washed with water and vacuum dried to obtain 3.05 g of light yellow powder.

The thus obtained powder was recrystallized from a mixed solvent of toluene and ethanol to obtain 2.44 g of light yellow crystals at a yield of 68%. The elemental analysis of the crystals revealed that carbon was found at 93.17% (93.29%, calculated for compound No. 3c-01) and hydrogen was found at 6.56% (6.71%, calculated for compound No. 3c-01).

The crystals were identified as compound No. 3c-01 through the analyses of the infrared absorption spectra, proton nuclear magnetic resonance spectra and mass spectra, like the foregoing examples.

EXAMPLE 37

Preparation 2 of Compound 3c-01

1.84 g of 1,8-naphthalene dicarbaldehyde and 4.85 g of diethyl 4-methylbenzylphosphonate were dissolved in 60 ml of N,N-dimethylformamide, to which 2.60 g of potassium tert-butoxide was added portion by portion over 10 minutes at 5 to 10° C. Thereafter, the resulting mixture was agitated at room temperature for 20 hours, to which about 150 ml of water was added. The resulting crystals were removed by filtration, washed with water and vacuum dried to obtain 3.14 g of light brown powder.

The thus obtained powder was recrystallized from a mixed solvent of toluene and ethanol to obtain 2.84 g of light yellow crystals at a yield of 79%. The elemental analysis of the crystals revealed that carbon was found at 93.15% (93.29%, calculated for compound No. 3c-01) and hydrogen was found at 6.57% (6.71%, calculated for compound No. 3c-01).

The infrared absorption spectra, nuclear magnetic resonance spectra and mass spectra were, respectively, coincident with those of the compound obtained in Example 36, demonstrating that both compounds were identical to each other and were identified as compound No. 3c-01

EXAMPLE 38

An organic electroluminescent device was made in such a way that a hole transport layer, an emission layer, an electron transport layer and a cathode (aluminium/lithium (Al/Li)) were successively deposited by vacuum deposition on an electrode of a glass substrate wherein an indium tin oxide (ITO) thin film had been previously formed as a transparent electrode (i.e. an ITO glass substrate).

More particularly, the ITO glass substrate, N,N'-diphenyl-N,N'-bis(3-methylphenyl)benzidine (TPD) serving as a hole transport material, an aromatic methylidene compound corresponding to compound No. 1c-02 of the invention and serving as a light-emitting material, and tris(8-hydroxyquinolino)aluminium (Alq) serving as an electron transport material) were, respectively, set in a vacuum deposition device, followed by evacuation to $10^{-4}$ Pa.

Next, TPD used as a hole transport material was vacuum deposited on the electrode of the ITO glass substrate at a rate of 0.1 to 0.5 nm/second, thereby forming a 50 nm thick hole transport layer.

Thereafter, the compound No. 1b-02 used as an emission material was vacuum deposited at a deposition rate of 0.1 to 0.5 nm/second to form a 50 nm thick emission layer. Alq used as an electron transport material was vacuum deposited at a rate of 0.1 nm/second to form a 10 nm thick electron transport layer. Moreover, Li and Al were simultaneously subjected to vacuum deposition at rates of 0.01 to 0.02 nm/second and 1 to 2 nm/second, respectively, thereby forming an Al/Li electrode with a thickness of 150 nm.

These depositions were continuously performed without breakage of vacuum, and the respective thicknesses were controlled by monitoring with a crystal oscillator. Immediately after making of the device, lead wires were attached to the respective electrodes in dry nitrogen to complete an organic electroluminescent device. When a voltage was applied to the device, uniform blue emission was obtained. When a drive voltage and an emission luminance were measured by application of an electric current of 100 mA/cm$^2$, the drive voltage was found at 6.9V and the luminance was at 2100 cd/m$^2$.

EXAMPLE 39

Preparation 1 of Compound No. 1d-02

2.14 g of tetraethyl 2,3-dimethylnaphthalene-$\alpha,\alpha'$-diyldiphosphonate and 2.84 g of 4'-formyl-$\alpha$-phenylstilbene were dissolved in 30 ml of N,N-dimethylformamide, to which 1.30 g of potassium tert-butoxide was added portion by portion over 10 minutes at 5 to 10° C. Thereafter, the resulting mixture was agitated at room temperature for 20 hours, to which about 70 ml of ethanol was added. The resulting precipitate was removed by filtration, washed with water and dried to obtain 3.22 g of yellow crystals.

Next, the yellow crystals were recrystallized from toluene and vacuum dried at 100° C. to obtain 2.49 g of light yellow crystals having intense fluorescence at a yield of 72%. The crystals had a melting point of 232.0 to 234.0° C. The elemental analysis of the crystals revealed that carbon was found at 94.04% (94.15%, calculated for compound No. 1d-02) and hydrogen was found at 5.77% (5.85%, calculated for compound No. 1c-02).

Figure 7:
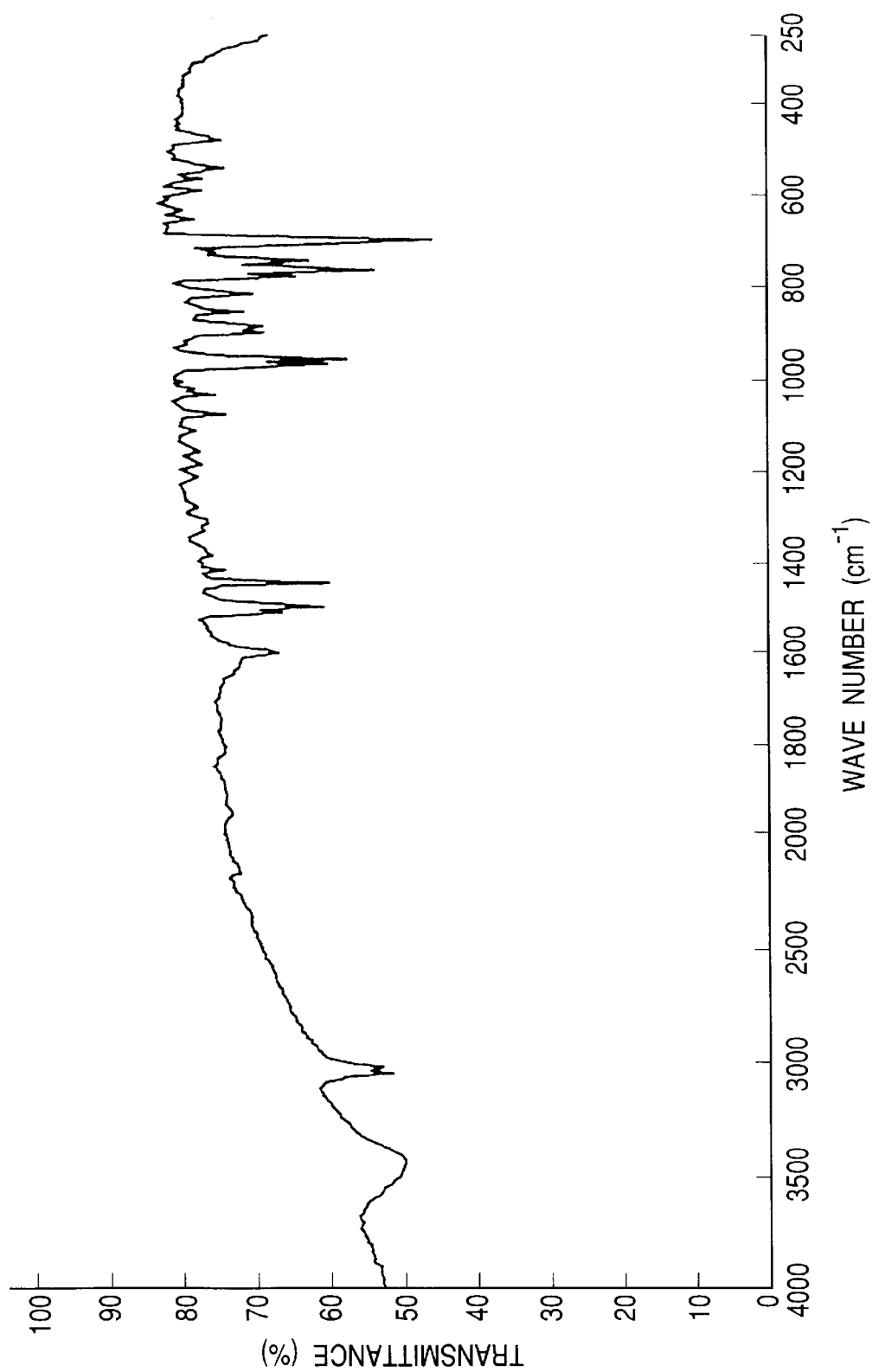
FIG. 7 is a spectrogram showing infrared absorption spectra of compound No. 1d-02 according to the invention.

The infrared absorption spectral chart of the crystals (determined by a KBr tablet method) is shown in FIG. 7, from which the stretch vibrations ascribed to the aromatic rings are observed in the vicinity of 1590 cm$^{-1}$. The crystals were subjected to the analysis of proton nuclear magnetic resonance (using a solvent of CDCl$_3$ and an internal standard of TMS), revealing that the proton of the aromatic rings and the proton of the alkene were found at $\delta$=6.9 to 8.0 ppm (40H). With the mass spectra of the crystals, the molecular ion peak was observed at m/z=688. From the results of the above analyses, the crystals were identified as Compound No. 1d-02.

EXAMPLE 40

Preparation 2 of Compound No. 1d-02

3.04 g of diethyl diphenylmethylphosphate and 1.94 g of 2,3-bis((4-formylstyryl)naphthalene (compound No. 2d-01) were dissolved in 30 ml of N,N-dimethylformamide, to which 1.30 g of potassium tert-butoxide was added portion by portion over 10 minutes at 5 to 10° C. Thereafter, the resulting mixture was agitated at room temperature for 20 hours, to which about 70 ml of ethanol was added. The resultant precipitate was removed by filtration, washed with water and dried to obtain yellow crystals.

Next, the yellow crystals were recrystallized from toluene and vacuum dried at 120° C. to obtain 2.35 g of light yellow crystals having intense fluorescence at a yield of 54%. The crystals had a melting point of 232.5 to 234.0° C. The elemental analysis of the crystals revealed that carbon was found at 93.92% (94.15%, calculated for compound No. 1d-02) and hydrogen was found at 5.58% (5.85%, calculated for compound No. 1d-02).

The infrared absorption spectra, nuclear magnetic resonance spectra and mass spectra were, respectively, coincident with those of the compound obtained in Example 39, demonstrating that both compounds were identical to each other and were identified as compound No. 1d-02.

EXAMPLE 41

Preparation 3 of Compound No. 1d-02

0.921 g of 2,3-naphthalene dicarbaldehyde and 4.06 g of diethyl 4-(2,2'-diphenylvinyl)benzylphosphonate were dissolved in 30 ml of N,N-dimethylformamide, to which 1.30 g of potassium tert-butoxide was added portion by portion over 10 minutes at 5 to 10° C. Thereafter, the resulting mixture was agitated at room temperature for 20 hours, to which about 70 ml of ethanol was added. The resultant precipitate was removed by filtration, washed with water and dried to obtain yellow powder.

Next, the yellow crystals were recrystallized from toluene and vacuum dried at 100° C. to obtain 1.61 g of light yellow crystals having intense fluorescence at a yield of 47%. The crystals had a melting point of 232.5 to 234.0° C. The elemental analysis of the crystals revealed that carbon was found at 93.96% (94.15%, calculated for compound No. 1d-02) and hydrogen was found at 5.63% (5.85%, calculated for compound No. 1d-02).

The infrared absorption spectra, nuclear magnetic resonance spectra and mass spectra were, respectively, coincident with those of the compound obtained in Example 39, demonstrating that both compounds were identical to each other and were identified as compound No. 1d-02.

EXAMPLE 42

Preparation 4 of Compound No. 1d-02

1.82 g of benzophenone and 3.16 g of tetraethyl 2,3-bis (4-methylstyryl)naphthalene-$\alpha,\alpha'$-diyldiphosphonate were dissolved in 30 ml of N,N-dimethylformamide, to which 1.30 g of potassium tert-butoxide was added portion by portion over 10 minutes at 5 to 10° C. Thereafter, the resulting mixture was agitated at room temperature for 20 hours, to which about 70 ml of ethanol was added. The resultant precipitate was filtered out, washed with water and dried to obtain yellow powder.

Next, the yellow crystals were recrystallized from toluene and vacuum dried at 100° C. to obtain 1.42 g of light yellow crystals having intense fluorescence at a yield of 41%. The crystals had a melting point of 232.5 to 234.0° C. The elemental analysis of the crystals revealed that carbon was found at 94.03% (94.15%, calculated for compound No. 1d-02) and hydrogen was found at 5.66% (5.85%, calculated for compound No. 1d-02).

The infrared absorption spectra, nuclear magnetic resonance spectra and mass spectra were, respectively, coincident with those of the compound obtained in Example 39, demonstrating that both compounds were identical to each other and were identified as compound No. 1d-02.

EXAMPLE 43

Preparation 1 of Compound No. 2d-01

8.57 g of tetraethyl 2,3-dimethylnaphthalene-$\alpha,\alpha'$-diyldiphosphonate and 8.75 g of terephthalaldehyde monodiethylacetal were dissolved in 80 ml of N,N-dimethylformamide, to which 5.67 g of potassium tert-butoxide was added portion by portion over 10 minutes at 5 to 10° C. Thereafter, the resulting mixture was agitated at room temperature for 25 hours, to which 38.5 ml of 36% hydrochloric acid was added, followed by further agitation on a bath at a temperature of 80 to 85° C. for 30 minutes.

After standing the reaction mixture to cool, about 150 ml of water was added thereto, and the resultant crystals were removed by filtration, washed with water and vacuum dried at 60° C. to obtain 7.41 g of yellow crystals. The thus obtained yellow crystals were recrystallized from a mixed solvent of toluene and ethanol and vacuum dried at 80° C, thereby obtaining 5.94 g of yellow crystals at a yield of 76%. The elemental analysis of the crystals revealed that carbon was found at 86.40% (86.57%, calculated for compound No. 2d-01) and hydrogen was found at 4.94% (5.19%, calculated for compound No. 2d-01).

Like the above examples, the crystals were identified as compound No. 2d-01 through infrared absorption spectra, proton nuclear magnetic resonance spectra and mass spectra.

EXAMPLE 44

Preparation 2 of Compound No. 2d-01

8.57 g of tetraethyl 2,3-dimethylnaphthalene-$\alpha,\alpha'$-diyldiphosphonate and 13.41 g of terephthalaldehyde were dissolved in 160 ml of N,N-dimethylformamide, to which 5.67 g of potassium tert-butoxide was added portion by portion over 10 minutes at 5 to 10° C. Thereafter, the resulting mixture was agitated at room temperature for 20 hours, to which about 300 ml of water was added. The resultant crystals were removed by filtration, washed with water, and further washed with 200 ml of hot ethanol to obtain 6.20 g of light yellow powder.

The thus obtained light yellow powder was repeatedly recrystallized from a mixed solvent of toluene and ethanol and vacuum dried at 80° C., thereby obtaining 1.22 g of yellow crystals at a yield of 16%. The elemental analysis of the crystals revealed that carbon was found at 86.43% (86.57%, calculated for compound No. 2d-01) and hydrogen was found at 5.10% (5.19%, calculated for compound No. 2d-01).

The infrared absorption spectra, nuclear magnetic resonance spectra and mass spectra were, respectively, coincident with those of the compound obtained in Example 43, demonstrating that both compounds were identical to each other and were identified as compound No. 2d-01.

EXAMPLE 45

Preparation 1 of Compound No. 3d-01

4.28 g of tetraethyl 2,3-dimethylnaphthalene-$\alpha,\alpha'$-diyldiphosphonate and 2.64 g of 4-methylbenzaldehyde were dissolved in 60 ml of N,N-dimethylformamide, to which 2.60 g of potassium tert-butoxide was added portion by portion over 10 minutes at 5 to 10° C. Thereafter, the resulting mixture was agitated at room temperature for 20 hours, to which about 150 ml of water was added. The resulting crystals were removed by filtration, washed with water and vacuum dried to obtain 3.23 g of light brown powder.

The thus obtained powder was recrystallized from a mixed solvent of toluene and ethanol to obtain 2.33 g of light yellow crystals at a yield of 65%. The elemental analysis of the crystals revealed that carbon was found at 93.11% (93.29%, calculated for compound No. 3d-01) and hydrogen was found at 6.56% (6.71%, calculated for compound No. 3d-01).

The crystals were identified as compound No. 3d-01 through the analyses of the infrared absorption spectra, proton nuclear magnetic resonance spectra and mass spectra, like the foregoing examples.

EXAMPLE 46

Preparation 2 of Compound 3d-01

1.84 g of 2,3-naphthalene dicarbaldehyde and 4.85 g of diethyl 4-methylbenzylphosphonate were dissolved in 60 ml of N,N-dimethylformamide, to which 2.60 g of potassium tert-butoxide was added portion by portion over 10 minutes at 5 to 10° C. Thereafter, the resulting mixture was agitated at room temperature for 20 hours, to which about 150 ml of water was added. The resulting crystals were removed by filtration, washed with water and vacuum dried to obtain 3.20 g of light brown powder.

The thus obtained powder was recrystallized from a mixed solvent of toluene and ethanol to obtain 2.45 g of light yellow crystals at a yield of 68%. The elemental analysis of the crystals revealed that carbon was found at 93.09% (93.29%, calculated for compound No. 3d-01) and hydrogen was found at 6.49% (6.71%, calculated for compound No. 3d-01).

The infrared absorption spectra, nuclear magnetic resonance spectra and mass spectra were, respectively, coincident with those of the compound obtained in Example 45, demonstrating that both compounds were identical to each other and were identified as compound No. 3d-01

EXAMPLE 47

An organic electroluminescent device was made in such a way that a hole transport layer, an emission layer, an electron transport layer and a cathode (aluminium/lithium (Al/Li)) were successively deposited by vacuum deposition on an electrode of a glass substrate wherein an indium tin oxide (ITO) thin film had been previously formed as a transparent electrode (i.e. an ITO glass substrate).

More particularly, the ITO glass substrate, N,N'-diphenyl-N,N'-bis(3-methylphenyl)benzidine (TPD) serving as a hole transport material, an aromatic methylidene compound corresponding to compound No. 1d-02 of the invention and serving as a light-emitting material, and tris(8-hydroxyquinolino)aluminium (Alq) serving as an electron transport material) were, respectively, set in a vacuum deposition device, followed by evacuation to $10^{-4}$ Pa.

Next, TPD used as a hole transport material was vacuum deposited on the electrode of the ITO glass substrate at a rate of 0.1 to 0.5 nm/second, thereby forming a 50 nm thick hole transport layer.

Thereafter, the compound No. 1b-02 used as an emission material was vacuum deposited at a deposition rate of 0.1 to 0.5 nm/second to form a 50 nm thick emission layer. Alq used as an electron transport material was vacuum deposited at a rate of 0.1 nm/second to form a 10 nm thick electron transport layer. Moreover, Li and Al were simultaneously subjected to vacuum deposition at rates of 0.01 to 0.02 nm/second and 1 to 2 nm/second, respectively, thereby forming an Al/Li electrode with a thickness of 150 nm.

These depositions were continuously performed without breakage of vacuum, and the respective thicknesses were controlled by monitoring with a crystal oscillator. Immediately after making of the device, lead wires were attached to the respective electrodes in dry nitrogen to complete an organic electroluminescent device. When a voltage was applied to the device, uniform sky blue emission was obtained. When a drive voltage and an emission luminance were measured by application of an electric current of 100 mA/cm², the drive voltage was found at 6.6V and the luminance was at 2000 cd/m².

As will be seen from the foregoing, when the aromatic methylidene compounds of the invention are used as an emission layer of an organic electroluminescent device, good emission characteristics are ensured and the device has good stability with a prolonged life. Thus, the compounds and their preparation are very important from an industrial viewpoint along with intermediate compounds for the methylidene compounds of the invention.

What is claimed is:

1. An aromatic methylidene compound selected from the group consisting of compounds of the following general formulas (1), (1a), (1b), (1c) and (1d):

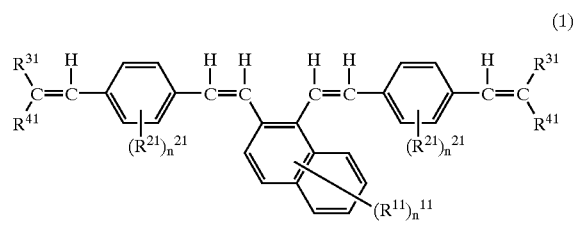

(1)

wherein $R^{11}$ and $R^{21}$ independently in each occurrence represent an unsubstituted or substituted alkyl group, an unsubstituted or substituted alkoxy group, a halogen, a cyano group or a nitro group, $n^{11}$ is an integer of 0, 1, 2, 3, 4, 5 or 6, and $n^{21}$ is an integer of 0, 1, 2, 3 or 4, provided that when $n^{11}$ and $n^{21}$ are, respectively, an integer of 2 or more, $R^{11}$'s and $R^{21}$'s may be, respectively, the same or different, and $R^{31}$ and $R^{41}$ independently represent hydrogen except the case where both $R^{31}$ and $R^{41}$ are hydrogen at the same time, an unsubstituted or substituted alkyl group except the case where both $R^{31}$ and $R^{41}$ are an alkyl group at the same time, an unsubstituted or substituted cycloalkyl group except the case where both $R^{31}$ and $R^{41}$ are the cycloalkyl group at the same time, an unsubstituted or substituted aromatic group, or an unsubstituted or substituted aromatic heterocyclic group and may join to complete a condensed ring of unsubstituted or substituted aromatic rings or unsubstituted or substituted aromatic heterocyclic rings;

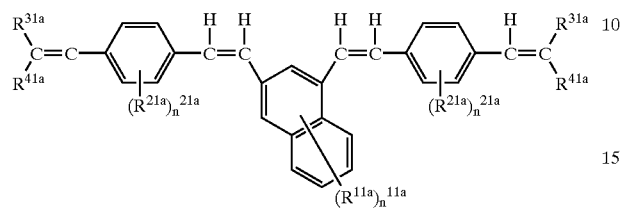

(1a)

wherein $R^{11a}$, $R^{21a}$, $n^{11a}$, $n^{21a}$, $R^{31a}$ and $R^{41a}$, respectively, have the same meanings as $R^{11}$, $R^{21}$, $n^{11}$, $n^{21}$, $R^{31}$ and $R^{41}$ defined with respect to the formula (1);

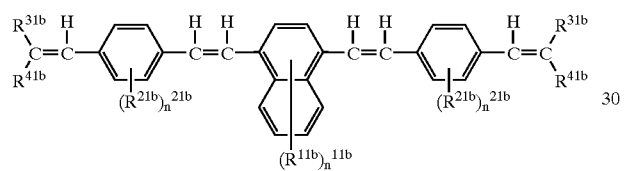

(1b)

wherein $R^{11b}$, $R^{21b}$, $n^{11b}$, $n^{21b}$, $R^{31b}$ and $R^{41b}$, respectively, have the same meanings as $R^{11}$, $R^{21}$, $n^{11}$, $n^{21}$, $R^{31}$ and $R^{41}$ defined with respect to the formula (1);

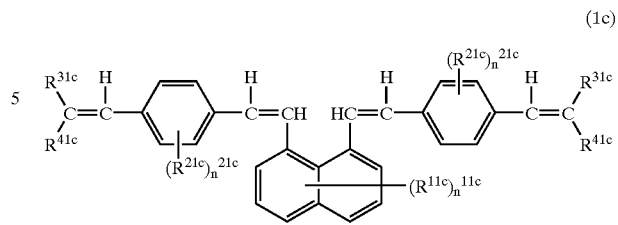

(1c)

wherein $R^{11c}$, $R^{21c}$, $n^{11c}$, $n^{21c}$, $R^{31c}$ and $R^{41c}$, respectively, have the same meanings as $R^{11}$, $R^{21}$, $n^{11}$, $n^{21}$, $R^{31}$ and $R^{41}$ defined with respect to the formula (1); and

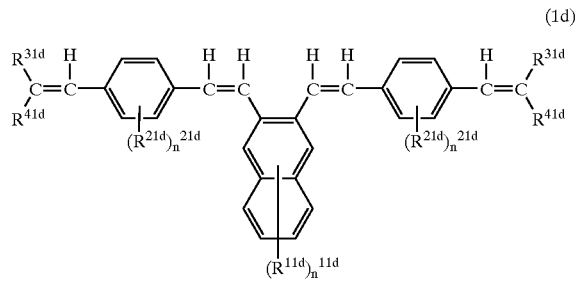

(1d)

wherein $R^{11d}$, $R^{21d}$, $n^{11d}$, $n^{21d}$, $R^{31d}$ and $R^{41d}$, respectively, have the same meanings as $R^{11}$, $R^{21}$, $n^{11}$, $n^{21}$, $R^{31}$ and $R^{41}$ defined with respect to the formula (1).

2. An aromatic methylidene compound according to claim 1, wherein said aromatic methylidene compound consists of the compound of the general formula (1).

3. An aromatic methylidene compound according to claim 2, wherein $R^{11}$ and $R^{21}$, respectively, represent phenyl.

4. An aromatic methylidene compound according to claim 2, wherein $n^{11}$ and $n^{21}$ are, respectively, zero.

5. An aromatic methylidene compound according to claim 2, wherein said aromatic methylidene compound is of the following formula:

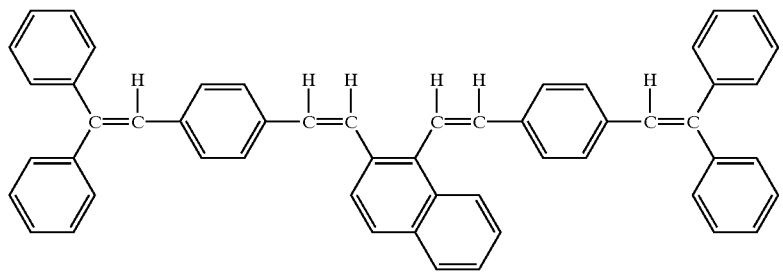

6. A method for preparing an aromatic methylidene compound defined in claim 2, which method comprises reacting a bismethylphosphonic ester derivative of the following formula (4), or a corresponding methyl triarylphosphonium compound thereof, with a benzaldehyde derivative of the following formula (5);

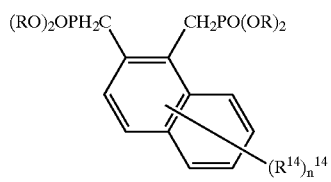
(4)

wherein $R^{14}$ represents an unsubstituted or substituted alkyl group, an unsubstituted or substituted alkoxy group, a halogen group, a cyano group or a nitro group, $n^{14}$ is an integer of 0, 1, 2, 3, 4, 5 or 6 provided that if $n^{14}$ is an integer of 2 or over, $R^{14}$'s may be the same or different, and R represents an unsubstituted or substituted alkyl group having from 1 to 4 carbon atoms; and

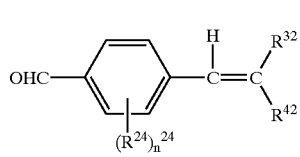
(5)

wherein $R^{24}$ represents an unsubstituted or substituted alkyl group, an unsubstituted or substituted alkoxy group, a halogen group, a cyano group or a nitro group, $n^{24}$ is an integer of 0, 1, 2, 3, 4, 5 or 6 provided that if $n^{24}$ is an integer of 2 or over, $R^{24}$'s may be the same or different, and $R^{32}$ and $R^{42}$, respectively, have the same meanings as $R^{31}$ and $R^{41}$ defined in the formula (1) and independently represent hydrogen except the case where both $R^{32}$ and $R^{42}$ are hydrogen at the same time, an unsubstituted or substituted alkyl group except the case where both $R^{32}$ and $R^{42}$ are an alkyl group at the same time, an unsubstituted or substituted cycloalkyl group except the case where both $R^{32}$ and $R^{42}$ are the cycloalkyl group at the same time, an unsubstituted or substituted aromatic group, or an unsubstituted or substituted aromatic heterocyclic group and may join to complete a condensed ring of unsubstituted or substituted aromatic rings or unsubstituted or substituted aromatic heterocyclic rings.

7. A method for preparing an aromatic methylidene compound defined in claim 2, which method comprises reacting a bis(4-formylstyryl)naphthalene derivative of the following general formula (2) with a methylphosphonic ester derivative of the following general formula (6) or a corresponding methyl triarylphosphonium compound thereof:

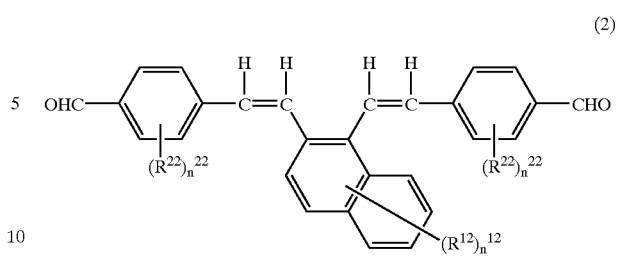
(2)

wherein $R^{12}$ and $R^{22}$, respectively, correspond to $R^{11}$ and $R^{21}$ and independently in each occurrence represent an unsubstituted or substituted alkyl group, an unsubstituted or substituted alkoxy group, a halogen, a cyano group or a nitro group, $n^{12}$ is an integer of 0, 1, 2, 3, 4, 5 or 6, and $n^{22}$ is an integer of 0, 1, 2, 3 or 4 provided that when $n^{12}$ and $n^{22}$ are, respectively, an integer of 2 or more, $R^{12}$'s and $R^{22}$'s may be, respectively, the same or different; and

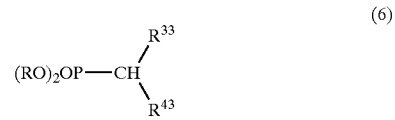
(6)

wherein $R^{33}$ and $R^{43}$, respectively, have the same meanings as $R^{31}$ and $R^{41}$ in the formula (1), and R represents an unsubstituted or substituted alkyl group having from 1 to 4 carbon atoms.

8. A method for preparing an aromatic methylidene compound defined in claim 2, which method comprises reacting a phthalaldehyde derivative of the following general formula (7) with a methylphosphonic ester derivative of the following general formula (8), or a corresponding methyl triarylphosphonium compound thereof:

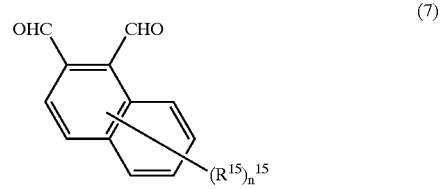
(7)

wherein $R^{15}$ has the same meaning as $R^{11}$ defined in the formula (1) and $n^{15}$ has the same meaning as $n^{11}$ provided that when $n^{15}$ is 2 or over, $R^{15}$'s may be the same or different; and

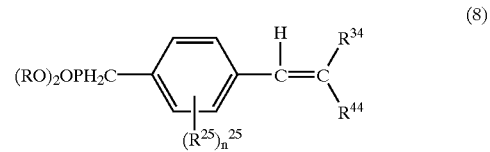
(8)

wherein $R^{25}$ has the same meaning as $R^{21}$ defined in the formula (1), $n^{25}$ is an integer of 0, 1, 2, 3 or 4 provided that if $n^{25}$ is 2 or over, $R^{25}$'s may be the same or different, $R^{34}$ and $R^{44}$, respectively, have the same meanings as $R^{31}$ and $R^{41}$, and R represents an unsubstituted or substituted alkyl group having from 1 to 4 carbon atoms.

9. A method for preparing an aromatic methylidene compound defined in claim 2, which method comprises reacting a bismethylphosphonic ester derivative of the following general formula (9), or a corresponding methyl triarylphosphonium compound thereof, with a ketone derivative of the following general formula (10):

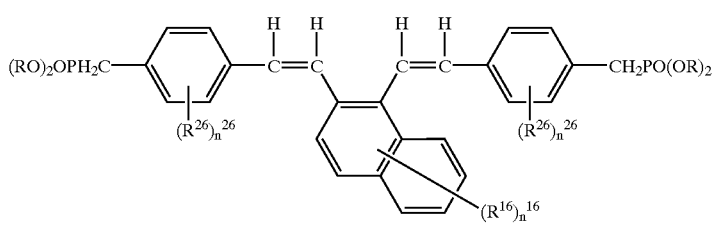
(9)

wherein $R^{16}$ and $R^{26}$, respectively, have the same meanings as $R^{11}$ and $R^{21}$ defined in the formula (1) and $n^{16}$ is an integer of 0, 1, 2, 3, 4, 5, or 6 and $n^{26}$ is an integer of 0, 1, 2, 3 or 4 provided that if $n^{16}$ and $n^{26}$, respectively, are 2 or over, $R^{16}$'s and $R^{26}$'s may be the same or different, and R represents an unsubstituted or substituted alkyl group having from 1 to 4 carbon atoms; and

(10)

wherein $R^{35}$ and $R^{45}$, respectively, have the same meanings as $R^{31}$ and $R^{41}$ defined in the formula (1).

10. A method for preparing an aromatic methylidene compound defined in claim 2, which method comprises reacting the bismethylphosphonic ester derivative of the following formula (4) with an aldehyde compound of the following general formula (11):

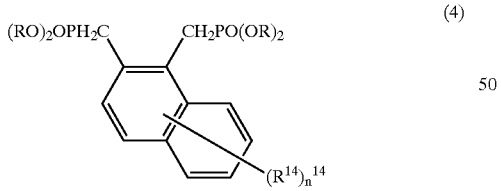
(4)

wherein $R^{14}$ and $n^{14}$, respectively, have the same meanings as defined in claim 6; and

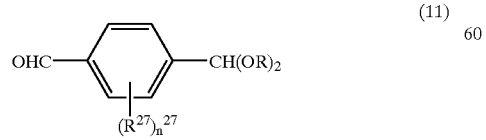
(11)

wherein $R^{27}$ represents a unsubstituted or substituted alkyl group, an unsubstituted or substituted alkyl group, a halogen atom, a cyano group or a nitro group, $n^{27}$ is an integer of 0, 1, 2, 3 or 4 provided that if $n^{27}$ is 2 or over, $R^{27}$'s may be the same or different, and R represents an unsubstituted or substituted alkyl group having from 1 to 4 carbon atoms, followed by conversion of the resultant acetal compound into an aldehyde compound.

11. An aromatic methylidene compound according to claim 1, wherein said aromatic methylidene compound consists of the compound of the general formula (1a).

12. A method for preparing an aromatic methylidene compound defined in claim 11, which method comprises reacting a bismethylphosphonic ester derivative of the following formula (4a), or a corresponding methyl triarylphosphonium compound thereof, with a benzaldehyde derivative of the following formula (5a);

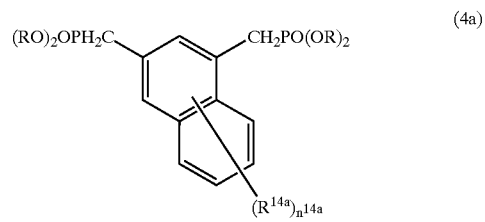
(4a)

wherein $R^{14a}$, $n^{14a}$, $R^{24a}$, $n^{24a}$, $R^{32a}$ and $R^{42a}$, respectively, have the same meanings as $R^{14}$, $n^{14}$, $R^{24}$, $n^{24}$, $R^{32}$ and $R^{42}$ defined in claim 6, and $R^{14a}$ represents an unsubstituted or substituted alkyl group, an unsubstituted or substituted alkoxy group, a halogen group, a cyano group or a nitro group, $n^{14a}$ is an integer of 0, 1, 2, 3, 4, 5 or 6 provided that if $n^{14a}$ is an integer of 2 or over, $R^{14a}$'s may be the same or different, and R represents an unsubstituted or substituted alkyl group having from 1 to 4 carbon atoms; and

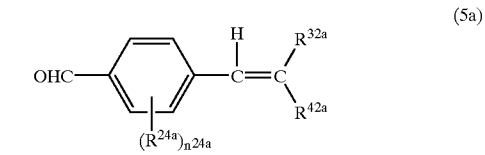
(5a)

wherein $R^{24a}$ represents an unsubstituted or substituted alkyl group, an unsubstituted or substituted alkoxy group, a halogen group, a cyano group or a nitro group, $n^{24a}$ is an integer of 0, 1, 2, 3 or 4 provided that if $n^{24a}$ is an integer of 2 or over, $R^{24a}$'s may be the same or different, and $R^{32a}$ and $R^{42a}$ independently represent hydrogen except the case where both $R^{32a}$ and $R^{42a}$ are hydrogen at the same time, an unsubstituted or substituted alkyl group except the case where both $R^{32a}$ and $R^{42a}$ are an alkyl group at the same time, an unsubstituted or substituted cycloalkyl group except the case where both $R^{32a}$ and $R^{42a}$ are the cycloalkyl group at the same time, an unsubstituted or substituted aromatic group, or an unsubstituted or substituted aromatic heterocyclic group and may join to complete a condensed ring of unsubstituted or substituted aromatic rings or unsubstituted or substituted aromatic heterocyclic rings.

13. A method for preparing an aromatic methylidene compound defined in claim 11, which method comprises reacting a bis(4-formylstyryl)naphthalene derivative of the following general formula (2a) with a methylphosphonic ester derivative of the following general formula (6a) or a corresponding methyl triarylphosphonium compound thereof:

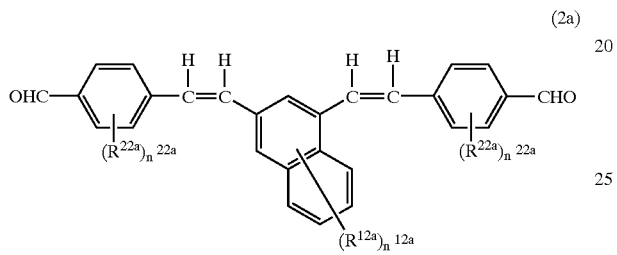

(2a)

wherein $R^{12a}$ and $R^{22a}$ independently in each occurrence represent an unsubstituted or substituted alkyl group, an unsubstituted or substituted alkoxy group, a halogen, a cyano group or a nitro group, $n^{12a}$ is an integer of 0, 1, 2, 3, 4, 5 or 6, and $n^{22a}$ is an integer of 0, 1, 2, 3 or 4 provided that when $n^{12a}$ and $n^{22a}$ are, respectively, an integer of 2 or more, $R^{12a}$'s and $R^{22a}$'s may be, respectively, the same or different; and

(6a)

wherein $R^{33a}$ and $R^{43a}$, respectively, have the same meanings as $R^{31}$ and $R^{41}$ defined in the formula (1), and independently represent hydrogen except the case where both $R^{33a}$ and $R^{43a}$ are hydrogen at the same time, an unsubstituted or substituted alkyl group except the case where both $R^{33a}$ and $R^{43a}$ are an alkyl group at the same time, an unsubstituted or substituted cycloalkyl group except the case where both $R^{33a}$ and $R^{43a}$ are the cycloalkyl group at the same time, an unsubstituted or substituted aromatic group, or an unsubstituted or substituted aromatic heterocyclic group and may join to complete a condensed ring of unsubstituted or substituted aromatic rings or unsubstituted or substituted aromatic heterocyclic rings, and R represents an unsubstituted or substituted alkyl group having 1 to 4 carbon atoms.

14. A method for preparing an aromatic methylidene compound defined in claim 11, which method comprises reacting a phthalaldehyde derivative of the following general formula (7a) with a methylphosphonic ester derivative of the following general formula (8a), or a corresponding methyl triarylphosphonium compound thereof:

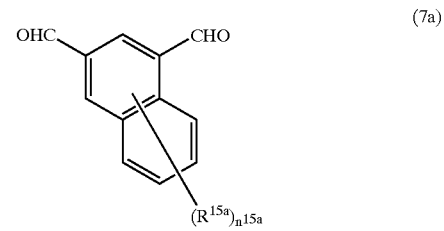

(7a)

wherein $R^{15a}$ independently represents an unsubstituted or substituted alkyl group, an unsubstituted or substituted alkoxy group, a halogen, a cyano group or a nitro group, $n^{15a}$ is an integer of 0, 1, 2, 3, 4, 5 or 6, provided that when $n^{15a}$ is 2 or over, $R^{15a}$'s may be the same or different; and

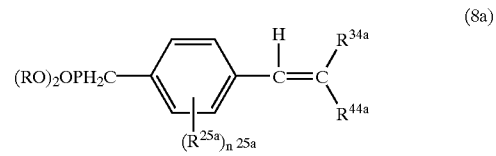

(8a)

wherein $R^{25a}$ independently represents an unsubstituted or substituted alkyl group, an unsubstituted or substituted alkoxy group, a halogen, a cyano group or a nitro group, $n^{25a}$ is an integer of 0, 1, 2, 3 or 4 provided that if $n^{25a}$ is 2 or over, $R^{25a}$'s may be the same or different, $R^{34a}$ and $R^{44a}$, respectively, have the same meanings as $R^{32a}$ and $R^{42a}$ defined in claim 12, and R represents an unsubstituted or substituted alkyl group having from 1 to 4 carbon atoms.

15. A method for preparing an aromatic methylidene compound defined in claim 11, which method comprises reacting a bismethylphosphonic ester derivative of the following general formula (9a), or a corresponding methyl triarylphosphonium compound thereof, with a ketone derivative of the following general formula (10a):

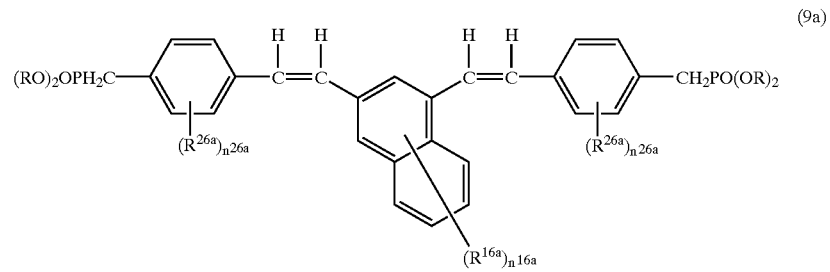

(9a)

wherein $R^{16a}$ and $R^{26a}$ independently in each occurrence represent an unsubstituted or substituted alkyl group, an unsubstituted or substituted alkoxy group, a halogen, a cyano group or a nitro group, $n^{16a}$ is an integer of 0, 1, 2, 3, 4, 5, or 6 and $n^{26a}$ is an integer of 0, 1, 2, 3 or 4 provided that if $n^{16a}$ and $n^{26a}$, respectively, are 2 or over, $R^{16a}$'s and $R^{26a}$'s may, respectively, be the same or different, and R represents an unsubstituted or substituted alkyl group having from 1 to 4 carbon atoms; and

(10a)

wherein $R^{35a}$ and $R^{45a}$, respectively, have the same meanings as $R^{32a}$ and $R^{42a}$ defined in claim 12.

16. An aromatic methylidene compound according to claim 1, wherein said aromatic methylidene compound consists of the compound of the general formula (1b).

17. A method for preparing an aromatic methylidene compound defined in claim 16, which method comprises reacting a bismethylphosphonic ester derivative of the following formula (4b), or a corresponding methyl triarylphosphonium compound thereof, with a benzaldehyde derivative of the following formula (5b);

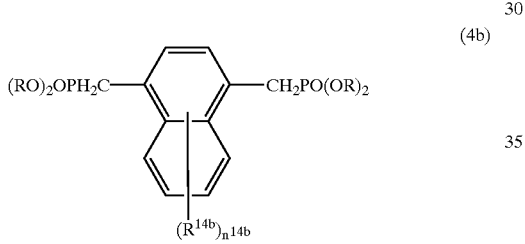
(4b)

wherein $R^{14b}$ represents an unsubstituted or substituted alkyl group, an unsubstituted or substituted alkoxy group, a halogen group, a cyano group or a nitro group, $n^{14b}$ is an integer of 0, 1, 2, 3, 4, 5 or 6 provided that if $n^{14b}$ is an integer of 2 or over, $R^{14b}$'s may be the same or different, and R represents an unsubstituted or substituted alkyl group having from 1 to 4 carbon atoms; and

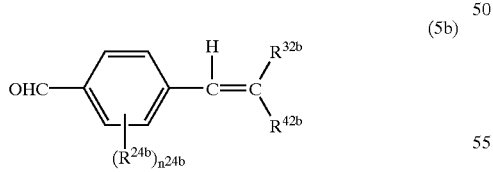
(5b)

wherein $R^{24b}$ represents an unsubstituted or substituted alkyl group, an unsubstituted or substituted alkoxy group, a halogen group, a cyano group or a nitro group, $n^{24b}$ is an integer of 0, 1, 2, 3 or 4 provided that if $n^{24b}$ is an integer of 2 or over, $R^{24b}$'s may be the same or different, and $R^{32b}$ and $R^{42b}$ independently represent hydrogen except the case where both $R^{32b}$ and $R^{42b}$ are hydrogen at the same time, an unsubstituted or substituted alkyl group except the case where both $R^{32b}$ and $R^{42b}$ are an alkyl group at the same time, an unsubstituted or substituted cycloalkyl group except the case where both $R^{32b}$ and $R^{42b}$ are the cycloalkyl group at the same time, an unsubstituted or substituted aromatic group, or an unsubstituted or substituted aromatic heterocyclic group and may join to complete a condensed ring of unsubstituted or substituted aromatic rings or unsubstituted or substituted aromatic heterocyclic rings.

18. A method for preparing an aromatic methylidene compound defined in claim 16, which method comprises reacting a bis(4-formylstyryl)naphthalene derivative of the following general formula (2b) with a methylphosphonic ester derivative of the following general formula (6b) or a corresponding methyl triarylphosphonium compound thereof:

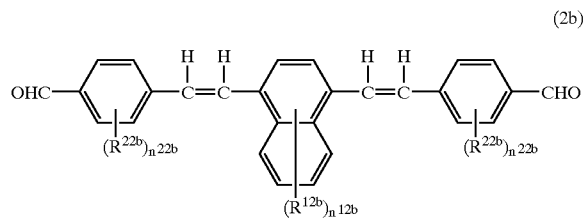
(2b)

wherein $R^{12b}$ and $R^{22b}$ independently in each occurrence represent an unsubstituted or substituted alkyl group, an unsubstituted or substituted alkoxy group, a halogen, a cyano group or a nitro group, $n^{12b}$ is an integer of 0, 1, 2, 3, 4, 5 or 6, and $n^{22b}$ is an integer of 0, 1, 2, 3 or 4 provided that when $n^{12b}$ and $n^{22b}$ are, respectively, an integer of 2 or more, $R^{12b}$'s and $R^{22b}$'s may be, respectively, the same or different; and

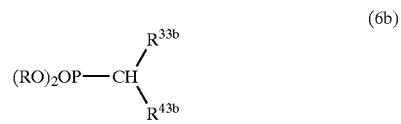
(6b)

wherein $R^{33b}$ and $R^{43b}$ independently represent hydrogen except the case where both $R^{33b}$ and $R^{43b}$ are hydrogen at the same time, an unsubstituted or substituted alkyl group except the case where both $R^{33b}$ and $R^{43b}$ are an alkyl group at the same time, an unsubstituted or substituted cycloalkyl group except the case where both $R^{33b}$ and $R^{43b}$ are the cycloalkyl group at the same time, an unsubstituted or substituted aromatic group, or an unsubstituted or substituted aromatic heterocyclic group and may join to complete a condensed ring of unsubstituted or substituted aromatic rings or unsubstituted or substituted aromatic heterocyclic rings, and R represents an unsubstituted or substituted alkyl group having 1 to 4 carbon atoms.

19. A method for preparing an aromatic methylidene compound defined in claim 16, which method comprises reacting a phthalaldehyde derivative of the following general formula (7b) with a methylphosphonic ester derivative of the following general formula (8b), or a corresponding methyl triarylphosphonium compound thereof:

(7b)

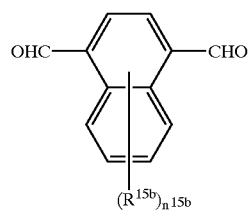

wherein $R^{15b}$ independently represents an unsubstituted or substituted alkyl group, an unsubstituted or substituted alkoxy group, a halogen, a cyano group or a nitro group, $n^{15b}$ is an integer of 0, 1, 2, 3, 4, 5 or 6, provided that when $n^{15b}$ is 2 or over, $R^{15b}$'s may be the same or different; and (8b)

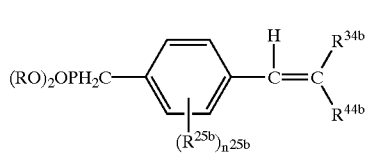

wherein $R^{25b}$ independently represents an unsubstituted or substituted alkyl group, an unsubstituted or substituted alkoxy group, a halogen, a cyano group or a nitro group, $n^{25b}$ is an integer of 0, 1, 2, 3 or 4 provided that if $n^{25b}$ is 2 or over, $R^{25b}$'s maybe the same or different, $R^{34b}$ and $R^{44b}$ independently represent hydrogen except the case where both $R^{34b}$ and $R^{44b}$ are hydrogen at the same time, an unsubstituted or substituted alkyl group except the case where both $R^{34b}$ and $R^{44b}$ are an alkyl group at the same time, an unsubstituted or substituted cycloalkyl group except the case where both $R^{34b}$ and $R^{44b}$ are the cycloalkyl group at the same time, an unsubstituted or substituted aromatic group, or an unsubstituted or substituted aromatic heterocyclic group and may join to complete a condensed ring of unsubstituted or substituted aromatic rings or unsubstituted or substituted aromatic heterocyclic rings, and R represents an unsubstituted or substituted alkyl group having from 1 to 4 carbon atoms.

20. A method for preparing an aromatic methylidene compound defined in claim 16, which method comprises reacting a bismethylphosphonic ester derivative of the following general formula (9b), or a corresponding methyl triarylphosphonium compound thereof, with a ketone derivative of the following general formula (10b):

(9b)

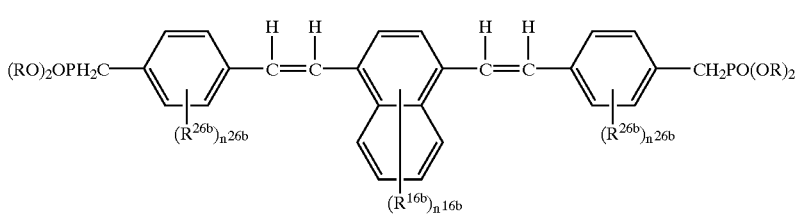

wherein $R^{16b}$ and $R^{26b}$ independently in each occurrence represent an unsubstituted or substituted alkyl group, an unsubstituted or substituted alkoxy group, a halogen, a cyano group or a nitro group, $n^{16b}$ is an integer of 0, 1, 2, 3, 4, 5, or 6 and $n^{26b}$ is an integer of 0, 1, 2, 3 or 4 provided that if $n^{16b}$ and $n^{26b}$, respectively, are 2 or over, $R^{16b}$'s and $R^{26b}$'s may be the same or different, and R represents an unsubstituted or substituted alkyl group; and (10b)

wherein $R^{35b}$ and $R^{45b}$ independently represent hydrogen except the case where both $R^{34b}$ and $R^{44b}$ are hydrogen at the same time, an unsubstituted or substituted alkyl group except the case where both $R^{35b}$ and $R^{45b}$ are an alkyl group at the same time, an unsubstituted or substituted cycloalkyl group except the case where both $R^{35b}$ and $R^{45b}$ are the cycloalkyl group at the same time, an unsubstituted or substituted aromatic group, or an unsubstituted or substituted aromatic heterocyclic group and may join to complete a condensed ring of unsubstituted or substituted aromatic rings or unsubstituted or substituted aromatic heterocyclic rings, and R represents an unsubstituted or substituted alkyl group having from 1 to 4 carbon atoms.

21. An aromatic methylidene compound according to claim 1, wherein said aromatic methylidene compound consists of the compound of the general formula (1c).

22. A method for preparing an aromatic methylidene compound defined in claim 21, which method comprises reacting a bismethylphosphonic ester derivative of the following formula (4c), or a corresponding methyl triarylphosphonium compound thereof, with a benzaldehyde derivative of the following formula (5c);

(4c)

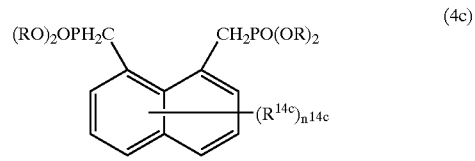

wherein $R^{14c}$ represents an unsubstituted or substituted alkyl group, an unsubstituted or substituted alkoxy group, a halogen group, a cyano group or a nitro group, $n^{14c}$ is an integer of 0, 1, 2, 3, 4, 5 or 6 provided that if $n^{14c}$ is an integer of 2 or over, $R^{14c}$'s may be the same or different, and R represents an unsubstituted or substituted alkyl group having from 1 to 4 carbon atoms; and

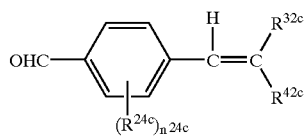

(5c)

wherein $R^{24c}$ represents an unsubstituted or substituted alkyl group, an unsubstituted or substituted alkoxy group, both as defined with respect to $R^{14c}$, a halogen group, a cyano group or a nitro group, $n^{24c}$ is an integer of 0, 1, 2, 3 or 4 provided that if $n^{24c}$ is an integer of 2 or over, $R^{24c}$'s may be the same or different, and $R^{32c}$ and $R^{42c}$ independently represent hydrogen except the case where both $R^{32c}$ and $R^{42c}$ are hydrogen at the same time, an unsubstituted or substituted alkyl group except the case where both $R^{32c}$ and $R^{42c}$ are an alkyl group at the same time, an unsubstituted or substituted cycloalkyl group except the case where both $R^{32c}$ and $R^{42c}$ are the cycloalkyl group at the same time, an unsubstituted or substituted aromatic group, or an unsubstituted or substituted aromatic heterocyclic group and may join to complete a condensed ring of unsubstituted or substituted aromatic rings or unsubstituted or substituted aromatic heterocyclic rings.

23. A method for preparing an aromatic methylidene compound defined in claim 21, which method comprises reacting a bis(4-formylstyryl)naphthalene derivative of the following general formula (2c) with a methylphosphonic ester derivative of the following general formula (6c) or a corresponding methyl triarylphosphonium compound thereof:

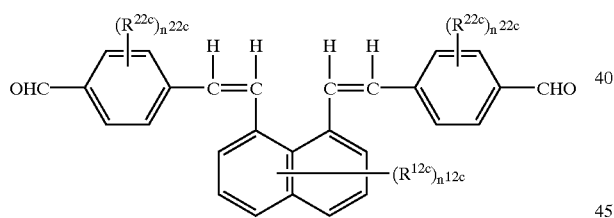

(2c)

wherein $R^{12c}$ and $R^{22c}$ independently in each occurrence represent an unsubstituted or substituted alkyl group, an unsubstituted or substituted alkoxy group, a halogen, a cyano group or a nitro group, $n^{12c}$ is an integer of 0, 1, 2, 3, 4, 5 or 6, and $n^{22c}$ is an integer of 0, 1, 2, 3 or 4 provided that when $n^{12c}$ and $n^{22c}$ are, respectively, an integer of 2 or more, $R^{12c}$'s and $R^{22c}$'s may be, respectively, the same or different; and

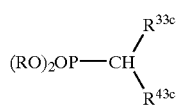

(6c)

wherein $R^{33c}$ and $R^{43c}$ independently represent hydrogen except the case where both $R^{33c}$ and $R^{43c}$ are hydrogen at the same time, an unsubstituted or substituted alkyl group except the case where both $R^{33c}$ and $R^{43c}$ are an alkyl group at the same time, an unsubstituted or substituted cycloalkyl group except the case where both $R^{33c}$ and $R^{43c}$ are the cycloalkyl group at the same time, an unsubstituted or substituted aromatic group, or an unsubstituted or substituted aromatic heterocyclic group and may join to complete a condensed ring of unsubstituted or substituted aromatic rings or unsubstituted or substituted aromatic heterocyclic rings, and R represents an unsubstituted or substituted alkyl group having from 1 to 4 carbon atoms.

24. A method for preparing an aromatic methylidene compound defined in claim 21, which method comprises reacting a phthalaldehyde derivative of the following general formula (7c) with a methylphosphonic ester derivative of the following general formula (8c), or a corresponding methyl triarylphosphonium compound thereof:

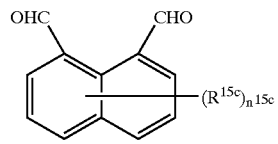

(7c)

wherein $R^{15c}$ independently represents an unsubstituted or substituted alkyl group, an unsubstituted or substituted alkoxy group, a halogen, a cyano group or a nitro group, $n^{15c}$ is an integer of 0, 1, 2, 3, 4, 5 or 6, provided that when $n^{15c}$ is 2 or over, $R^{15c}$'s maybe the same or different; and

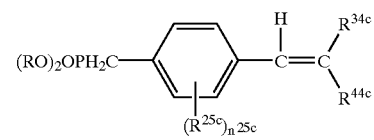

(8c)

wherein $R^{25c}$ independently represents an unsubstituted or substituted alkyl group, an unsubstituted or substituted alkoxy group, a halogen, a cyano group or a nitro group, $n^{25c}$ is an integer of 0, 1, 2, 3 or 4 provided that if $n^{25c}$ is 2 or over, $R^{25c}$'s maybe the same or different, $R^{34c}$ and $R^{44c}$ independently represent hydrogen except the case where both $R^{34c}$ and $R^{44c}$ are hydrogen at the same time, an unsubstituted or substituted alkyl group except the case where both $R^{34c}$ and $R^{44c}$ are an alkyl group at the same time, an unsubstituted or substituted cycloalkyl group except the case where both $R^{34c}$ and $R^{44c}$ are the cycloalkyl group at the same time, an unsubstituted or substituted aromatic group, or an unsubstituted or substituted aromatic heterocyclic group and may join to complete a condensed ring of unsubstituted or substituted aromatic rings or unsubstituted or substituted aromatic heterocyclic rings, and R represents an unsubstituted or substituted alkyl group having from 1 to 4 carbon atoms.

25. A method for preparing an aromatic methylidene compound defined in claim 21, which method comprises reacting a bismethylphosphonic ester derivative of the following general formula (9c), or a corresponding methyl triarylphosphonium compound thereof, with a ketone derivative of the following general formula (10c):

(9c)

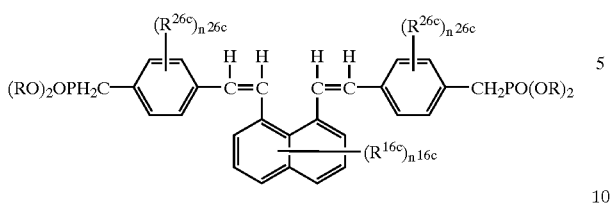

wherein $R^{16c}$ and $R^{26c}$ independently in each occurrence represent an unsubstituted or substituted alkyl group, an unsubstituted or substituted alkoxy group, a halogen, a cyano group or a nitro group, $n^{16c}$ is an integer of 0, 1, 2, 3, 4, 5, or 6 and $n^{26c}$ is an integer of 0, 1, 2, 3 or 4 provided that if $n^{16c}$ and $n^{26c}$, respectively, are 2 or over, $R^{16c}$'s and $R^{26c}$'s may be the same or different, and R represents an unsubstituted or substituted alkyl group having from 1 to 4 carbon atoms; and (10c)

wherein $R^{35c}$ and $R^{45c}$ independently represent hydrogen except the case where both $R^{34c}$ and $R^{44c}$ are hydrogen at the same time, an unsubstituted or substituted alkyl group except the case where both $R^{35c}$ and $R^{45c}$ are an alkyl group at the same time, an unsubstituted or substituted cycloalkyl group except the case where both $R^{35c}$ and $R^{45c}$ are the cycloalkyl group at the same time, an unsubstituted or substituted aromatic group, or an unsubstituted or substituted aromatic heterocyclic group and may join to complete a condensed ring of unsubstituted or substituted aromatic rings or unsubstituted or substituted aromatic heterocyclic rings, and R represents an unsubstituted or substituted alkyl group having from 1 to 4 carbon atoms.

26. An aromatic methylidene compound according to claim 1, wherein said aromatic methylidene compound consists of the compound of the general formula (1d).

27. A method for preparing an aromatic methylidene compound defined in claim 26, which method comprises reacting a bismethylphosphonic ester derivative of the following formula (4d), or a corresponding methyl triarylphosphonium compound thereof, with a benzaldehyde derivative of the following formula (5d):

(4d)

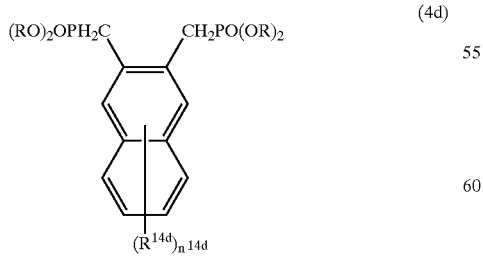

wherein $R^{14d}$ represents an unsubstituted or substituted alkyl group, an unsubstituted or substituted alkoxy group, a halogen group, a cyano group or a nitro group, $n^{14c}$ is an integer of 0, 1, 2, 3, 4, 5 or 6 provided that if $n^{14d}$ is an integer of 2 or over, $R^{14d}$'s maybe the same or different, and R represents an unsubstituted or substituted alkyl group having from 1 to 4 carbon atoms; and (5d)

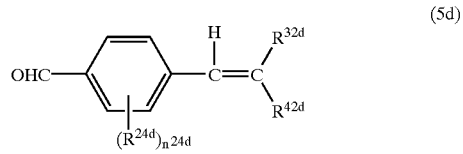

wherein $R^{24d}$ represents an unsubstituted or substituted alkyl group, an unsubstituted or substituted alkoxy group, a halogen group, a cyano group or a nitro group, $n^{24d}$ is an integer of 0, 1, 2, 3 or 4 provided that if $n^{24d}$ is an integer of 2 or over, $R^{24d}$'s may be the same or different, and $R^{32d}$ and $R^{42d}$ independently represent hydrogen except the case where both $R^{32d}$ and $R^{42d}$ are hydrogen at the same time, an unsubstituted or substituted alkyl group except the case where both $R^{32d}$ and $R^{42d}$ are an alkyl group at the same time, an unsubstituted or substituted cycloalkyl group except the case where both $R^{32d}$ and $R^{42d}$ are the cycloalkyl group at the same time, an unsubstituted or substituted aromatic group, or an unsubstituted or substituted aromatic heterocyclic group and may join to complete a condensed ring of unsubstituted or substituted aromatic rings or unsubstituted or substituted aromatic heterocyclic rings.

28. A method for preparing an aromatic methylidene compound defined in claim 26, which method comprises reacting a bis(4-formylstyryl)naphthalene derivative of the following general formula (2d) with a methylphosphonic ester derivative of the following general formula (6d) or a corresponding methyl triarylphosphonium compound thereof:

(2d)

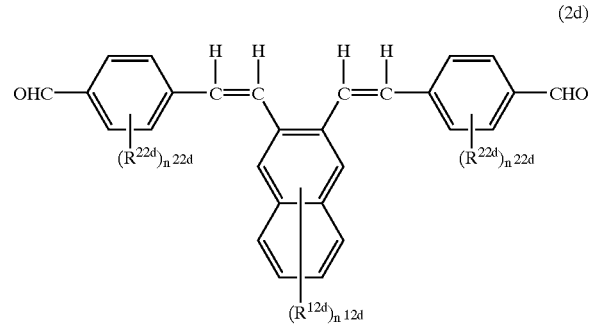

wherein $R^{12d}$ and $R^{22d}$ independently in each occurrence represent an unsubstituted or substituted alkyl group, an unsubstituted or substituted alkoxy group, a halogen, a cyano group or a nitro group, $n^{12d}$ is an integer of 0, 1, 2, 3, 4, 5 or 6, and $n^{22b}$ is an integer of 0, 1, 2, 3 or 4 provided that when $n^{12d}$ and $n^{22d}$ are, respectively, an integer of 2 or more, $R^{12d}$'s and $R^{22d}$'s may be, respectively, the same or different; and

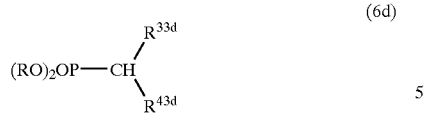

(6d)

wherein $R^{33d}$ and $R^{43d}$ may be the same or different and independently represent hydrogen except the case where both $R^{33d}$ and $R^{43d}$ are hydrogen at the same time, an unsubstituted or substituted alkyl group except the case where both $R^{33d}$ and $R^{43d}$ are an alkyl group at the same time, an unsubstituted or substituted cycloalkyl group except the case where both $R^{33d}$ and $R^{43d}$ are the cycloalkyl group at the same time, an unsubstituted or substituted aromatic group, or an unsubstituted or substituted aromatic heterocyclic group and may join to complete a condensed ring of unsubstituted or substituted aromatic rings or unsubstituted or substituted aromatic heterocyclic rings, and R represents an unsubstituted or substituted alkyl group having from 1 to 4 carbon atoms.

29. A method for preparing an aromatic methylidene compound defined in claim 26, which method comprises reacting a phthalaldehyde derivative of the following general formula (7d) with a methylphosphonic ester derivative of the following general formula (8d), or a corresponding methyl triarylphosphonium compound thereof:

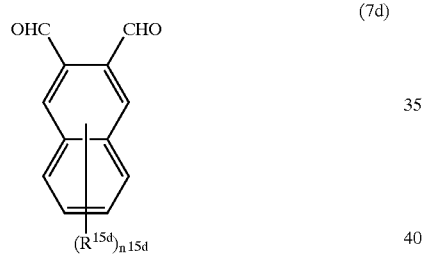

(7d)

wherein $R^{15d}$ independently represents an unsubstituted or substituted alkyl group, an unsubstituted or substituted alkoxy group, a halogen, a cyano group or a nitro group, $n^{15d}$ is an integer of 0, 1, 2, 3, 4, 5 or 6, provided that when $n^{15d}$ is 2 or over, $R^{15d}$'s may be the same or different; and

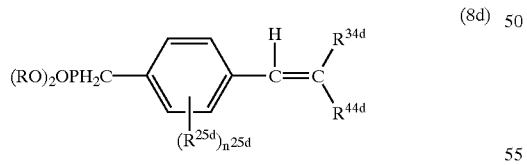

(8d)

wherein $R^{25d}$ independently represents an unsubstituted or substituted alkyl group, an unsubstituted or substituted alkoxy group, a halogen, a cyano group or a nitro group, $n^{25d}$ is an integer of 0, 1, 2, 3 or 4 provided that if $n^{25d}$ is 2 or over, $R^{25d}$'s may be the same or different, $R^{34d}$ and $R^{44d}$ independently represent hydrogen except the case where both $R^{34d}$ and $R^{44d}$ are hydrogen at the same time, an unsubstituted or substituted alkyl group, except the case where both $R^{34d}$ and $R^{44d}$ are an alkyl group at the same time, an unsubstituted or substituted cycloalkyl group, except the case where both $R^{34d}$ and $R^{44d}$ are the cycloalkyl group at the same time, an unsubstituted or substituted aromatic group, or an unsubstituted or substituted aromatic heterocyclic group and may join to complete a condensed ring of unsubstituted or substituted aromatic rings or unsubstituted or substituted aromatic heterocyclic rings, and R represents an unsubstituted or substituted alkyl group having from 1 to 4 carbon atoms.

30. A method for preparing an aromatic methylidene compound defined in claim 26, which method comprises reacting a bismethylphosphonic ester derivative of the following general formula (9d), or a corresponding methyl triarylphosphonium compound thereof, with a ketone derivative of the following general formula (10d):

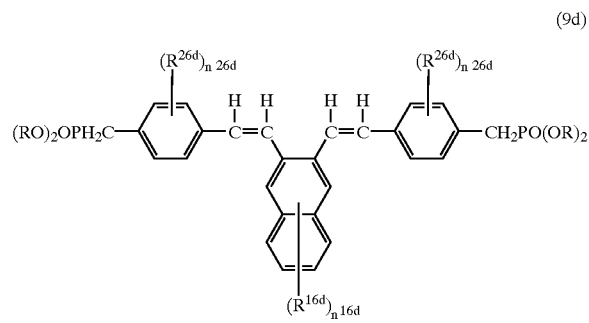

(9d)

wherein $R^{16d}$ and $R^{26d}$ independently in each occurrence represent an unsubstituted or substituted alkyl group, an unsubstituted or substituted alkoxy group, a halogen, a cyano group or a nitro group, $n^{16d}$ is an integer of 0, 1, 2, 3, 4, 5, or 6 and $n^{26d}$ is an integer of 0, 1, 2, 3 or 4 provided that if $n^{16d}$ and $n^{26d}$, respectively, are 2 or over, $R^{16d}$'s and $R^{26d}$'s may be the same or different, and R represents an unsubstituted or substituted alkyl group having from 1 to 4 carbon atoms; and

(10d)

wherein $R^{35d}$ and $R^{45d}$ independently represent hydrogen except the case where both $R^{34d}$ and $R^{44d}$ are hydrogen at the same time, an unsubstituted or substituted alkyl group except the case where both $R^{35d}$ and $R^{45d}$ are an alkyl group at the same time, an unsubstituted or substituted cycloalkyl group except the case where both $R^{35d}$ and $R^{45d}$ are the cycloalkyl group at the same time, an unsubstituted or substituted aromatic group, or an unsubstituted or substituted aromatic heterocyclic group and may join to complete a condensed ring of unsubstituted or substituted aromatic rings or unsubstituted or substituted aromatic heterocyclic rings, and R represents an unsubstituted or substituted alkyl group having from 1 to 4 carbon atoms.

31. A compound selected from the group consisting of compounds of the following general formulas (2), (2a), (2b), (2c) and (2d):

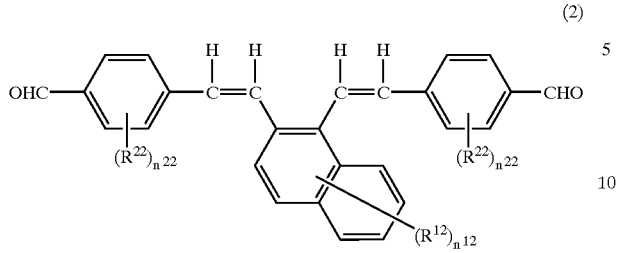

(2)

wherein $R^{12}$ and $R^{22}$ independently in each occurrence represent an unsubstituted or substituted alkyl group, an unsubstituted or substituted alkoxy group, a halogen, a cyano group or a nitro group, $n^{12}$ is an integer of 0, 1, 2, 3, 4, 5 or 6, and $n^{22}$ is an integer of 0, 1, 2, 3 or 4 provided that when $n^{12}$ and $n^{22}$ are, respectively, an integer of 2 or more, $R^{11}$'s and $R^{21}$'s may be, respectively, the same or different;

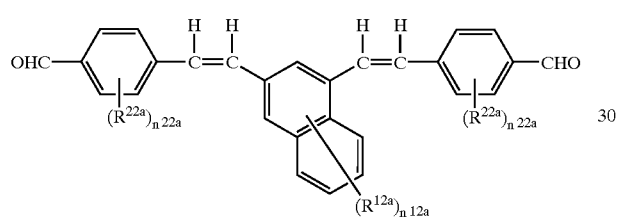

(2a)

wherein $R^{12a}$, $R^{22a}$, $n^{12a}$ and $n^{22a}$, respectively, have the same meanings as $R^{12}$, $R^{22}$, $n^{12}$ and $n^{22}$;

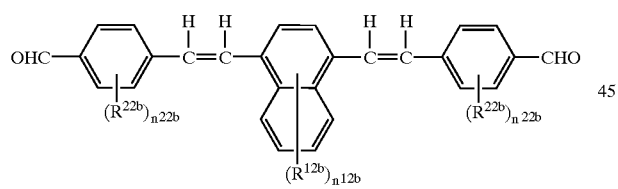

(2b)

wherein $R^{12b}$, $R^{22b}$, $n^{12b}$ and $n^{22b}$, respectively, have the same meanings as $R^{12}$, $R^{22}$ $n^{12}$ and $n^{22}$;

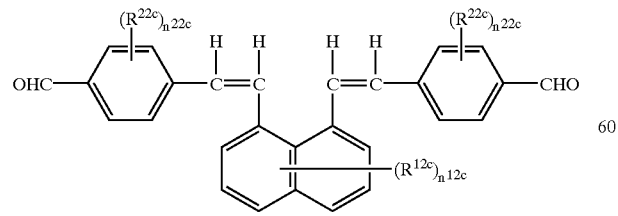

(2c)

wherein $R^{12c}$, $R^{22c}$, $n^{12c}$ and $n^{22c}$, respectively, have the same meanings as $R^{12}$, $R^{22}$ $n^{12}$ and $n^{22}$; and

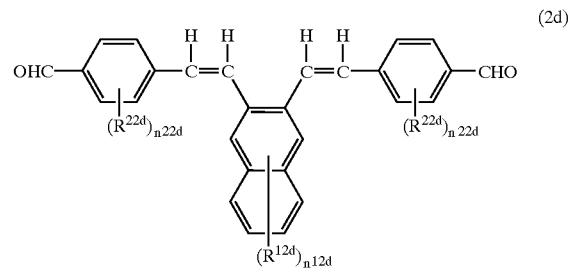

(2d)

wherein $R^{12bd}$, $R^{22d}$, $n^{12d}$ and $n^{22d}$, respectively, have the same meanings as $R^{12}$, $R^{22}$ $n^{12}$ and $n^{22}$.

32. A compound according to claim 31, wherein said compound consists of a compound of the general formula (2).

33. A method for preparing a compound of the general formula (2) defined in claim 32, which method comprises reacting the bismethylphosphonic ester derivative of the following formula (4), or a corresponding methyl triarylphosphonium compound thereof, with an aldehyde compound of the following general formula (11):

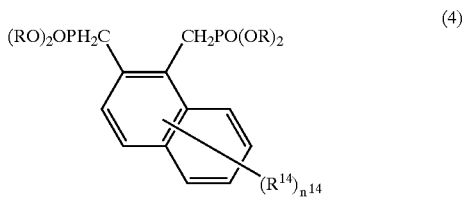

(4)

wherein $R^{14}$ represents an unsubstituted or substituted alkyl group, an unsubstituted or substituted alkoxy group, a halogen group, a cyano group or a nitro group, $n^{14}$ is an integer of 0, 1, 2, 3, 4, 5 or 6 provided that if $n^{14}$ is an integer of 2 or over, $R^{14}$'s may be the same or different, and R represents an unsubstituted or substituted alkyl group having from 1 to 4 carbon atoms; and

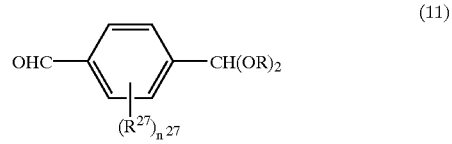

(11)

wherein $R^{27}$ represents a unsubstituted or substituted alkyl group, an unsubstituted or substituted alkyl group, a halogen atom, a cyano group or a nitro group, $n^{27}$ is an integer of 0, 1, 2, 3 or 4 provided that if $n^{27}$ is 2 or over, $R^{27}$'s may be the same or different, and R represents an unsubstituted or substituted alkyl group, followed by conversion of the resultant acetal compound into an aldehyde compound.

34. A method for preparing a compound of the general formula (2) defined in claim 32, which method comprises reacting the bismethylphosphonic ester derivative of the following formula (4), or a corresponding methyl triarylphosphonium compound thereof, with an aldehyde compound of the following general formula (12):

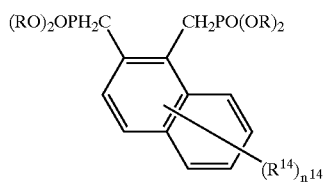

(4)

wherein $R^{14}$ represents an unsubstituted or substituted alkyl group, an unsubstituted or substituted alkoxy group, a halogen group, a cyano group or a nitro group, $n^{14}$ is an integer of 0, 1, 2, 3, 4, 5 or 6 provided that if $n^{14}$ is an integer of 2 or over, $R^{14}$'s may be the same or different, and R represents an unsubstituted or substituted alkyl group having from 1 to 4 carbon atoms; and

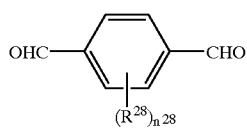

(12)

wherein $R^{28}$ represents a unsubstituted or substituted alkyl group, an unsubstituted or substituted alkyl group, a halogen atom, a cyano group or a nitro group, and $n^{28}$ is an integer of 0, 1, 2, 3 or 4 provided that if $n^{28}$ is 2 or over, $R^{28}$'s may be the same or different.

35. A compound according to claim 31, wherein said compound consists of a compound of the general formula (2a).

36. A method for preparing a compound of the general formula (2a) defined in claim 32, which method comprises reacting the bismethylphosphonic ester derivative of the following formula (4a), or a corresponding methyl triarylphosphonium compound thereof, with an aldehyde compound of the following general formula (11):

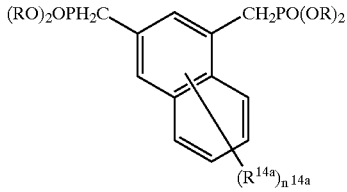

(4a)

wherein $R^{14a}$ represents an unsubstituted or substituted alkyl group, an unsubstituted or substituted alkoxy group, a halogen group, a cyano group or a nitro group, $n^{14a}$ is an integer of 0, 1, 2, 3, 4, 5 or 6 provided that if $n^{14a}$ is an integer of 2 or over, $R^{14a}$'s may be the same or different, and R represents an unsubstituted or substituted alkyl group having from 1 to 4 carbon atoms; and

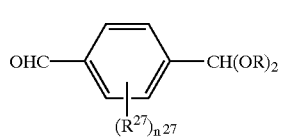

(11)

wherein $R^{27}$ represents a unsubstituted or substituted alkyl group, an unsubstituted or substituted alkyl group, a halogen atom, a cyano group or a nitro group, $n^{27}$ is an integer of 0, 1, 2, 3 or 4 provided that if $n^{27}$ is 2 or over, $R^{27}$'s may be the same or different, and R represents an unsubstituted or substituted alkyl group, followed by conversion of the resultant acetal compound into an aldehyde compound.

37. A method for preparing a compound of the general formula (2a) defined in claim 35, which method comprises reacting the bismethylphosphonic ester derivative of the following formula (4a), or a corresponding methyl triarylphosphonium compound thereof, with an aldehyde compound of the following general formula (12):

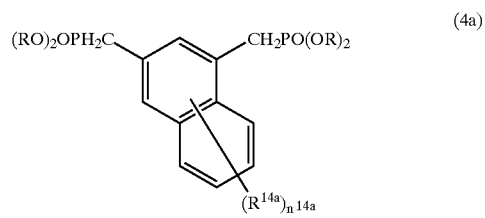

(4a)

wherein $R^{14a}$ represents an unsubstituted or substituted alkyl group, an unsubstituted or substituted alkoxy group, a halogen group, a cyano group or a nitro group, $n^{14a}$ is an integer of 0, 1, 2, 3, 4, 5 or 6 provided that if $n^{14a}$ is an integer of 2 or over, $R^{14a}$'s may be the same or different, and R represents an unsubstituted or substituted alkyl group having from 1 to 4 carbon atoms; and

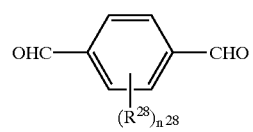

(12)

wherein $R^{28}$ represents a unsubstituted or substituted alkyl group, an unsubstituted or substituted alkyl group, a halogen atom, a cyano group or a nitro group, and $n^{28}$ is an integer of 0, 1, 2, 3 or 4 provided that if $n^{28}$ is 2 or over, $R^{28}$'s may be the same or different.

38. A compound according to claim 31, wherein said compound consists of a compound of the general formula (2b).

39. A method for preparing a compound of the general formula (2b) defined in claim 38, which method comprises reacting the bismethylphosphonic ester derivative of the following formula (4b), or a corresponding methyl triarylphosphonium compound thereof, with an aldehyde compound of the following general formula (11): (4b)

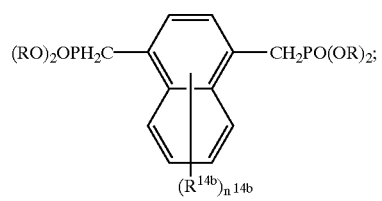

(4b)

wherein $R^{14b}$ represents an unsubstituted or substituted alkyl group, an unsubstituted or substituted alkoxy group, a halogen group, a cyano group or a nitro group, $n^{14b}$ is an integer of 0, 1, 2, 3, 4, 5 or 6 provided that if $n^{14b}$ is an integer of 2 or over, $R^{14b}$'s may be the same or different, and R represents an unsubstituted or substituted alkyl group having from 1 to 4 carbon atoms; and

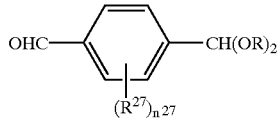
(11)

wherein $R^{27}$ represents a unsubstituted or substituted alkyl group, an unsubstituted or substituted alkyl group, a halogen atom, a cyano group or a nitro group, $n^{27}$ is an integer of 0, 1, 2, 3 or 4 provided that if $n^{27}$ is 2 or over, $R^{27}$'s may be the same or different, and R represents an unsubstituted or substituted alkyl group, followed by conversion of the resultant acetal compound into an aldehyde compound.

40. A method for preparing a compound of the general formula (2b) defined in claim 38, which method comprises reacting the bismethylphosphonic ester derivative of the following formula (4b), or a corresponding methyl triarylphosphonium compound thereof, with an aldehyde compound of the following general formula (12):

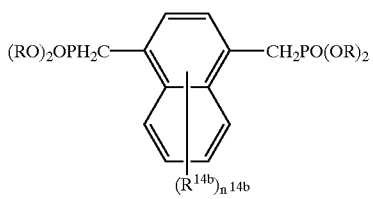
(4b)

wherein $R^{14b}$ represents an unsubstituted or substituted alkyl group, an unsubstituted or substituted alkoxy group, a halogen group, a cyano group or a nitro group, $n^{14b}$ is an integer of 0, 1, 2, 3, 4, 5 or 6 provided that if $n^{14b}$ is an integer of 2 or over, $R^{14b}$'s may be the same or different, and R represents an unsubstituted or substituted alkyl group having from 1 to 4 carbon atoms; and

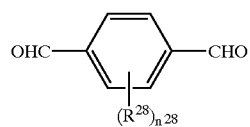
(12)

wherein $R^{28}$ represents a unsubstituted or substituted alkyl group, an unsubstituted or substituted alkyl group, a halogen atom, a cyano group or a nitro group, and $n^{28}$ is an integer of 0, 1, 2, 3 or 4 provided that if $n^{28}$ is 2 or over, $R^{28}$'s may be the same or different.

41. A compound according to claim 31, wherein said compound consists of a compound of the general formula (2c).

42. A method for preparing a compound of the general formula (2c) defined in claim 41, which method comprises reacting the bismethylphosphonic ester derivative of the following formula (4c), or a corresponding methyl triarylphosphonium compound thereof, with an aldehyde compound of the following general formula (11):

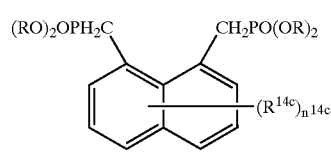
(4c)

wherein $R^{14c}$ represents an unsubstituted or substituted alkyl group, an unsubstituted or substituted alkoxy group, a halogen group, a cyano group or a nitro group, $n^{14c}$ is an integer of 0, 1, 2, 3, 4, 5 or 6 provided that if $n^{14c}$ is an integer of 2 or over, $R^{14c}$'s may be the same or different, and R represents an unsubstituted or substituted alkyl group having from 1 to 4 carbon atoms; and

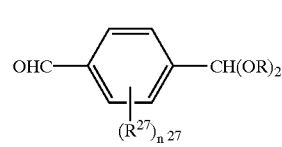
(11)

wherein $R^{27}$ represents a unsubstituted or substituted alkyl group, an unsubstituted or substituted alkyl group, a halogen atom, a cyano group or a nitro group, $n^{27}$ is an integer of 0, 1, 2, 3 or 4 provided that if $n^{27}$ is 2 or over, $R^{27}$'s may be the same or different, and R represents an unsubstituted or substituted alkyl group, followed by conversion of the resultant acetal compound into an aldehyde compound.

43. A method for preparing a compound of the general formula (2c) defined in claim 41, which method comprises reacting the bismethylphosphonic ester derivative of the following formula (4c), or a corresponding methyl triarylphosphonium compound thereof, with an aldehyde compound of the following general formula (12):

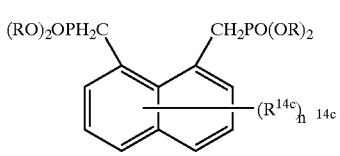
(4c)

wherein $R^{14c}$ represents an unsubstituted or substituted alkyl group, an unsubstituted or substituted alkoxy group, a halogen group, a cyano group or a nitro group, $n^{14c}$ is an integer of 0, 1, 2, 3, 4, 5 or 6 provided that if $n^{14c}$ is an integer of 2 or over, $R^{14c}$'s may be the same or different, and R represents an unsubstituted or substituted alkyl group having from 1 to 4 carbon atoms; and

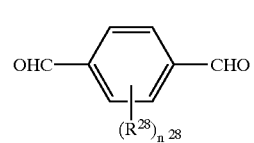
(12)

wherein $R^{28}$ represents a unsubstituted or substituted alkyl group, an unsubstituted or substituted alkyl group, a halogen atom, a cyano group or a nitro group, and $n^{28}$ is an integer of 0, 1, 2, 3 or 4 provided that if $n^{28}$ is 2 or over, $R^{28}$'s may be the same or different.

44. A compound according to claim 31, wherein said compound consists of a compound of the general formula (2d).

45. A method for preparing a compound of the general formula (2d) defined in claim 44, which method comprises reacting the bismethylphosphonic ester derivative of the following formula (4d), or a corresponding methyl tri-arylphosphonium compound thereof, with an aldehyde compound of the following general formula (11):

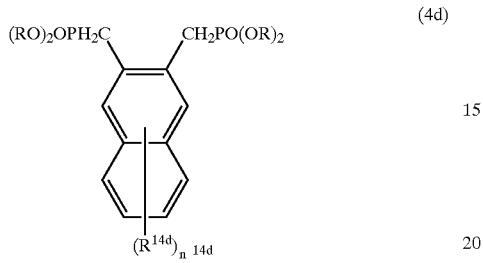
(4d)

wherein $R^{14d}$ represents an unsubstituted or substituted alkyl group, an unsubstituted or substituted alkoxy group, a halogen group, a cyano group or a nitro group, $n^{14d}$ is an integer of 0, 1, 2, 3, 4, 5 or 6 provided that if $n^{14d}$ is an integer of 2 or over, $R^{14d}$'s may be the same or different, and R represents an unsubstituted or substituted alkyl group having from 1 to 4 carbon atoms; and

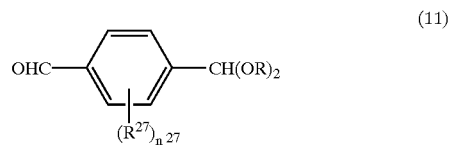
(11)

wherein $R^{27}$ represents a unsubstituted or substituted alkyl group, an unsubstituted or substituted alkyl group, a halogen atom, a cyano group or a nitro group, $n^{27}$ is an integer of 0, 1, 2, 3 or 4 provided that if $n^{27}$ is 2 or over, $R^{27}$'s may be the same or different, and R represents an unsubstituted or substituted alkyl group, followed by conversion of the resultant acetal compound into an aldehyde compound.

46. A method for preparing a compound of the general formula (2d) defined in claim 44, which method comprises reacting the bismethylphosphonic ester derivative of the following formula (4d), or a corresponding methyl tri-arylphosphonium compound thereof, with an aldehyde compound of the following general formula (12):

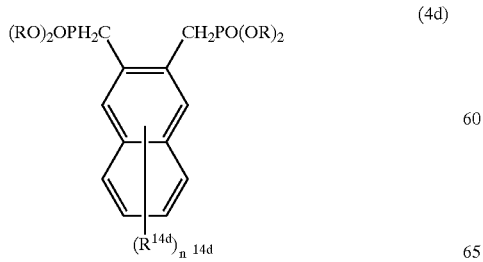
(4d)

wherein $R^{14d}$ represents an unsubstituted or substituted alkyl group, an unsubstituted or substituted alkoxy group, a halogen group, a cyano group or a nitro group, $n^{14d}$ is an integer of 0, 1, 2, 3, 4, 5 or 6 provided that if $n^{14d}$ is an integer of 2 or over, $R^{14d}$'s may be the same or different, and R represents an unsubstituted or substituted alkyl group having from 1 to 4 carbon atoms; and

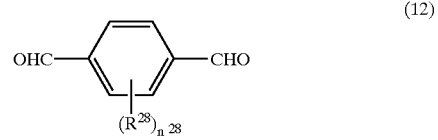
(12)

wherein $R^{28}$ represents a unsubstituted or substituted alkyl group, an unsubstituted or substituted alkyl group, a halogen atom, a cyano group or a nitro group, and $n^{28}$ is an integer of 0, 1, 2, 3 or 4 provided that if $n^{28}$ is 2 or over, $R^{28}$'s may be the same or different.

47. A compound selected from the group consisting of compounds of the following general formulas (3), (3a), (3b), (3c) and (3d):

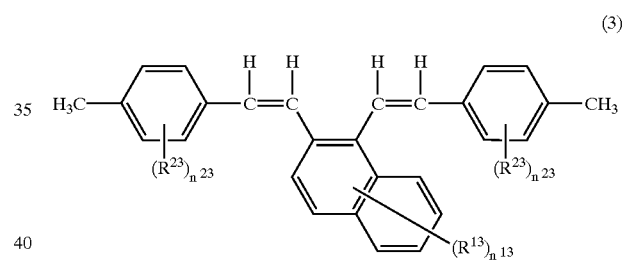
(3)

wherein $R^{13}$ and $R^{23}$ independently in each occurrence represent an unsubstituted or substituted alkyl group, an unsubstituted or substituted alkoxy group, a halogen, a cyano group or a nitro group, $n^{13}$ is an integer of 0, 1, 2, 3, 4, 5 or 6, and $n^{23}$ is an integer of 0, 1, 2, 3 or 4 that when $n^{13}$ and $n^{23}$ are, respectively, an integer of 2 or more, $R^{13}$"s and $R^{23}$'s may be, respectively, the same or different;

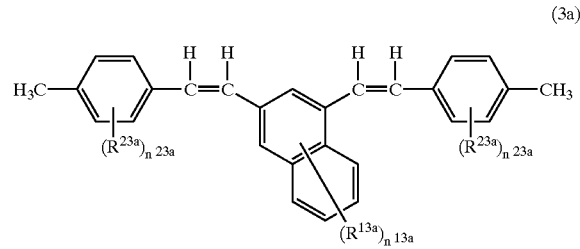
(3a)

wherein $R^{13a}$, $R^{23a}$, $n^{13a}$ and $n^{23a}$, respectively, have the same meanings as $R^{13}$, $R^{23}$ $n^{13}$ and $n^{23}$;

(3b)

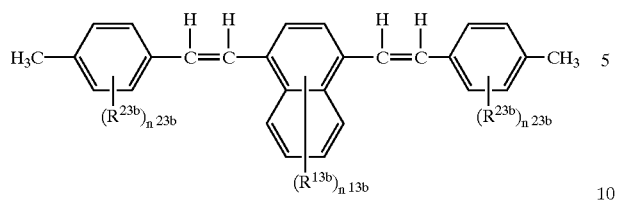

wherein $R^{13a}$, $R^{23a}$, $n^{13b}$ and $n^{23b}$, respectively, have the same meanings as $R^{13}$, $R^{23}$ $n^{13}$ and $n^{23}$;

(3c)

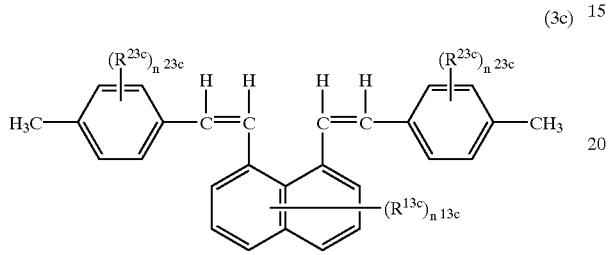

wherein $R^{13c}$, $R^{23c}$, $n^{13c}$ and $n^{23c}$, respectively, have the same meanings as $R^{13}$, $R^{23}$ $n^{13}$ and $n^{23}$; and (3d)

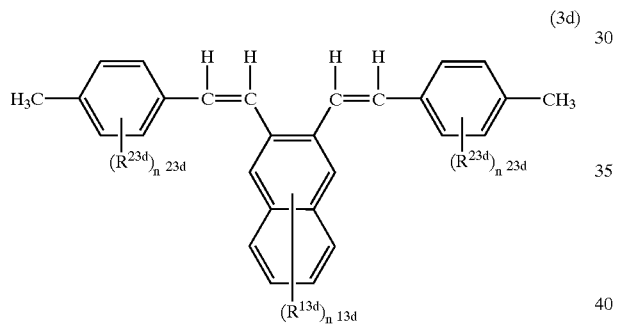

wherein $R^{13d}$ $R^{23d}$, $n^{13d}$ and $n^{23d}$, respectively, have the same meanings as $R^{13}$, $R^{23}$ $n^{13}$ and $n^{23}$.

48. A compound according to claim 47, wherein said compound consists of a compound of the general formula (3).

49. A method for preparing a compound of the general formula (3) defined in claim 48, which method comprises reacting the bismethylphosphonic ester derivative of the following formula (4), or a corresponding methyl triarylphosphonium compound thereof, with an aldehyde compound of the following general formula (13):

(4)

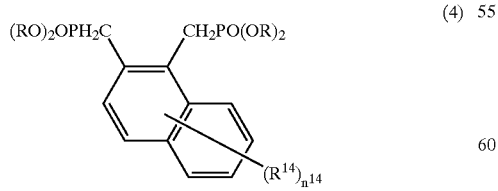

wherein $R^{14}$ represents an unsubstituted or substituted alkyl group, an unsubstituted or substituted alkoxy group, a halogen group, a cyano group or a nitro group, $n^{14}$ is an integer of 0, 1, 2, 3, 4, 5 or 6 provided that if $n^{14}$ is an integer of 2 or over, $R^{14}$'s maybe the same or different, and R represents an unsubstituted or substituted alkyl group having from 1 to 4 carbon atoms; and (13)

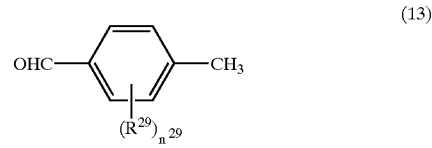

wherein $R^{29}$ represents an unsubstituted or substituted alkyl group, an unsubstituted or substituted alkoxy group, a halogen atom, a cyano group or a nitro group as defined as $R^{14}$ in the formula (4), and $n^{29}$ is an integer of 0, 1, 2, 3 or 4 provided that if $n^{29}$ is 2 or over, $R^{29}$'s may be the same or different.

50. A method for preparing a compound of the general formula (3) defined in claim 48, which method comprises reacting an aromatic aldehyde compound of the following general formula (7) with a methylphosphonic ester derivative of the following general formula (14), or a corresponding methyl triarylphosphonium compound thereof:

(7)

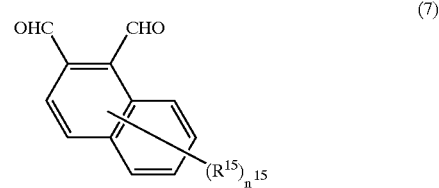

wherein $R^{15}$ independently represents an unsubstituted or substituted alkyl group, an unsubstituted or substituted alkoxy group, a halogen, a cyano group or a nitro group, and $n^{15}$ is an integer of 0, 1, 2, 3, 4, 5 or 6 provided that when $n^{15}$ is 2 or over, $R^{15}$'s may be the same or different; and (14)

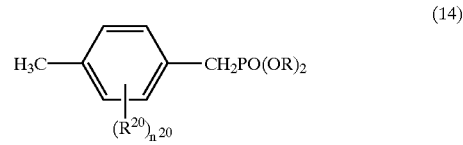

wherein $R^{20}$ represents an unsubstituted or substituted alkyl group, an unsubstituted or substituted alkoxy group, a halogen atom, a cyano group or a nitro group, and $n^{20}$ is an integer of 0, 1, 2, 3 or 4 provided that if $n^{20}$ is 2 or over, $R^{20}$'s may be the same or different.

51. A compound according to claim 47, wherein said compound consists of a compound of the general formula (3a).

52. A method for preparing a compound of the general formula (3a) defined in claim 51, which method comprises reacting a bismethylphosphonic ester derivative of the following formula (4a), or a corresponding methyl triarylphosphonium compound thereof, with an aldehyde compound of the following general formula (13):

(4a)

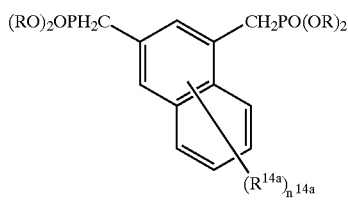

wherein $R^{14a}$ represents an unsubstituted or substituted alkyl group, an unsubstituted or substituted alkoxy group, a halogen group, a cyano group or a nitro group, $n^{14a}$ is an integer of 0, 1, 2, 3, 4, 5 or 6 provided that if $n^{14a}$ is an integer of 2 or over, $R^{14a}$'s may be the same or different, and R represents an unsubstituted or substituted alkyl group having from 1 to 4 carbon atoms; and (13)

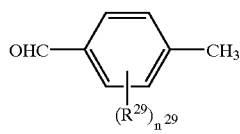

wherein $R^{29}$ represents an unsubstituted or substituted alkyl group, an unsubstituted or substituted alkoxy group, a halogen atom, a cyano group or a nitro group as defined as $R^{14}$ in the formula (4), and $n^{29}$ is an integer of 0, 1, 2, 3 or 4 provided that if $n^{29}$ is 2 or over, $R^{29}$'s may be the same or different.

53. A method for preparing a compound of the general formula (3a) defined in claim 51, which method comprises reacting an aromatic aldehyde compound of the following general formula (7a) with a methylphosphonic ester derivative of the following general formula (14), or a corresponding methyl triarylphosphonium compound thereof:

(7a)

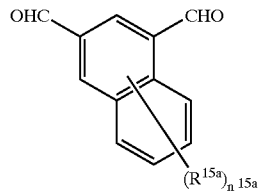

wherein $R^{15a}$ independently represents an unsubstituted or substituted alkyl group, an unsubstituted or substituted alkoxy group, a halogen, a cyano group or a nitro group, and $n^{15a}$ is an integer of 0, 1, 2, 3, 4, 5 or 6 provided that when $n^{15a}$ is 2 or over, $R^{15a}$'s may be the same or different; and (14)

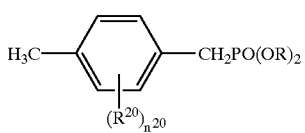

wherein $R^{20}$ represents an unsubstituted or substituted alkyl group, an unsubstituted or substituted alkoxy group, a halogen atom, a cyano group or a nitro group, and $n^{20}$ is an integer of 0, 1, 2, 3 or 4 provided that if $n^{20}$ is 2 or over, $R^{20}$'s may be the same or different.

54. A compound according to claim 47, wherein said compound consists of a compound of the general formula (3b).

55. A method for preparing a compound of the general formula (3b) defined in claim 54, which method comprises reacting a bismethylphosphonic ester derivative of the following formula (4b), or a corresponding methyl triarylphosphonium compound thereof, with an aldehyde compound of the following general formula (13):

(4b)

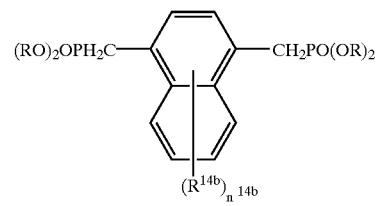

wherein $R^{14b}$ represents an unsubstituted or substituted alkyl group, an unsubstituted or substituted alkoxy group, a halogen group, a cyano group or a nitro group, $n^{14b}$ is an integer of 0, 1, 2, 3, 4, 5 or 6 provided that if $n^{14b}$ is an integer of 2 or over, $R^{14b}$'s may be the same or different, and R represents an unsubstituted or substituted alkyl group having from 1 to 4 carbon atoms; and (13)

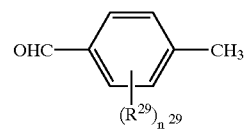

wherein $R^{29}$ represents an unsubstituted or substituted alkyl group, an unsubstituted or substituted alkoxy group, a halogen atom, a cyano group or a nitro group as defined as $R^{14}$ in the formula (4), and $n^{29}$ is an integer of 0, 1, 2, 3 or 4 provided that if $n^{29}$ is 2 or over, $R^{29}$'s may be the same or different.

56. A method for preparing a compound of the general formula (3b) defined in claim 54, which method comprises reacting an aromatic aldehyde compound of the following general formula (7b) with a methylphosphonic ester derivative of the following general formula (14), or a corresponding methyl triarylphosphonium compound thereof:

(7b)

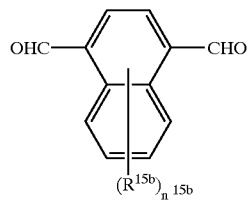

wherein $R^{15b}$ independently represents an unsubstituted or substituted alkyl group, an unsubstituted or substituted alkoxy group, a halogen, a cyano group or a nitro group, and $n^{15b}$ is an integer of 0, 1, 2, 3, 4, 5 or 6 provided that when $n^{15b}$ is 2 or over, $R^{15b}$'s may be the same or different; and

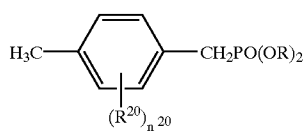

(14)

wherein $R^{20}$ represents an unsubstituted or substituted alkyl group, an unsubstituted or substituted alkoxy group, a halogen atom, a cyano group or a nitro group, and $n^{20}$ is an integer of 0, 1, 2, 3 or 4 provided that if $n^{20}$ is 2 or over, $R^{20}$'s may be the same or different.

57. A compound according to claim 47, wherein said compound consists of a compound of the general formula (3c).

58. A method for preparing a compound of the general formula (3c) defined in claim 57, which method comprises reacting a bismethylphosphonic ester derivative of the following formula (4c), or a corresponding methyl triarylphosphonium compound thereof, with an aldehyde compound of the following general formula (13):

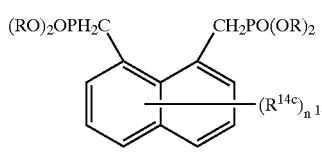

(4c)

wherein $R^{14c}$ represents an unsubstituted or substituted alkyl group, an unsubstituted or substituted alkoxy group, a halogen group, a cyano group or a nitro group, $n^{14c}$ is an integer of 0, 1, 2, 3, 4, 5 or 6 provided that if $n^{14c}$ is an integer of 2 or over, $R^{14c}$'s may be the same or different, and R represents an unsubstituted or substituted alkyl group having from 1 to 4 carbon atoms; and

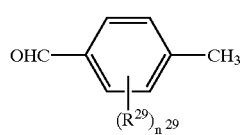

(13)

wherein $R^{29}$ represents an unsubstituted or substituted alkyl group, an unsubstituted or substituted alkoxy group, a halogen atom, a cyano group or a nitro group as defined as $R^{14}$ in the formula (4), and $n^{29}$ is an integer of 0, 1, 2, 3 or 4 provided that if $n^{29}$ is 2 or over, $R^{29}$'s may be the same or different.

59. A method for preparing a compound of the general formula (3c) defined in claim 57, which method comprises reacting an aromatic aldehyde compound of the following general formula (7c) with a methylphosphonic ester derivative of the following general formula (14), or a corresponding methyl triarylphosphonium compound thereof:

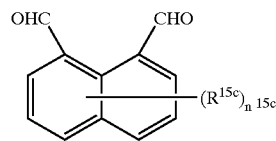

(7c)

wherein $R^{15c}$ independently represents an unsubstituted or substituted alkyl group, an unsubstituted or substituted alkoxy group, a halogen, a cyano group or a nitro group, and $n^{15c}$ is an integer of 0, 1, 2, 3, 4, 5 or 6 provided that when $n^{15c}$ is 2 or over, $R^{15c}$'s may be the same or different; and

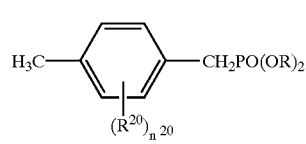

(14)

wherein $R^{20}$ represents an unsubstituted or substituted alkyl group, an unsubstituted or substituted alkoxy group, a halogen atom, a cyano group or a nitro group, and $n^{20}$ is an integer of 0, 1, 2, 3 or 4 provided that if $n^{20}$ is 2 or over, $R^{20}$'s may be the same or different.

60. A compound according to claim 47, wherein said compound consists of a compound of the general formula (3d).

61. A method for preparing a compound of the general formula (3d) defined in claim 60, which method comprises reacting a bismethylphosphonic ester derivative of the following formula (4d), or a corresponding methyl triarylphosphonium compound thereof, with an aldehyde compound of the following general formula (13):

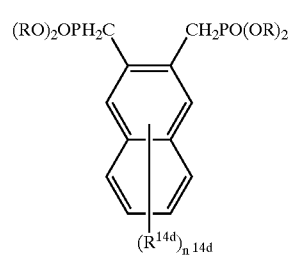

(4d)

wherein $R^{14d}$ represents an unsubstituted or substituted alkyl group, an unsubstituted or substituted alkoxy group, a halogen group, a cyano group or a nitro group, $n^{14d}$ is an integer of 0, 1, 2, 3, 4, 5 or 6 provided that if $n^{14d}$ is an integer of 2 or over, $R^{14d}$'s maybe the same or different, and R represents an unsubstituted or substituted alkyl group having from 1 to 4 carbon atoms; and

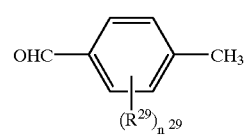

(13)

wherein $R^{29}$ represents an unsubstituted or substituted alkyl group, an unsubstituted or substituted alkoxy group, a halogen atom, a cyano group or a nitro group as defined as $R^{14}$ in the formula (4), and $n^{29}$ is an integer of 0, 1, 2, 3 or 4 provided that if $n^{29}$ is 2 or over, $R^{29}$'s may be the same or different.

62. A method for preparing a compound of the general formula (3d) defined in claim 60, which method comprises reacting an aromatic aldehyde compound of the following general formula (7d) with a methylphosphonic ester derivative of the following general formula (14), or a corresponding methyl triarylphosphonium compound thereof:

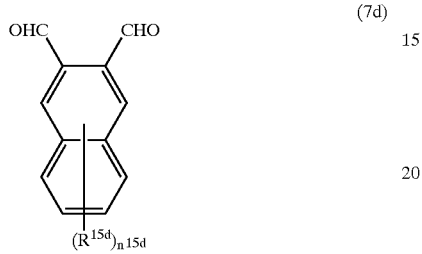

(7d)

wherein $R^{15d}$ independently represents an unsubstituted or substituted alkyl group, an unsubstituted or substituted alkoxy group, a halogen, a cyano group or a nitro group, and $n^{15d}$ is an integer of 0, 1, 2, 3, 4, 5 or 6 provided that when $n^{15d}$ is 2 or over, $R^{15d}$'s may be the same or different; and

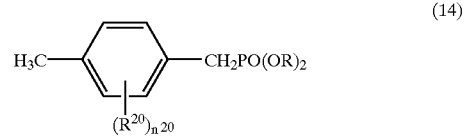

(14)

wherein $R^{20}$ represents an unsubstituted or substituted alkyl group, an unsubstituted or substituted alkoxy group, a halogen atom, a cyano group or a nitro group, and $n^{20}$ is an integer of 0, 1, 2, 3 or 4 provided that if $n^{20}$ is 2 or over, $R^{20}$'s may be the same or different.

* * * * *